United States Patent [19]

Yue et al.

[11] Patent Number: 5,658,751
[45] Date of Patent: Aug. 19, 1997

[54] SUBSTITUTED UNSYMMETRICAL CYANINE DYES WITH SELECTED PERMEABILITY

[75] Inventors: Stephen T. Yue; Victoria L. Singer, both of Eugene; Bruce L. Roth, Corvallis; Thomas J. Mozer; Paul J. Millard, both of Eugene; Laurie J. Jones, Monroe; Xiaokui Jin, Springfield; Richard P. Haugland, Eugene, all of Oreg.

[73] Assignee: Molecular Probes, Inc., Eugene, Oreg.

[21] Appl. No.: 331,031

[22] Filed: Oct. 27, 1994

Related U.S. Application Data

[63] Continuation-in-part of Ser. No. 90,890, Jul. 12, 1994, Pat. No. 5,436,134, which is a continuation-in-part of Ser. No. 47,683, Apr. 13, 1993, abandoned.

[51] Int. Cl.$^6$ .............................. C12Q 1/04; C12Q 1/02; G01N 33/00; C07H 19/20
[52] U.S. Cl. .................. 435/34; 435/4; 435/29; 435/6; 436/94; 436/800; 536/26.73; 536/1.11; 536/25.6
[58] Field of Search .................... 435/34, 4, 29, 435/6; 436/94, 800; 536/26.73, 1.11, 25.6

[56] References Cited

U.S. PATENT DOCUMENTS

| | | | |
|---|---|---|---|
| 4,665,024 | 5/1987 | Mansour et al. | 435/34 |
| 4,883,867 | 11/1989 | Lee et al. | 436/94 |
| 4,937,198 | 6/1990 | Lee et al. | 436/94 |
| 5,321,130 | 6/1994 | Yue et al. | 536/23.1 |
| 5,436,134 | 7/1995 | Haugland et al. | 435/34 |

FOREIGN PATENT DOCUMENTS

WO93/06482  4/1993  WIPO.
WO94/24213  10/1994  WIPO.

OTHER PUBLICATIONS

Brooker, et al., J. Am. Chem. Soc. 64, 199 (1942).
Davidson, The Biochemistry of the Nucleic Acids (1976).
Wittung, et al., Nature 368, 561 (1994).
Diwu et al., Cytometry supp. 7, p. 77, Abstract 426B (1994).
Wawzonek, et al., J. Heterocyclic Chem. 25, 381 (1988).
Elderfield, Heterocyclic Compounds, vol. 4, pp. 1–331 (1952).
Marson, Tetrahedron., 48, 3659 (1992).
Saitoh, et al., Cell 76, 609 (1994).
Hongyo, et al., Nucleic Acids Research 21, 3637 (1993).
Noueiry, et al., Cell 76 925 (1994).
Perkins, et al., Science 264, 822 (1994).
Perkins et al., Science 264, 819 (1994).
Bensimon, et al., Science 265, 2096 (1994).
Goodwin, et al., Nucleic Acids Research 21, 803 (1993).
Castro, et al., Anal. Chem. 65, 849 (1993).
Kudinova, et al., Chemical Abstracts 93:241180j (1993).
Kudinova et al., Khim. Geterotsikl. Soedin. 7, 903 (1980).
Simbera, et al., Chemical Abstracts 89:112299y (1978).

*Primary Examiner*—John Kight
*Assistant Examiner*—Louise Leary
*Attorney, Agent, or Firm*—Allegra J. Helfenstein; Anton E. Skaugset

[57] ABSTRACT

The invention describes the preparation and use of fluorescent stains for nucleic acids derived from unsymmetrical cyanine dyes comprising a substituted benzazolium ring system linked by a methine bridge to a pyridinium or quinolinium ring system having at least one substituent on the pyridinium or quinolinium ring that contains a heteroatom. The presence of the heteroatom-containing substituent results in higher sensitivity to oligonucleotides and larger nucleic acid polymers in a wide range of cells and gels, and for use in analysis of cell structure, membrane integrity or function.

97 Claims, 9 Drawing Sheets

Figure 5
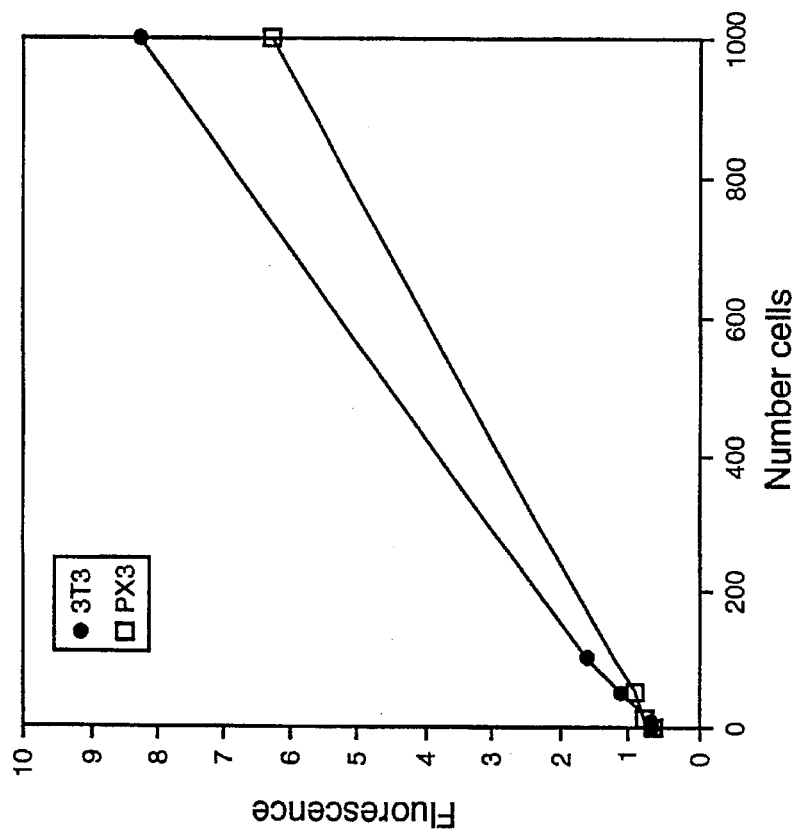
Figure 5B
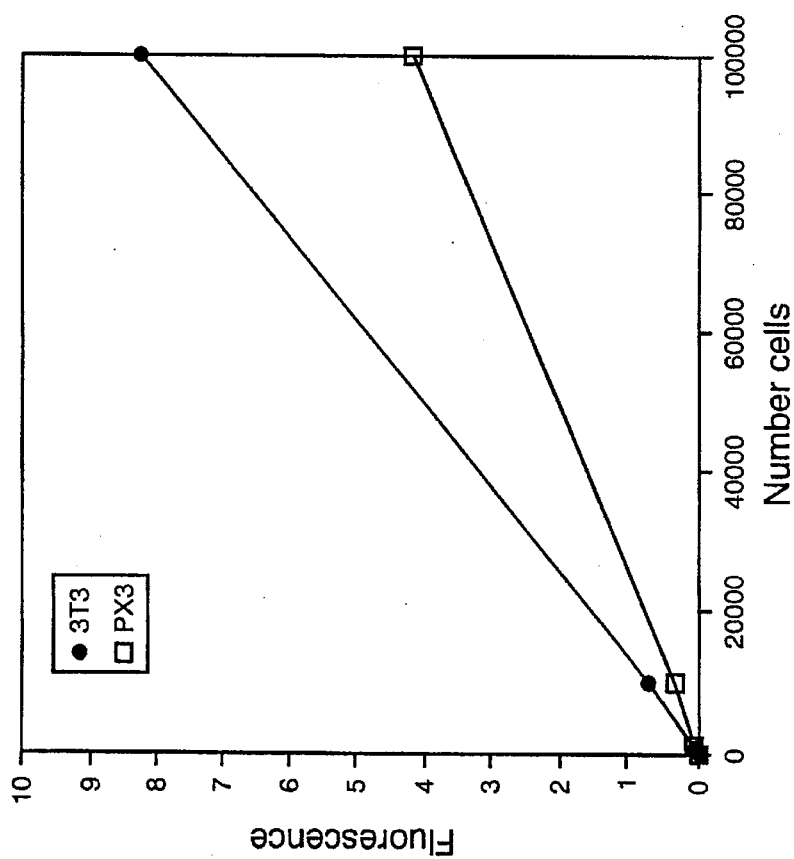
Figure 5A

Figure 8
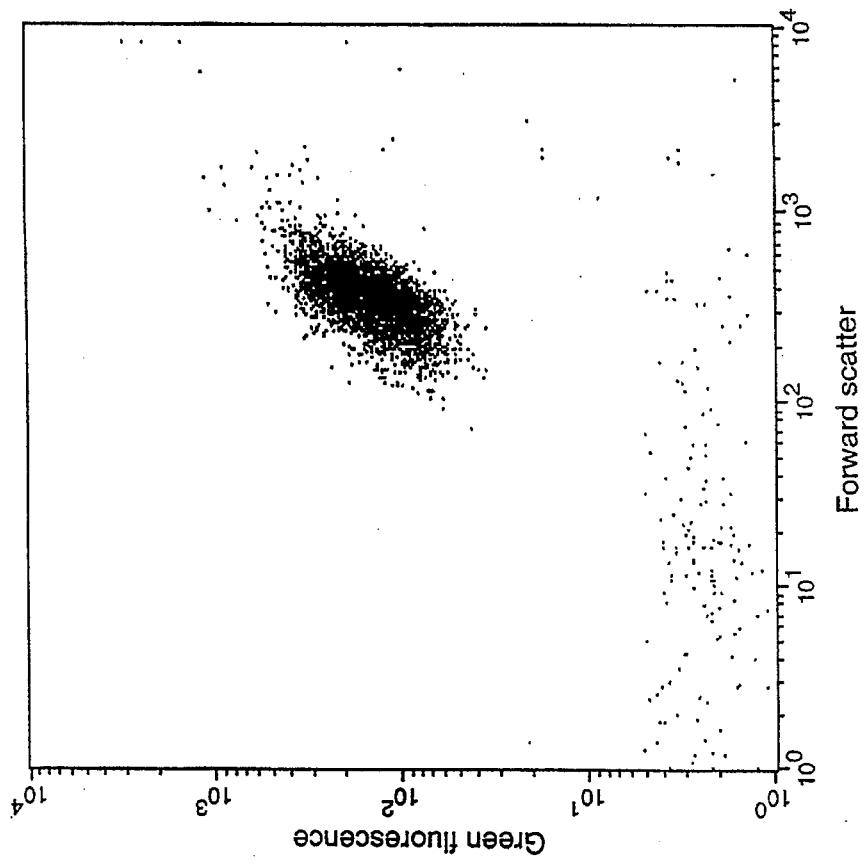
Figure 8B
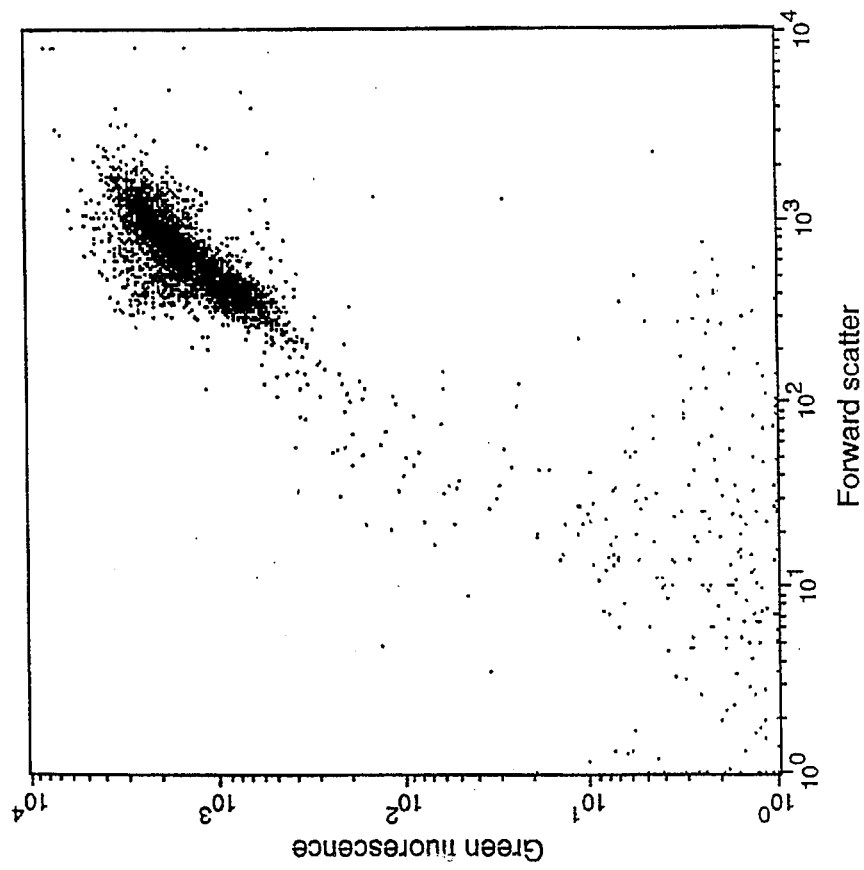
Figure 8A

SUBSTITUTED UNSYMMETRICAL CYANINE DYES WITH SELECTED PERMEABILITY

This is a continuation-in-part of application Ser. No. 08/090,890, filed Jul. 12, 1994, now U.S. Pat. No. 5,436,134 which is itself a continuation-in-part of application Ser. No. 08/047,683, filed Apr. 13, 1993, now abandoned.

FIELD OF THE INVENTION

The invention relates to fluorescent dyes for nucleic acids. In particular, the invention relates to dyes derived from unsymmetrical cyanine dyes having defined substituents on the quinolinium or pyridinium ring system, where the substituents serve to increase or decrease the permeability, selectivity and binding affinity of the nucleic acid stains. The subject dyes, which form a fluorescent complex in combination with nucleic acids, can be used in analyzing a wide range of materials, including biological and environmental samples.

BACKGROUND INFORMATION

In many fields of life sciences research, including biological, biomedical, genetic, fermentation, aquaculture, agricultural, forensic and environmental research, there is a need to identify nucleic acids, qualitatively and quantitatively, in pure solutions and in biological samples. Such applications require a fast, sensitive, and selective methodology that can detect minute amounts of nucleic acids in a variety of media, whether or not the nucleic acid is contained in cells.

Although certain unsymmetrical cyanine dyes were first described before the genetic role of nucleic acids was established (Brooker, et at., J. AM. CHEM. SOC. 64, 199 (1942)), some unsymmetrical cyanine dyes are now known as effective fluorescent stains of DNA and RNA. The compound sold as Thiazole Orange has particular advantages in reticulocyte analysis (U.S. Pat. No. 4,883,867 to Lee, et at. (1989)) or in preferentially staining bloodborne parasites (U.S. Pat. No. 4,937,198 to Lee, et al. (1990)). Thiazole Orange readily stains many mammalian cells, yet does not effectively stain some eukaryotic cells.

Attachment of various cyclic structures to the pyrdinium or quinolinium ring system of the unsymmetrical cyanine dye was found to make the nucleic acid stains highly permeant to gels and a wider variety of cell types, including both gram-positive and gram-negative bacteria, yeasts, and eukaryotic cells as well as prokaryotic cells, as described in copending applications CYCLIC-SUBSTITUTED UNSYMMETRICAL CYANINE DYES (Ser. No. 08/090,890 to Haugland, et al. filed Jul. 12, 1993), FLUORESCENT ASSAY FOR BACTERIAL GRAM REACTION (Ser. No. 08/146,328 to Roth et at. filed Nov. 1, 1993), FLUORESCENT VIABILITY ASSAY USING CYCLIC-SUBSTITUTED UNSYMMETRICAL CYANINE DYES (Ser. No. 08/148,847 to Millard, et al. filed Nov. 8, 1993), and VIABILITY ASSAY FOR YEAST AND OTHER FUNGI (Ser. No. 08/206,081 to Roth, et al. filed Mar. 3, 1994); and PCT application 94/04127 (the specification of which is incorporated by reference).

Attachment of a cationic side chain at the nitrogen of the pyridinium or quinolinium ring system of the unsymmetrical cyanine dyes, on the other hand, was shown to make the stains relatively impermeant to all cells, except cells, particularly mammalian cells, where cell membrane integrity was destroyed, as described in UNSYMMETRICAL CYANINE DYES WITH CATIONIC SIDE CHAINS (U.S. Pat. No. 5,321,130 to Yue et al. (1994)). A second type of dye, in which a dye monomer is attached at the nitrogen of the quinolinium or pyridinium ring system to form dimeric compounds as described in DIMERS OF UNSYMMETRICAL CYANINE DYES (PCT 92/07867) and DIMERS OF UNSYMMETRICAL CYANINE DYES CONTAINING PYRIDINIUM MOIETIES (Ser. No. 08/043,665 to Yue, et al. filed Apr. 5, 1993) that are also relatively impermeant to all cells unless the cell membrane has been disrupted. Although these impermeant dyes were found to have the further advantage of increased binding affinity for nucleic acids, resulting in increased sensitivity for detection of cell free nucleic acids, a number of these dyes were also found to have a number of disadvantages for some applications, including a slow rate of equilibrium binding, electrostatic attraction to glass surfaces, moderate salt sensitivity, reduced photostability, lower quantum yield, relatively lower sensitivity of detection of nucleic acids in gelse and in solutions, and limited permeability to dead prokaryotic cells.

The dyes of the present invention are unsymmetrical cyanine dyes containing a defined substituent on the pyridinium or quinolinium ring system or a substituent immediately adjacent to the nitrogen atom of the pyridinium or quinolinium ring that modifies the permeability, selectivity and affinity of the dye for nucleic acids. Members of this class of dyes are more effective in detection of cell membrane integrity and in the staining or detection of nucleic acids, including DNA and RNA, in gels and in solutions, and in living and dead cells. Dyes substituted at the position adjacent to the ring nitrogen generally have unexpectedly higher quantum yields than dyes not substituted at that position. In addition, the ring substituent is easily modified, particularly by inclusion of an appropriate heteroatom in the substituent, to allow selectable alteration of the permeability and affinity of the dyes. Furthermore, by simple synthetic modification, a family of dyes having absorption and emission spectral properties that cover most of the visible and near-infrared spectrum can be prepared. Selection of an appropriately substituted dye enhances the sensitivity of analysis of nucleic acids utilizing a variety of techniques.

DESCRIPTION OF DRAWINGS

FIG. 5: Linear fluorescence response as a function of cell number, as described in Example 41. Standard concentration plots are shown for both NIH/3T3 cells and PX3 cells.

FIG. 8: Analysis of bacterial metabolic activity, as described in Example 49. The cluster of data in FIG. 8A represents metabolically active bacteria. The signal cluster in FIG. 8B represents metabolically quiescent bacteria.

SUMMARY OF THE INVENTION AND DESCRIPTION OF PREFERRED EMBODIMENTS

Figure 1:
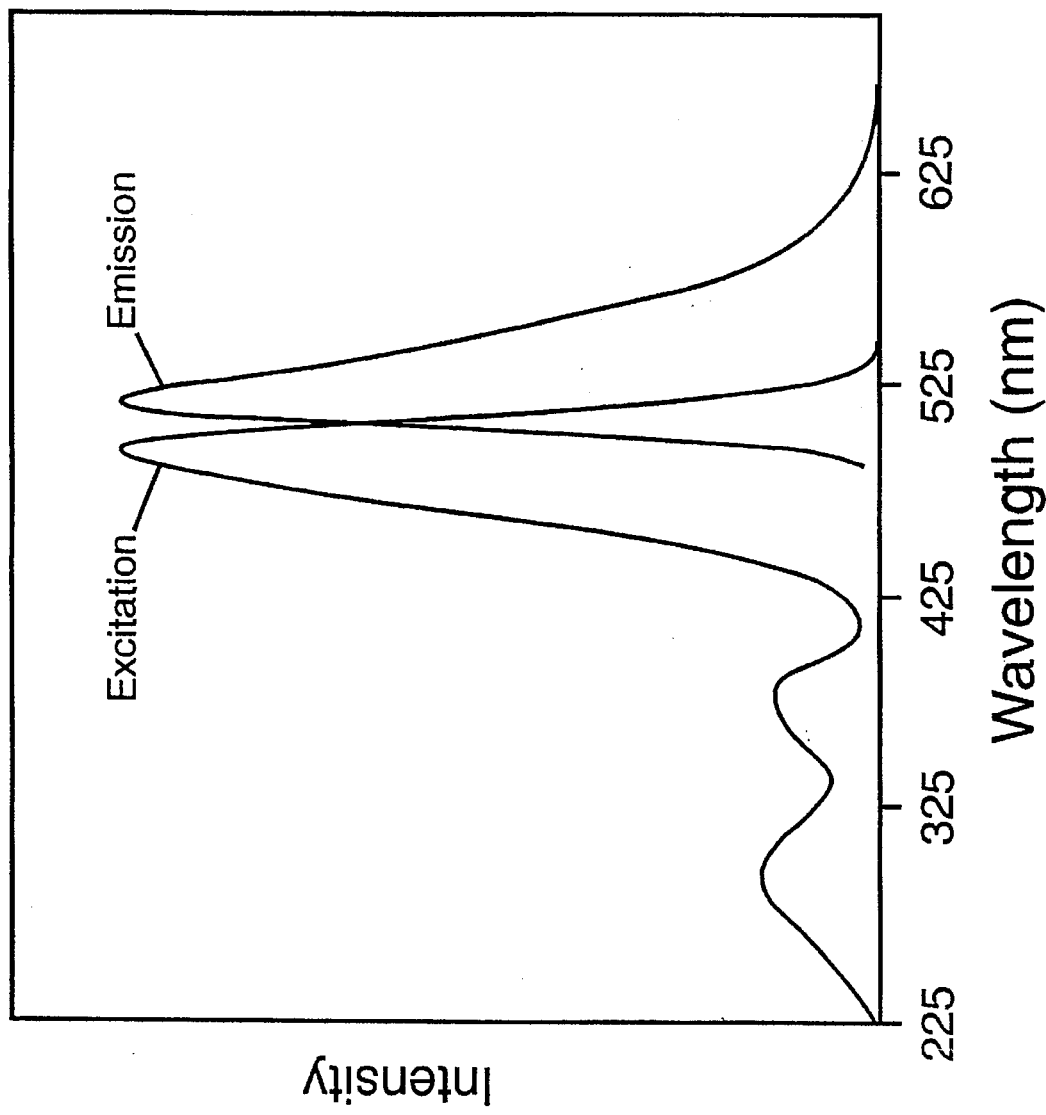
FIG. 1: The fluorescence excitation and emission spectra for Dye 937 in the presence of ds calf thymus DNA. Note the lower intensity absorbances in the UV region of the excitation spectrum, indicating that fluorescence can be generated by excitation at those wavelengths, albeit at lower fluorescence yields.

The substituted unsymmetrical cyanine dyes of the invention are virtually non-fluorescent when diluted in aqueous solution. When bound to nucleic acid polymers such as DNA and RNA, however, the resultant dye-nucleic acid complex becomes extremely fluorescent upon illumination. The dyes of the present invention label nucleic acids in a wide variety of samples, particularly in aqueous solutions, electrophoretic gels, and a wide variety of cells, including microorganisms.

Dye Structure

The dyes of the invention comprise: 1) a first heterocyclic ring system that is a substituted benzazolium ring, 2) a bridging methine and 3) a second heterocyclic ring that is a pyridinium or quinolinium ring system, one or more positions of which may be substituted by a TAIL that contains at least one heteroatom. The first and second ring systems are optionally further substituted by a variety of substituents, as described below.

TAIL

TAIL is a heteroatom-containing side chain, that is described by the formula LINK-SPACER-CAP. LINK is the linking moiety by which TAIL is attached to the core structure of the dyes of the present invention. SPACER is a covalent linkage that connects LINK to CAP. CAP is the portion of TAIL that possesses a heteroatom component.

LINK is a single covalent bond, an ether linkage (—O—), a thioether linkage (—S—), or an amine linkage (—$NR^2$—). In each embodiment, LINK forms the attachment between the dye core structure and SPACER. When LINK is an amine, the amine substituent ($R^{20}$) is optionally H, such that LINK=—NH—. Alternatively, $R^{20}$ is a linear or branched alkyl having 1–8 carbons. In another embodiment of the invention, $R^{20}$ is —SPACER'—CAP', yielding a TAIL having the formula

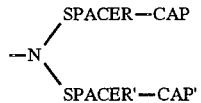

where SPACER' and CAP', respectively, may be the same as or different from SPACER and CAP, and are selected from the same alternatives defined for SPACER and CAP, respectively. For the sake of simplifying the description, SPACER and CAP are defined with the understanding that a description of SPACER includes SPACER', and a description of CAP includes CAP'.

SPACER is a covalent linkage that joins LINK and CAP. SPACER is a linear, branched, cyclic, heterocyclic, saturated or unsaturated arrangement of 1–16 C, N, P, O or S atoms. Alternatively, SPACER is a single covalent bond, such that both LINK and SPACER are not simultaneously single covalent bonds. Preferably, the SPACER linkage must begin and end with a carbon atom. Typically, if SPACER consists of a single atom, it is required to be a carbon atom, so that the first and last atom in SPACER (in this specific instance, they are the same atom) is a carbon. The 1–16 atoms making up SPACER are combined using any appropriate combination of ether, thioether, amine, ester, or amide bonds; or single, double, triple or aromatic carbon-carbon bonds; or phosphorus-oxygen bonds; or phosphorus-sulfur bonds; or nitrogen-nitrogen bonds; or nitrogen-oxygen bonds; or aromatic or heteroaromatic bonds. SPACER is further substituted by hydrogen to accommodate the valence state of each atom in SPACER.

Generally, the atoms of SPACER are arranged such that all heteroatoms in the linear backbone of SPACER are separated by at least one carbon atom, and preferably separated by at least two carbon atoms. Typically, SPACER is 1–6 carbon atoms in a linear or branched saturated chain. In one embodiment of the invention, SPACER incorporates a 6-membered aromatic ring (phenylene linkage). In another embodiment of the invention, SPACER incorporates a 5- or 6-membered heteroaromatic ring, wherein the heteroatoms are O, N, or S. Alternatively, SPACER incorporates amide linkages, ester linkages, simple ethers and thioethers, and amines in a linear arrangement, such as —$CH_2$—$CH_2$—(C=O)—NH—$CH_2$—$CH_2$—$CH_2$—. Preferably, SPACER is an alkylene (—$(CH_2)_k$—, where k=1–8).

LINK and SPACER, in combination, serve to attach a heteroatom-containing group, CAP, to the dye core structure. CAP may contain oxygen, sulfur or nitrogen, according to the formulas —O—$R^{21}$, —S—$R^{21}$, —$NR^{21}R^{22}$, or —$N^+R^{21}R^{22}R^{23}$ $\Psi^-$. The substituents $R^{21}$, $R^{22}$, and $R^{23}$ are independently H, or a linear or branched alkyl or cycloalkyl having 1–8 carbons. Where any of $R^{21}$, $R^{22}$ and $R^{23}$ are alkyl or cycloalkyl, they are optionally further substituted by halogen, hydroxy, alkoxy having 1–8 carbons, amino, carboxy, or phenyl, where phenyl is optionally further substituted by halogen, hydroxy, alkoxy having 1–8 carbons, amino, aminoalkyl having 1–8 carbons, or carboxyalkyl having 1–8 carbons. In another embodiment of the invention, one or more of $R^{21}$, $R^{22}$ and $R^{23}$, taken in combination with SPACER forms a 5- or 6-membered ring that is aromatic, heteroaromatic, alicyclic or heteroalicyclic ring. When the 5- or 6-membered ring is heteroaromatic or heteroalicyclic, the ring contains 1-3 heteroatoms that are O, N or S. Alternatively, one or more of $R^{21}$, $R^{22}$, and $R^{23}$, taken in combination with $R^{20}$ and SPACER, forms a 5- or 6-membered ring that is aromatic, heteroaromatic, alicyclic or heteroalicyclic ring, as described above. Preferably, $R^{21}$, $R^{22}$ are hydrogen, or alkyls having 1–8 carbons. $R^{23}$ is typically H or alkyl having 1–8 carbons.

When CAP is —$N^+R^{21}R^{22}R^{23}$ $\Psi^-$, the biologically compatible counterion $\Psi^-$ balances the positive charge present on the CAP nitrogen, which is a quaternary ammonium salt. As used herein, a substance that is biologically compatible is not toxic as used, and does not have a substantially deleterious effect on biomolecules. Examples of $\Psi^-$ include, among others, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Preferred $\Psi^-$ counterions are chloride, iodide, perchlorate and various sulfonates.

Additionally, there are several embodiments of the present invention wherein CAP incorporates a cyclic structure. In these embodiments, CAP typically incorporates a 5- or 6-membered nitrogen-containing ring, optionally including an additional heteroatom (typically oxygen), where the ring nitrogen is optionally substituted by $R^{23}$ to give an ammonium salt. Specific versions of CAP include, but are not limited to, those listed in Table 1.

TABLE 1

Examples of specific CAP moieties

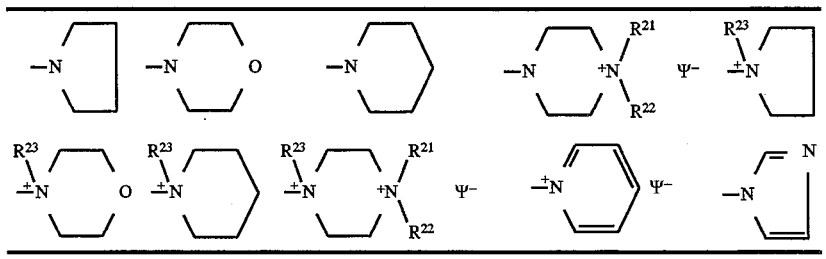

CAP is preferably —$NR^{21}R^{22}$ or —$N^+R^{21}R^{22}R^{23}\Psi^-$, where $R^{21}$, $R^{22}$, and $R^{23}$ are alkyls having 1–6 carbons. More preferably CAP is —$N(CH_3)_2$ or —$N^+(CH_3)_3\Psi^-$.

Preferably TAIL contains 6–10 non-hydrogen atoms, including LINK and CAP.

Selected examples of TAIL are listed in Table 2. For each TAIL, the identities of LINK, SPACER and CAP are specified. Where $R^{21}$, $R^{22}$, or $R^{23}$ combined with either $R^{20}$ or SPACER, the combination is indicated in the table.

TABLE 2

Specific examples of TAIL moieties

| TAIL | LINK | SPACER/SPACER' | CAP/CAP' |
|---|---|---|---|
| (structure) | $-N(CH_2CH_2CH_3)-$ | $-CH_2-CH_2-CH_2-$ | $-N(CH_3)_2$ |
| (structure) | $-N(CH_2CH_2CH_3)-$ | $-CH_2-CH_2-CH_2-$ | $-N^+(CH_3)_3$ |
| (structure) | $-N-SPACER'-CAP'$ | $-CH_2-CH_2-CH_2-$ | $-N(CH_3)_2$ |
| | | $-CH_2-CH_2-CH_2-$ | $-N(CH_3)_2$ |

TABLE 2-continued

Specific examples of TAIL moieties

| TAIL | LINK | SPACER/SPACER' | CAP/CAP' |
|---|---|---|---|
| (branched tail with two $-N^+(CH_3)_2-$ groups joined via central N) | $-N-SPACER'-CAP'$ | $-CH_2-CH_2-CH_2-$ | $-N^+(CH_3)_3$ |
| (tail with two $-N-$ groups linked through S) | $-S-$ | $-CH_2-CH_2-CH_2-$ | $-N^+(CH_3)_3$ |
| (tail with $-N^+-$ linked through S) | $-S-$ | $-CH_2-CH_2-$ | $-N(CH_3)_2$ |
| (piperazine-type tail with $-N-$) | $-N(-R^{22})-$ | $-CH_2-CH_2-$ | $-N^+(CH_3)_3$ |
| (piperazine-type tail with $-N^+-$) | $-N(-R^{23})-$ | $-CH_2-CH_2-$ | $-N(CH_3)(CH_2-CH_2-R^{20})$ |
| (thiourea-type tail HN–C(=S)–) | $-S-$ | $-C(-R^{22})=N-CH_2-CH_2-CH_2-$ | $-N^+(CH_3)_2(CH_2-CH_2-R^{20})$ |
| (benzyl ammonium tail with $-N^+-$ and phenyl) | bond | (p-phenylene)$-CH_2-$ | $-NH(-SPACER)$ |
| (tail with $-N-$ linked through O) | $-O-$ | $-CH_2-CH_2-CH_2-$ | $-N^+(CH_3)(CH_2CH_3)_2$ |
| | | | $-N(CH_3)_2$ |

TABLE 2-continued

Specific examples of TAIL moieties

| TAIL | LINK | SPACER/SPACER' | CAP/CAP' |
|---|---|---|---|
| aryl-O-CH₂-CH₂-CH₂-N⁺(CH₃)₃ (tail shown as phenyl-O-CH₂CH₂CH₂-N⁺(CH₃)₂-) | bond | (p-phenylene)—O—CH₂—CH₂—CH₂— | —N⁺(CH₃)₃ |
| (diethyl thiophosphate group) | —S— | $\overset{S}{\underset{\underset{O-CH_2CH_3}{\parallel}}{P}}$—O—CH₂CH₃ | —OCH₂CH₃ |
| ⋯NH—N(CH₃)₂ | —NH— | bond | —N(CH₃)₂ |
| ⋯S-CH₂CH₂-(C=O)-NH-CH₂CH₂CH₂-N(CH₃)₂ | —S— | —CH₂—CH₂—(C=O)—NH—CH₂—CH₂—CH₂— | —N(CH₃)₂ |

Core Structure

The core structure of the dyes of the present invention are described by the formula:

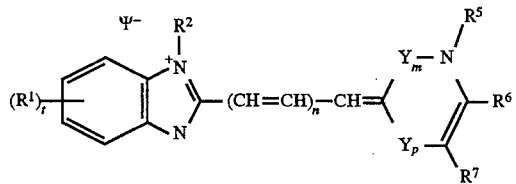

where the substituted benzazolium ring system on the left is linked by a methine bridge to the right-hand pyridinium or quinolinium ring system. One or more substituents on the core structure is optionally a TAIL.

Although $R^1$ on the benzazolium ring system is usually H, incorporation of one or more non-hydrogen substituents $R^1$ can be used to fine tune the absorption and emission spectrum of the resulting dye. The benzazole may contain more than one substituent $R^1$, which may be the same or different (t=1–4). Each $R^1$ is optionally an alkyl group having from 1–6 carbons; or a trifluoromethyl; or a halogen; or an alkoxy having 1–6 carbons. Typically, each compound contains no more than one $R^1$ that is not H. Preferably, $R^1$ is H or alkoxy, more preferably each $R^1$ is H.

The substituent $R^2$ is an alkyl group having 1–6 carbons, preferably methyl or ethyl, more preferably methyl.

The counterion $\Psi^-$ is a biologically compatible ion, as described above. Preferred $\Psi^-$ counterions are chloride, iodide, perchlorate and various sulfonates.

X is one of O, S, Se or $NR^{15}$, where $R^{15}$ is H or an alkyl group having 1–6 carbons. Alternatively, X is $CR^{16}R^{17}$, where $R^{16}$ and $R^{17}$, which may be the same or different, are independently H or alkyl groups having 1–6 carbons, or the carbons of $R^{16}$ and $R^{17}$ taken in combination complete a five or six membered saturated ring. When X is $CR^{16}R^{17}$, $R^{16}$ and $R^{17}$ are typically methyls. Preferably, X is O or S, more preferably X is S.

The two heterocyclic ring systems are linked by 1, 3 or 5 methine (—CH=) groups in such a way as to permit extensive electronic delocalization. When n=0 the dyes are unsymmetrical monomethine dyes; when n=1 the dyes are trimethine dyes; when n=2, the dyes are pentamethine dyes. As with similar compounds, the number of methine groups between the heteroaromatic rings influences the spectral properties of the dye. The monomethine dyes of the present invention that are pyridiniums typically have blue to blue-green fluorescence emission, while quinoliniums have green to yellow-green fluorescence emission. The trimethine dye analogs are substantially shifted toward red wavelengths, and the pentamethine dyes are shifted even further, often exhibiting infrared fluorescence emission. Preferably n=0 or 1, more preferably n=0.

The N-bound substituent $R^5$ is an alkyl, alkenyl, polyalkenyl, alkynyl or polyalkynyl group having 1–6 carbons. Alternatively, $R^5$ is a cyclic substituent or a TAIL. Typically $R^5$ is an alkyl having 1–6 carbons, preferably 1–2 carbons, or $R^5$ is a cyclic substituent. Typically, when $R^5$ is a TAIL, the SPACER moiety incorporates a phenylene linkage.

Specifically, when $R^5$ is a cyclic substituent, $R^5$ is an aryl, a heteroaryl, or a cycloalkyl having 3–10 carbons. As used herein, an aryl is a phenyl or naphthyl group, and a heteroaryl substituent is a 5 or 6-membered heteroaromatic ring, wherein the heteroatom is O, N or S. The cyclic substituent is optionally substituted by halogen, amino, alkyl, perfluoroalkyl, alkylamino, dialkylamino, alkoxy or carboxyalkyl, wherein each alkyl group has 1–6 carbons. The cyclic substituent is preferably a substituted or unsubstituted naphthyl, phenyl, thienyl, or cycloalkyl having 3–10 carbons, more preferably, the cyclic substituent is phenyl.

The second ring system contains a ring fragment Y that is —$CR^3$=$CR^4$—, with subscripts p and m equal to 0 or 1, such that p+m=1. For all embodiments, the ring contains a 6 membered pyridinium-based heterocycle according to one of these formulations

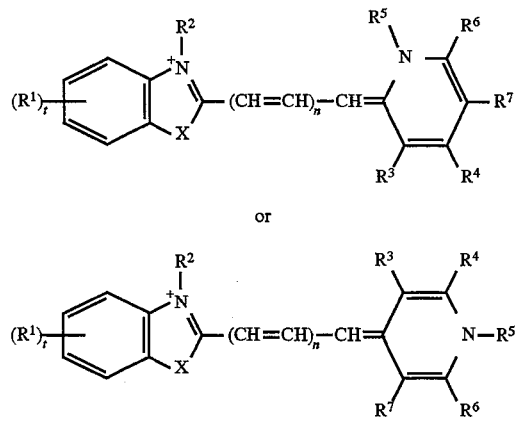

In preferred embodiments of the invention, m=1 and p=0 ("4-pyridiniums" and "4-quinoliniums").

The ring substituents $R^3$ and $R^4$ are independently H, or a halogen, or an alkyl, alkenyl, polyalkenyl, alkynyl or polyalkynyl group having 1–6 carbons. $R^3$ and $R^4$ are also optionally and independently —$OR^8$, —$SR^8$, —($NR^8R^9$), where $R^8$ and $R^9$, which can be the same or different, are independently H, alkyl groups having 1–6 carbons, 1–2 alicyclic or aromatic rings, or $R^8$ and $R^9$ taken in combination are —$(CH_2)_4$— or —$(CH_2)_5$— to give a 5- or 6-membered ring. Additionally, $R^3$ and $R^4$ are optionally and independently —$OSO_2R^{19}$ where $R^{19}$ is alkyl having 1–6 carbons, or perfluoroalkyl having 1–6 carbons, or aryl.

The ring substituents $R^6$ and $R^7$ are optionally any substituent defined for $R^3$ and $R^4$, with the exception of —$OSO_2R^{19}$. Alternatively, $R^6$ and $R^7$ taken in combination are —$(CH_2)_v$— where v=3 or 4, forming a fused 5- or 6-membered ring, or $R^6$ and $R^7$, taken in combination form a fused 6-membered aromatic ring.

Alternatively, any of $R^3$, $R^4$, $R^6$ or $R^7$ could be a cyclic substituent, as defined earlier for $R^5$. Preferred ring substituents are independently H, alkyl, —$OR^8$, or a cyclic substituent, or a TAIL. For all embodiments of the present invention, preferably $R^4$ is not hydrogen. In another embodiment of the invention, $R^4$ is a TAIL.

Where $R^6$ and $R^7$ taken in combination form a fused 6-membered aromatic ring, embodiments of this invention are quinolinium derivatives according to the formula

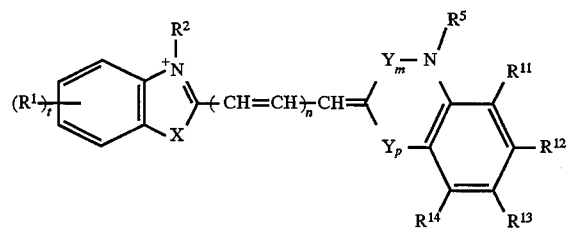

where ring substituents $R^{11}$, $R^{12}$, $R^{13}$, and $R^{14}$ may be the same or different, and are independently H; or an alkyl, alkenyl, polyalkenyl, alkynyl or polyalkynyl group having 1–6 carbons; or a halogen; or —$OR^8$, —$SR^8$, —$(NR^8R^9)$, where $R^8$ and $R^9$ are as defined previously; or a cyclic substituent, as defined for $R^5$; or a TAIL. Preferred embodiment of the invention are quinoliniums wherein m=1 and p=0("4-quinoliniums").

Typically, one or more of $R^3$, $R^4$, $R^5$, $R^6$, $R^7$, $R^{11}$, $R^{12}$, $R^{13}$ and $R^{14}$ is a TAIL. In one embodiment of the invention, at least one of $R^3$, $R^4$, $R^5$, $R^6$, $R^7$, $R^{11}$, $R^{12}$, $R^{13}$ and $R^{14}$ is required to be a TAIL. Preferably, one or more of $R^4$, $R^6$, or $R^{12}$ is TAIL, more preferably, $R^4$ is a TAIL. When $R^4$ is a TAIL, LINK is preferably —$NR^{20}$— or —S—. When TAIL is at any position other than $R^4$ or $R^5$, LINK is preferably —O— or a single bond.

For all embodiments, when the second heterocyclic ring has only one TAIL substituent, and $R^5$ is a TAIL, one of $R^3$, $R^4$, $R^6$, $R^7$, $R^{11}$, $R^{12}$, $R^{13}$ or $R^{14}$ is not hydrogen, preferably $R^4$ is not hydrogen.

In a specific embodiment of the invention, the dyes of the invention are 4-pyridiniums or 4-quinoliniums, wherein $R^5$ is an alkyl having 1–6 carbons, or $R^5$ is a cyclic substituent, and $R^4$ is not hydrogen. Dyes having an $R^4$ substituent that is non-hydrogen possess enhanced quantum yields relative to similar dyes wherein $R^4$ is H. For this class of dyes, $R^5$ is preferably alkyl having 1–6 carbons. Preferably $R^4$ is a TAIL.

In an additional preferred embodiment of the invention, the second heterocyclic ring contains exactly two non-hydrogen substituents, one of which is a TAIL.

Some of the dyes of the present invention that possess a TAIL moiety at $R^4$ exhibit particular utility for staining cells and microorganism. The utility of specific embodiments of the dyes of the present invention in staining cells and microorganisms is generally dependent on the chemical nature of the TAIL moiety, and the identity of the group present at $R^5$. For example, those compounds for which CAP is a quaternary ammonium salt are generally impermeant to living cells, with the exception of some yeast cells. However, the permeability of those compounds for which CAP is a primary or secondary amine, and LINK is a secondary or tertiary amine, are related to the nature of $R^5$ (the N-substituent): Where $R^5$ is an aryl group, the compounds are generally permeant to all cells, living or dead, but the corresponding compounds having an alkyl substituent at $R^5$ are generally impermeant to cellular membranes. A similar relationship to the $R^5$ substituent is observed where TAIL is a nitrogen-containing heterocycle: Where $R^5$ is an aryl group, the compounds are generally permeant to all cells, but when $R^5$ is an alkyl group, the dyes are generally permeant only to mammalian cells.

Typically, dyes useful as impermeant cellular probes are those dyes having 2–3 positive charges, preferably 3 positive charges, more preferably having 2–3 positive charges where $R^5$=alkyl. Preferred dyes for permeant cellular probes are dyes wherein $R^5$ is aryl or heteroaryl and CAP is —O—$R^{21}$ or —S—$R^{21}$. Dyes that are preferred for staining electrophoretic gels typically have CAP that is a dialkylamino group.

The photostability of the dyes of the present invention is also somewhat dependent on the chemical nature of the dye. It is found to be generally true that dyes having a benzoxazolium ring (X=O) are more photostable when illuminated than dyes having a benzothiazolium ring (X=S). Also, dyes having $R^5$=phenyl are generally more photostable than dyes having $R^5$=alkyl.

A list of selected emodiments of the present invention is presented in Tables 3, 4 and 5. While the table includes many preferred embodiments, the dyes shown in the Tables are not intended to be an exclusive list of the dyes of the present invention. Numerous modifications, substitutions, and alterations in substituents and dye structure are possible without departing from the spirit and scope of the invention.

TABLE 3

Specific examples of 4-quinolinium dyes

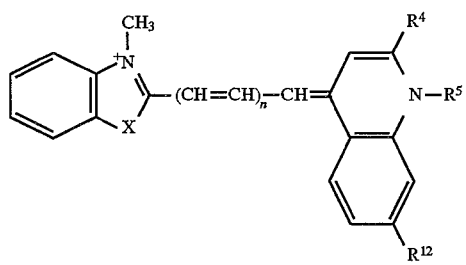

| Dye | X | n | $R^4$ | $R^5$ | $R^{12}$ |
|---|---|---|---|---|---|
| 211 | O | 0 |  | phenyl | H |
| 298 | S | 0 |  | phenyl | —$OCH_3$ |
| 308 | S | 0 |  | phenyl | —$OCH_3$ |

TABLE 3-continued

Specific examples of 4-quinolinium dyes

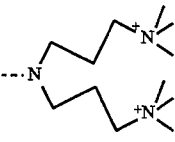

| Dye | X | n | R⁴ | R⁵ | R¹² |
|---|---|---|---|---|---|
| 309 | S | 0 | -N(CH₂CH₂CH₂N⁺(CH₃)₃)₂ | phenyl | —OCH₃ |
| 314 | O | 1 | -S-CH₂CH₂-N(CH₃)₂ | phenyl | H |
| 316 | O | 1 | -S-CH₂CH₂-N⁺(CH₃)₃ | phenyl | H |
| 342 | O | 0 | -N(CH₂CH₂CH₂N(CH₃)₂)₂ | phenyl | H |
| 345 | O | 0 | -N(CH₂CH₂CH₂N⁺(CH₃)₃)₂ | phenyl | H |
| 352 | O | 0 | -S-CH₂CH₂-N(CH₃)₂ | phenyl | H |
| 365 | S | 0 | -S-CH₂CH₂-C(=O)-NH-CH₂CH₂CH₂-N(CH₃)₂ | phenyl | H |
| 374 | S | 0 | n-butyl | phenyl | -O-CH₂CH₂CH₂-N⁺(CH₃)₃ |
| 377 | S | 0 | -N(propyl)-CH₂CH₂CH₂-N(CH₃)₂ | —CH₃ | H |
| 378 | S | 0 | —NEt₂ | —CH₃ | H |
| 379 | S | 0 | -S-C(=NH)-NH-CH₂CH₂CH₂- (cyclic) | phenyl | H |
| 380 | S | 0 | -S-C(=N-N=)-S... -NH-C(=O)-CH₂CH₂CH₂-N(CH₃)₂ | phenyl | H |

TABLE 3-continued

Specific examples of 4-quinolinium dyes

| Dye | X | n | R⁴ | R⁵ | R¹² |
|-----|---|---|----|----|-----|
| 381 | S | 0 | n-butyl | -phenyl-O-(CH₂)₃-N⁺(CH₃)₃ | H |
| 387 | S | 1 | -S-CH₂CH₂-N(CH₃)₂ | phenyl | H |
| 390 | S | 0 | -phenyl-CH₂-N⁺(CH₃)(C₂H₅)₂ | phenyl | H |
| 391 | S | 1 | -S-CH₂CH₂-N⁺(CH₃)₃ | phenyl | H |
| 395 | S | 0 | n-butyl | -C₆H₄-OCH₃ (4-methoxyphenyl) | H |
| 396 | O | 0 | -N[(CH₂)₃N(CH₃)₂]₂ | -CH₃ | H |
| 397 | S | 0 | -N(CH₂CH₂)₂N-CH₃ (4-methylpiperazinyl) | -CH₃ | H |
| 398 | O | 0 | -N[(CH₂)₃N⁺(CH₃)₃]₂ | -CH₃ | H |
| 410 | O | 0 | -N(propyl)(CH₂)₃N(CH₃)₂ | -CH₃ | H |
| 630 | S | 0 | phenyl | phenyl | H |
| 640 | S | 0 | Cl | -CH₃ | H |
| 756 | S | 0 | -S-phenyl | -CH₃ | H |

TABLE 3-continued

Specific examples of 4-quinolinium dyes

| Dye | X | n | R⁴ | R⁵ | R¹² |
|-----|---|---|----|----|-----|
| 856 | S | 0 | —N(piperazine)N—CH₃ | phenyl | H |
| 937 | S | 0 | ⋯N(propyl)-N(CH₃)₂ | phenyl | H |
| 938 | S | 0 | ⋯N(methyl)(propyl-N(CH₃)₂) | phenyl | H |
| 993 | S | 0 | ⋯N(bis(propyl-N(CH₃)₂)) | phenyl | H |
| 996 | S | 0 | ⋯S-CH₂CH₂-N(CH₃)₂ | phenyl | H |
| 1004 | O | 0 | ⋯S-CH₂CH₂-N(CH₃)₂ | phenyl | H |
| 1107 | S | 0 | ⋯N(propyl)(propyl-+N(CH₃)₃) | phenyl | H |
| 1114 | S | 0 | ⋯N(bis(propyl-+N(CH₃)₃)) | phenyl | H |
| 1148 | S | 0 | ⋯NH(CH₂)₃N(CH₃)(CH₂)₃NH₂ | phenyl | H |
| 1151 | S | 0 | —N(piperazine)N⁺(CH₃)₂ | phenyl | H |
| 1155 | S | 0 | ⋯S-CH₂CH₂-+N(CH₃)₃ | phenyl | H |
| 1167 | S | 0 | ⋯S-CH₂CH₂-+N(CH₃)₃ | —CH₃ | H |

TABLE 3-continued

Specific examples of 4-quinolinium dyes

[Structure: benzazolium-CH3 linked via (CH=CH)$_n$—CH= to 4-quinolinium with R$^4$, N—R$^5$, R$^{12}$ substituents; X in benzazole ring]

| Dye | X | n | R$^4$ | R$^5$ | R$^{12}$ |
|---|---|---|---|---|---|
| 1168 | S | 0 | —N(CH$_2$CH$_2$CH$_2$N(CH$_3$)$_2$)$_2$ | —CH$_3$ | H |
| 1169 | S | 0 | —S—CH$_2$CH$_2$—N(CH$_3$)$_2$ | —CH$_3$ | H |
| 1170 | S | 0 | —N(CH$_2$CH$_2$CH$_2$N$^+$(CH$_3$)$_2$)$_2$ | —CH$_3$ | H |
| 1172 | S | 0 | —N(n-propyl)(CH$_2$CH$_2$CH$_2$N$^+$(CH$_3$)$_2$) | —CH$_3$ | H |
| 1174 | S | 0 | —S—P(=S)(OEt)(OEt) | phenyl | H |
| 1189 | S | 0 | —S—C$_6$H$_4$—NH—C(=O)—(CH$_2$)$_3$—N$^+$(pyridinium) | phenyl | H |
| 1199 | S | 0 | —NH—N(CH$_3$)$_2$ | phenyl | H |
| 3102 | S | 0 | —N(piperazinyl-N$^+$(CH$_3$)$_2$) | —CH$_3$ | H |
| 3103 | S | 0 | —OCH$_3$ | —CH$_3$ | H |
| 6101 | S | 0 | n-butyl | —CH$_3$ | H |
| 10101 | S | 0 | —N(CH$_2$CH$_2$CH$_2$N(CH$_3$)$_2$)$_2$ | phenyl | —OCH$_3$ |

TABLE 4

Specific examples of 4-pyridinium dyes

| Dye | X | n | R⁴ | R⁵ | R⁶ |
|---|---|---|---|---|---|
| 322 | O | 0 | | phenyl | H |
| 1182 | S | 0 | —CH₃ | —CH₃ | —CH₃ |
| 3100 | S | 0 | —CH₃ | —CH₃ | H |

TABLE 5

Specific examples of 2-quinolinium dyes

| Dye | X | n | R⁴ | R⁵ | R¹¹ |
|---|---|---|---|---|---|
| 388 | S | 0 | | —CH₃ | H |
| 530 | S | 0 | H | —CH₃ | —OH |
| 515 | O | 1 | —OCH₃ | —CH₃ | H |
| 517 | S | 0 | —OCH₃ | —CH₃ | H |

Synthesis

A useful synthetic route to the dyes of the present invention can be described in three parts, following the natural breakdown in the description of the compounds. In general, the synthesis of these dyes requires three precursors: a benzazolium salt, a pyridinium (or quinolinium) salt (both of which have the appropriate chemical substituents, or can be converted to the appropriate substituents), and (where n=1 or 2) a source for the methine spacer. The combination that enables these compounds to be useful stains for nucleic acids has not been described previously, but the chemistry that is required to prepare and combine these precursors so as to yield any of the subject derivatives is generally well-understood by one skilled in the art. Although there are many possible variations that may yield an equivalent result, we provide herein some useful general methods for their synthesis and incorporation of chemical modifications.

The benzazolium moiety

A wide variety of derivatives of this type for use in preparing photographic dyes have been described, in particular by Brooker and his colleagues (Brooker, et al., J. AM. CHEM. SOC., 64, 199 (1942)). These synthetic precursors have the common structure:

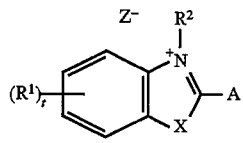

If X is O, the precursor compound is a benzoxazolium; if X is S it is a benzothiazolium; if X is Se it is a benzoselenazolium; if X is N or an alkyl substituted N it is a benzimidazolium; and if X is $CR^{16}R^{17}$ (where $R^{16}$ and $R^{17}$, which may be the same or different, are independently alkyl groups having 1–6 carbons, or $R^{16}$ and $R^{17}$ taken in combination complete a five or six membered saturated ring) then it is an indolinium derivative. Commonly $R^{16}$ and $R^{17}$ are both methyl. However, methods for preparing compounds where $R^{16}$ and $R^{17}$ are not methyl are known. The commercial availability of suitable starting materials and relative ease of synthesis make compounds with X=O or S the preferred intermediates.

$R^1$ is usually incorporated in the parent benzazole molecule prior to quaternization with an alkylating agent. $R^2$ is usually obtained by alkylation of the parent heterocycle with an alkylating agent $R^2$—Z where $R^2$ is an alkyl group having 1–6 carbons and Z is an electronegative group that frequently becomes the counterion on the resultant dye, $\Psi^-$. The counterion may be exchanged for another counterion by methods known in the art, such as the use of ion exchange resins or by precipitation. Examples of $R^2$-Z include methyl iodide, diethyl sulfate, and hexyl-p-toluenesulfonate. Preferred $R^2$—Z are compounds that yield $R^2$=methyl, such as methyl iodide, methyl methanesulfonate, dimethyl sulfate, methyl trifluoromethanesulfonate or methyl p-toluenesulfonate.

A is a substituent whose nature is determined by the synthetic method utilized to couple the benzazolium precursor with the pyridinium or quinolinium precursor. When n=0, A is usually alkylthio, commonly methylthio, or A is chloro, bromo or iodo. When n=1 or 2, A is methyl. Only in the case of A=methyl is any part of A incorporated in the final compound.

The pyridinium or quinolinium moiety

The strongly conjugated ring system of the compounds of the present invention allows resonance stabilization of the single positive charge on the ring atoms to be distributed over the entire molecule. In particular, the charge is stabilized by partial localization on each of the heterocyclic nitrogen atoms of the dye. As the subject dye is drawn herein, the positive charge is formally localized on the benzazolium portion of the dye. However, it is commonly understood that a comparable resonance structure can be drawn in which the positive charge is formally localized on the pyridinium portion of the dye. Consequently, we will usually refer to this latter portion of the molecule as a pyridine, pyridinium, quinoline or quinolinium moiety, although in the resonance structure shown, it would formally be termed a dihydropyridine or dihydroquinoline.

Compounds containing the quinolinium moiety in this invention differ from those that contain a single pyridinium ring only in the presence of an additional aromatic ring containing four carbon atoms that is fused at the $R^6$ and $R^7$ positions of the parent structure. Except where reference is to a specific pyridine or pyridinium salt, it is understood that mention of pyridines or pyridinium salts encompasses benzopyridines and benzopyridinium salts, which are formally called quinolines or quinolinium salts. Mention of quinolines and quinolinium salts refer only to structures containing two fused aromatic rings.

In the synthesis of the dyes of the invention, the second heterocyclic precursor is usually a pyridinium salt that is already appropriately substituted (as in Examples 2, 9, and 11). Alternatively, substituents can be incorporated into the pyridinium structure subsequent to attachment of the benzazolium portion of the dye (Example 5). One of the substituents, which may be incorporated before or after reaction with the benzazolium precursor is TAIL.

Aside from the structural differences between pyridines and quinolines, there exist two major structural distinctions within the family of dyes described in the invention, related to the point of attachment of the pyridinium moiety. In one case (where m=0 and p=1) the position of attachment places the methine bridge adjacent to the ring nitrogen (2-pyridines). In the more common ease (where m=1 and p=0) the position of the nitrogen atom is para to the point of attachment (4-pyridines).

Typically the required pyridinium salt precursor has the structure

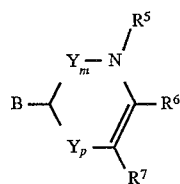

and the quinolinium salt precursor has the general structure

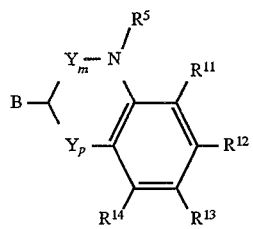

with the substituents as defined previously. At all times, the ring is a 6-membered pyridinium-based heterocycle.

When n=0, B is methyl, or B is chloro, bromo or iodo. When n=1 or 2, B is methyl. Only when n=1 or n=2 is any part of B incorporated in the final compound.

There are several general methods for the synthesis of derivatives of pyridinium, including those derivatives having substituents at any available position, including substitutions that are TAIL or that can be converted to TAIL before or after reaction with the benzazolium portion to form the dye core structure. Substitutions at $R^5$ or at the position immediately adjacent to the nitrogen atom to which $R^5$ is attached (i.e. at $R^4$ when m=1 and p=0) are particularly important.

Method 1. Alkylation of the nitrogen atom of an appropriately substituted quinoline with an alkylating agent such as a primary aliphatic halide, sulfate ester, sulfonate ester, epoxide or similar reagent directly yields a substituted quinolinium salt. For example, treatment of a quinoline with 1,3-diiodopropane and base, followed by heating with trimethylamine, yields a TAIL substituent at $R^5$ (Example 19). If there is a TAIL substituent, or a group that can be converted to a TAIL substituent, at a position other than $R^5$, then simple alkylating agents such as methyl iodide or dimethyl sulfate suffice to add the $R^5$ substituent, where $R^5$ is alkyl.

Method 2. $R^5$ substituents that are aryl or heteroaryl are best incorporated by an Ullmann reaction of aniline or a substituted aniline or of a pyridone or quinolone derivative. In this method, a diaryl amine or aryl-heteroaryl amine (generally commercially available) is condensed with diketene and acid to yield a 4-methyl-N-arylquinolone or a 4-methyl-N-heteroarylquinolone (as in Example 1).

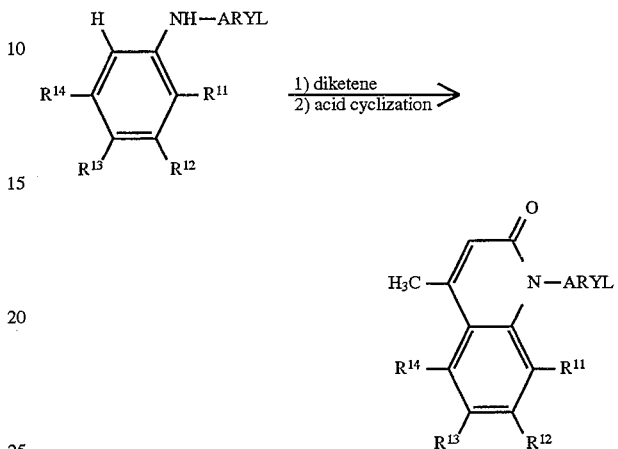

In the above formula, ARYL can be any aromatic or heteroaromatic ring system. Further, $R^{11}$, $R^{12}$, $R^{13}$, $R^{14}$, and substituents on ARYL-X may be a TAIL, or may be substituents that can be readily converted to a TAIL (Example 10).

The 4-methyl-2-quinolone is then converted to the desired 4-methyl-2-substituted-quinolinium salt by reaction with an organometallic reagent such as a Grignard or organolithium reagent (Examples 9 and 10).

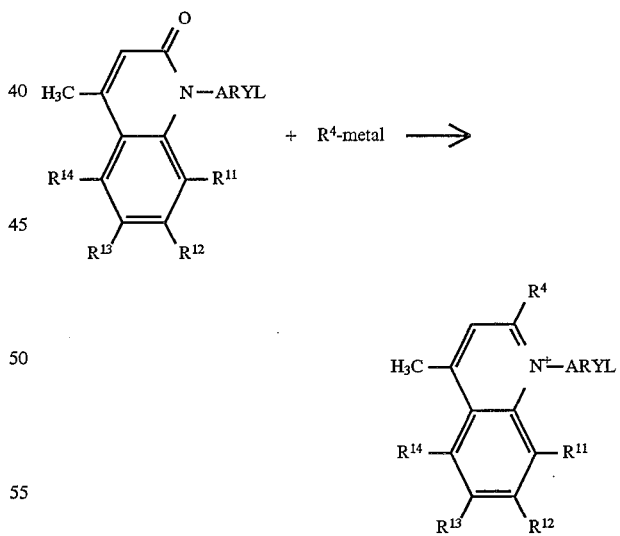

An $R^4$ substituent attached in this way may be aromatic or aliphatic and can be a TAIL or can be converted to TAIL (as in Example 13), provided that the nature of the substituent does not interfere with preparation of the required organometallic reagent.

Pyridone and quinolone precursors may also be prepared by an Ullmann reaction of the appropriately substituted precursor if the nitrogen atom is hydrogen-substituted such as by the following reactions:

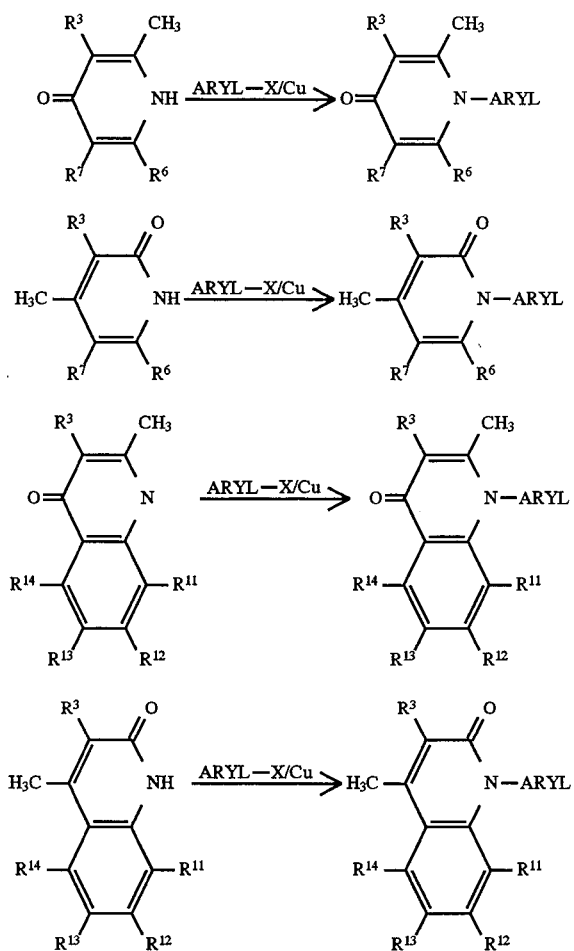

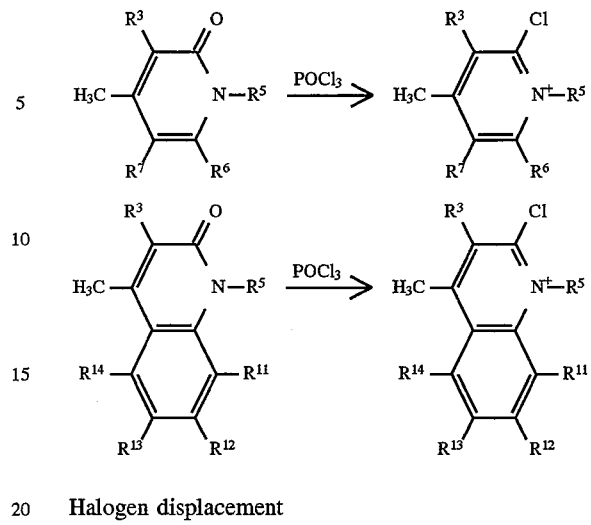

Halogen displacement

The reactivity of the 2-halogenated pyridinium or quinolinium intermediate offers a variety of synthetic methods for attachment of various substituents at the 2-position, including TAILs and TAIL precursors. However, the reactivity of the 2-halo derivatives is preserved even after conjugation with the benzazolium precursor, enabling conversion of the resulting dye in which $R^4$ is halogen into the appropriate alkoxy, amino and thiolate analogs, as described for the pyridinium and quinolinium precursors. Of particular utility for the dyes of the present invention is the displacement of a 2-chloro substituent by amines (yielding TAIL or TAIL precursors where LINK is —$NR^{20}$—), thiols (yielding TAIL or TAIL precursors where LINK is —S—) or alcohols (yielding TAIL or TAIL precursors where LINK is —O—). The displacement of chloride by amines is described in Example 5, and the displacement of chloride by thiols is described in Example 7.

Additionally, the 2-oxo group of pyridone or quinolone precursors can be chemically reduced to derivatives in which $R^4$ is H using a variety of reagents including DIBAL-H (diisobutylaluminum hydride).

The methine bridge

The methine bridge consists of 1, 3 or 5 methine (—CH=) groups that bridge the benzazolium portion of the molecule and the pyridinium portion in such a way as to permit extensive electronic conjugation. The number of methine groups is determined by the specific synthetic reagents used in the synthesis.

When n=0, the synthesis of monomethine dyes commonly uses a combination of reagents where the methine carbon atom results from either A on the benzazolium salt or B on the pyridinium salt being methyl and the other of A or B being a reactive "leaving group" that is typically methylthio or chloro, but which can be any leaving group that provides sufficient reactivity to complete the reaction. This type of reaction to make unsymmetrical monomethine dyes from two quaternary salts was originally described by Brooker et al., supra. Whether A or B is methyl depends primarily on the relative ease of synthesis of the requisite precursor salts. Because the compounds in this invention typically contain the greatest variation on the pyridinium portion of the molecule; and furthermore, because 2-methyl and 4-methyl pyridines are usually easier to prepare than their corresponding methylthio analogs, we have usually chosen to prepare the subject monomethine dyes from precursors in which A=methylthio and B=methyl. Several descriptions of this type of reaction to prepare the subject dyes are given in the While a variety of 4-methyl-2-quinolones are commercially available, desired derivatives can be synthesized by reaction of aniline or a substituted-aniline with an acetoacetate or acetoacetate equivalent reagent such as diketene.

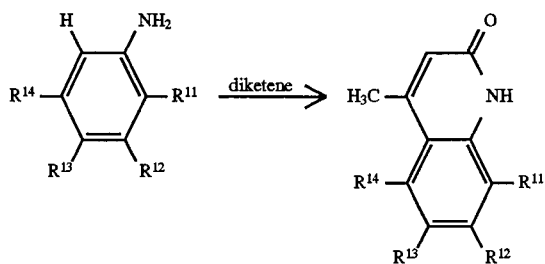

Pyridone and quinolone intermediates containing a non-hydrogen group at $R^5$ are particularly important precursors to a wide variety of other pyridinium and quinolinium salts that are substituted at $R^4$. In particular a salt is formed by treatment of the appropriate pyridone or quinolone with a strong chlorinating agent such as $PCl_5$, $POCl_3$ or $SOCl_2$, for instance in the reaction below (Example 2). Similarly, a sulfonate can be substituted at $R^4$ by treating the pyridone or quinolone with the appropriate sulfonic acid anhydride.

Examples. The condensing reagent in the case of monomethine dyes is typically a weak base such as triethylamine or diisopropylethylamine.

To synthesize trimethine dyes (n=1) both A and B are methyl. In this case the additional methine carbon is provided by a reagent such as diphenylforamidine, N-methylformanilide or ethyl orthoformate. Because under certain reaction conditions these same reagents can yield symmetrical cyanine dyes that incorporate two moles of a single quaternary salt, it is important to use the proper synthetic conditions, and a suitable ratio of the carbon-providing reactant to the first quaternary salt, so that the proper intermediate will be formed. This intermediate is treated either before or after purification with the second quaternary salt to form the asymmetric cyanine dye. If desired, the counterion $\Psi^-$ can be exchanged at this point. Although one can usually react either of the heteroaromatic precursor salts with the carbon-providing reagent to form the required intermediate, we have usually chosen to form the intermediate from the more readily available 2-methylbenzazolium salts as described by Brooker et al. A description of a method to synthesize a trimethine dye is given in Example 8.

Synthesis of the pentamethine dyes (n=2) requires the same synthetic concerns about controlling the formation of an asymmetric intermediate. The three-carbon fragment that is required for the additional atoms in the bridge comes from a suitable precursor to malonaldehyde such as malonaldehyde dianil, 1,1,3,3-tetramethoxypropane, 1,1,3-trimethoxypropene, 3-(N-methylanilino)propenal or other reagents. The condensing agent for this reaction is usually 1-anilino-3-phenylimino-1-propene (U.S. Pat. No. 2,269,234 to Sprague, 1942), which generates the 2-(2-anilinovinyl)-3-methylbenzazolium tosylate intermediate.

TAIL

As described earlier, TAIL is composed of three parts: LINK, SPACER and CAP. If a TAIL is present as $R^5$, then LINK is constrained to be a single bond, eliminating the potential of N—S, N—O or N—N bonds in TAIL. The chemical composition of SPACER is determined by the chemistry required to attach the heteroatom in CAP with the dye core structure via LINK.

As described above, those dyes of the present invention that are 4-pyridiniums or 4-quinoliniums wherein $R^4$ is a TAIL are most conveniently synthesized from the 2-halopyridinium or 2-haloquinolinium precursor either before or after condensation with the benzazolium portion of the dye by a nucleophilic displacement reaction of the halogen by a thiol, alkoxide, or a primary or secondary amine.

CAP may be incorporated directly into TAIL before or after condensation of the pyridinium or quinolinium salt with the benzazolium salt, or CAP may be added or further modified at a later stage in the synthesis. For instance, when CAP is a cyclic or non-cyclic primary, secondary or tertiary amine, CAP can be alkylated to a quaternary ammonium (Examples 6, 7 and 8). This reaction can be used to increase the polarity of the dye and to thus restrict its penetration through the membrane of living cells, and to additionally increase the dye's affinity for nucleic acids.

Precursors to TAIL include carboxylic acids, halides, alcohols and thiols. Each of these reactive groups can be used to attach a heteroatom containing moiety (i.e., CAP) to the dye core structure, generally through the formation of amides (Example 15, 16, 17), ethers or thioethers, which are incorporated into SPACER before (Example 16) or after (Example 17) attachment of SPACER to the dye core structure.

Method of Use

The use of the invention comprises combining a dye of the present invention with a sample that contains or is thought to contain a nucleic acid polymer, incubating the mixture of dye and sample for a time sufficient for the dye to combine with nucleic acid polymers in the sample to form one or more dye-nucleic acid complexes having a detectable fluorescent signal. The characteristics of the dye-nucleic acid complex, including the presence, location, intensity, excitation and emission spectra, fluorescence polarization, fluorescence lifetime, and other physical properties of the fluorescent signal can be used to detect, differentiate, sort, quantitate, and/or analyze aspects or portions of the sample. The dyes of the invention are optionally used in conjunction with one or more additional reagents (preferably detectably different fluorescent reagents), including dyes of the same class having different spectral properties.

Staining Solution

Typically, the subject dye is prepared for use by dissolving the dye in a staining solution, preferably an aqueous or aqueous miscible solution that is compatible with the sample and the intended use. For biological samples, where minimal perturbation of cell morphology or physiology is desired, the staining solution is selected accordingly. For solution assays, the staining solution preferably does not perturb the native conformation of the nucleic acid undergoing evaluation. At pH higher than 8 and lower than 6.5, fluorescence of the dye-nucleic acid complex and stability of the dyes is reduced. High concentrations of organic solvents, cations, and oxidizing agents also generally reduce fluorescence, as does the ionic detergent sodium dodecyl sulfate (SDS) at concentrations >0.01%. A number of staining solution additives, however, do not interfere with the fluorescence of the dye-nucleic acid complex (e.g. urea up to 8M; CsCl up to 1 g/mL; formamide up to 50% of the solution; and sucrose up to 40%). The dyes have greater stability in buffered solutions than in water alone; and agents that reduce the levels of free oxygen radicals, such as β-mercaptoethanol, contribute to the stability of the dyes.

The staining solution is made by dissolving the dye directly in an aqueous solvent such as water, a buffer solution, such as buffered saline (preferably non-phosphate for some viability discrimination applications), a Tris (hydroxymethyl)aminomethane (TRIS) buffer (preferably containing EDTA), or a water-miscible organic solvent such as dimethylsulfoxide (DMSO), dimethylformamide (DMF), or a lower alcohol such as methanol or ethanol. The dye is usually preliminarily dissolved in an organic solvent (preferably 100% DMSO) at a concentration of greater than about 100-times that used in the staining solution, then diluted one or more times with an aqueous solvent such as water or buffer, such that the dye is present in an effective amount.

An effective amount of dye is the amount sufficient to give a detectable fluorescence response in combination with nucleic acids. The dye concentration in the solution must be sufficient both to contact the nucleic acids in the sample and to combine with the nucleic acids in an amount sufficient to give a signal, but too much dye will cause problems with background fluorescence. Typically staining solutions for cellular samples have a dye concentration greater than 0.1 nM and less than 50 μM, more typically greater than 1 nM and less than 10 μM, preferably between 0.5 and 5 μM. In general, lower concentrations of dyes are required for eukaryotes than for prokaryotes, and for dyes with higher sensitivity. Staining solutions for electrophoretic gels typically have a dye concentration of greater than 0.1 μM and less than 10 μM, more typically about 0.5–2 μM; the same holds true where the dye is added to the gel (pre-cast) before being combined with nucleic adds. Staining solutions for detection and quantitation of free nucleic acids in solution typically have a concentration of 0.1 μM–2 μM. The optimal concentration and composition of the staining solution is determined by the nature of the sample (including physical, biological, biochemical and physiological properties), the nature of the dye-sample interaction (including the transport rate of the dye to the site of the nucleic acids), and the nature of the analysis being performed, and can be determined according to standard procedures such as those described in examples below.

Sample Types

The dye is combined with a sample that contains or is thought to contain a nucleic acid. The nucleic acid in the sample may be RNA or DNA, or a mixture or a hybrid thereof. Any DNA is optionally single-, double-, triple-, or quadruple-stranded DNA; any RNA is optionally single stranded ("ss") or double stranded ("ds"). The nucleic acid may be a natural polymer (biological in origin) or a synthetic polymer (modified or prepared artificially). The nucleic acid polymer (preferably containing at least 8 bases or base pairs) may be present as nucleic acid fragments, oligonucleotides, or larger nucleic acid polymers with secondary or tertiary structure. The nucleic acid is optionally present in a condensed phase, such as a chromosome (Examples 28, 29). The nucleic acid polymer optionally contains one or more modified bases or links or contains labels that are non-covalently or covalently attached. For example, the modified base can be a naturally occurring modified base such as ψ (pseudouridine) in tRNA, 5-methylcytosine, 6-methylaminopurine, 6-dimethylaminopurine, 1-methylguanine, 2-methylamino-6-hydroxypurine, 2-dimethylamino-6-hydroxypurine, or other known minor bases (see, e.g. Davidson, THE BIOCHEMISTRY OF THE NUCLEIC ACIDS (1976)) or is synthetically altered to contain an unusual linker such as morpholine derivatized phosphates (AntiVirals, Inc., Corvallis, Oreg.), or peptide nucleic acids such as N-(2-aminoethyl)glycine units (Wittung, et al., Nature 368, 561 (1994)) or contain a simple reactive functional group (<10 carbons) that is an aliphatic amine, carboxylic acid, alcohol, thiol or hydrazine, or contain a fluorescent label or other hapten, such as inosine, bromodeoxyuridine, iododeoxyuridine, biotin, digoxigenin, 2,4-dinitrophenyl, where the label is originally attached on the nucleotide (e.g. CHROMATIDE labeled nucleotides, Molecular Probes, Eugene, Oreg.) or on the 3' or 5' end of the polymer (e.g. ONLY labeled oligonucleotides, Molecular Probes, Eugene, Oreg.), or ligands non-covalently attached to the nucleic acids (e.g. Examples 30, 31). The sensitivity of the dyes for polymers containing primarily modified bases and links may be diminished by interference with the binding mode. Some embodiments of the dyes inhibit non-specific nuclease activity but not restriction endonuclease activity at certain dye:base pair ratios.

The sample that contains the nucleic acid is optionally a biological structure (i.e. an organism or a discrete unit of an organism), or a solution (including solutions that contain biological structures), or a solid or semi-solid material. Consequently, the nucleic acid used to practice the invention is optionally free in solution, immobilized in or on a solid or semi-solid material, extracted from a biological structure (e.g. from lysed cells, tissues, organisms or organelles), or remains enclosed within a biological structure. In order for the nucleic acids to bind to the dyes, it is necessary that the nucleic acids be in an aqueous environment to contact the dye, even if the nucleic acids are not enclosed in a biological structure.

The biological structure that encloses the nucleic acid is optionally a cell or tissue, for example where the nucleic acid is present in a cell or interstitial space as a prokaryote or eukaryote microorganism, or as a virus, viroid, chromosome or organelle. Alternatively, the biological structure is not enclosed in a tissue or cell, and is present either as a virus or as a microorganism or other cell, or is present as a cellular component removed from its parent cell (e.g. a plasmid or chromosome, or a mitochondrion or nucleus or other organelle). Typically, the biological structure is an organelle, chromosome or cell that is optionally inside a eukaryote cell. The cell that is present inside a eukaryote cell is typically a parasite or other infective agent such as a bacterium, protozoa, mycoplasma or mycobacterium. Where the nucleic acid is contained in a biological structure that is a cell, the cells are viable or dead cells or a mixture thereof, i.e. the integrity of the cell membrane is optionally intact or disrupted by natural (autolyric), mechanical or chemical means or by environmental means such as changes in temperature or pressure. Alternatively, the cells are blebbing or undergoing apoptosis or in a cycle of growth or cell division.

Cell types for which the dye is an effective nucleic acid stain include cells with or without nuclei, including but not limited to, eukaryotes, such as plant and animal cells (particularly vertebrate cells), including pollen and gamete cells; prokaryotes, particularly bacteria, including both Gram-negative and Gram-positive bacteria; as well as yeast and other fungi, and spores. The dyes are not equally effective in staining all cell types and certain dyes are generally more permeant than others. Live cells are less permeable to the dyes than dead cells, and prokaryotes are less permeable than eukaryotes (see Table 6).

| | Bacteria | | Yeast | | Eukoryotes | | | | | Fixed/ | |
| | | | | | | Cyto | Live | | Dead | | Permeabilized | |
| Dye | Live | Killed | DNA | Mitoch | Bkg | Nucl | Cyto | Nucl | Cyto | Nucl | Cyto |
|---|---|---|---|---|---|---|---|---|---|---|---|
| 298 | 2 | 2 | | 3 | 0 | 3 | 2 | 2–3 | 1–2 | 2–3 | 1 |
| 308 | | 2 | 3 | 3 | 2 | 0 | 1 | 2 | 1 | 3 | 1 |
| 309 | | 2 | 3 | | 2 | 0 | 1 | 3 | 1–2 | 3 | 0–1 |
| 314 | 3 | 3 | | 1 | 1 | 0–1 | 1 | 1 | 0 | 1 | 0 |
| 316 | | 2 | | 2* | 0 | 0 | 1 | 1 | 0–1 | 1 | 0 |
| 322 | | * | | 1 | 2 | 0 | 1 | 1–2 | 0 | 1 | 0 |
| 342 | | * | | 1 | 1 | 0 | 1 | 3 | 1–2 | 1–2 | 0 |

-continued

| | Bacteria | | | Yeast | | Eukoryotes | | | | |
| | | | | | Cyto | Live | | Dead | | Fixed/Permeabilized | |
| Dye | Live | Killed | DNA | Mitoch | Bkg | Nucl | Cyto | Nucl | Cyto | Nucl | Cyto |
|---|---|---|---|---|---|---|---|---|---|---|---|
| 345 | | 3 | | 2 | 3 | 1 | 2 | 3 | 2 | 3 | 0–1 |
| 352 | | 3 | | 4 | 1 | 0 | 1 | 3 | 1–2 | 3 | 1–2 |
| 365 | | 3 | 2 | 2 | 2 | 0–1 | 2 | 4 | 3 | 4 | 2–3 |
| 372 | 2 | 2 | 2 | | 3 | 1 | 2 | 2 | 0 | 1 | 0 |
| 374 | | 3 | | 2 | 0 | 0 | 0–1 | 3–4 | 2–3 | 3 | 0–1 |
| 377 | | 2 | | 2 | 0 | 1 | 0–1 | 1–2 | 0–1 | 2–3 | 0 |
| 378 | 2 | 2 | | 2 | 0 | 1–2 | 1–2 | 1–2 | 0–1 | 1–2 | 0 |
| 379 | | 1 | | 1 | 0 | 0 | 1 | 1–2 | 0 | 1 | 0 |
| 380 | | 1 | | 1 | 1 | 0 | 0–1 | 2–3 | 2–3 | 1–2 | 1 |
| 381 | | 2 | 3 | | 2 | 1 | 1–2 | 4 | 3 | 4 | 2 |
| 388 | 2 | 2 | | 2 | 3 | 2 | 1 | 4 | 3 | 4 | 1 |
| 390 | | 2 | | 2 | 0 | 0 | 1 | 4 | 1 | 4 | 0 |
| 396 | | 4 | | 3 | 0 | 1 | 2 | 4 | 3 | 2 | 0 |
| 397 | | 3 | | 3 | 0 | 2 | 2 | 4 | 3 | 4 | 0 |
| 398 | | 4 | | | 0 | 0 | 1 | 3 | 2 | 2 | 0 |
| 399 | 3 | 3 | | 2 | 1 | 4 | 4 | 4 | 3 | 3 | 0 |
| 515 | 2 | 2 | | 1 | 0 | 0–1 | 1 | 2 | 1 | 2–3 | 1–2 |
| 517 | | 1 | | 1 | 0 | 2 | 2 | 1 | 2 | 1 | 1 |
| 530 | 2 | 2 | | | 1 | 3 | 3 | 2 | 2 | 1 | 0 |
| 993 | 3 | 3* | 2 | 2 | 1 | 0–1 | 2 | 3–4 | 2 | 3 | 0–1 |
| 996 | 3 | 3 | | 2 | 2 | 4 | 3 | 3 | 2 | 4 | 0–1 |
| 1004 | | | | | | 4 | 3–4 | 4 | 4 | 4 | 3–4 |
| 1107 | | 2 | | 3 | 0 | 0–1 | 1 | 2–3 | 1 | 2–3 | 1 |
| 1114 | | 3 | 2 | 2 | 2 | 0 | 1 | 4 | 2 | 4 | 0–1 |
| 1148 | 2 | 2 | | 2 | 3 | 2 | 2 | 2 | 1 | 2 | 0 |
| 1151 | | 3 | 2 | 2 | 3 | 0 | 0–1 | 4 | 3 | 4 | 3 |
| 1155 | | 2 | | 2 | 0 | 0–1 | 2 | 3 | 1 | 3 | 0 |
| 1167 | | 3 | | 1 | 0 | 0 | 1 | 3 | 2 | 3 | 0 |
| 1168 | | 3 | | 2 | 3 | 0 | 1 | 2–3 | 1–2 | 2–3 | 0 |
| 1169 | | 3 | | 1 | 3 | 1 | 1–2 | 4 | 3 | 4 | 0–1 |
| 1170 | | 3 | 2 | | 3 | 0 | 1 | 2 | 1 | 2–3 | 0 |
| 1172 | | 4 | | 4 | 0 | 0–1 | 1 | 2–3 | 0–1 | 2 | 0 |
| 1174 | 4 | 4 | | 3 | 2 | | | | | | |
| 1178 | | 1 | | | 0 | 0 | 1 | 1 | 2 | 1 | 0 |
| 1182 | 1 | 1 | | 1 | 0 | 0 | 1 | 0–1 | 1 | 1 | 0 |
| 1184 | 2 | 2 | | 2 | 3 | 2 | 2 | 2 | 1 | 2 | 0 |
| 1189 | | 1 | | 1 | 0 | 0–1 | 1 | 4 | 3 | 4 | 4 |
| 3100 | 2 | 2 | | 1 | 0 | 0–1 | 1 | 1 | 0–1 | 1 | 0 |
| 3102 | | 4 | 3 | 3 | 2 | 0 | 1 | 4 | 3 | 4 | 3 |
| 3103 | 4 | 4 | | 3 | 2 | 3 | 3 | 4 | 2–3 | 4 | 3 |
| 10101 | | 3 | 3 | | 3 | 0 | 0–1 | 3 | 2 | 2–3 | 0 |

KEY
Scale of brightness, 1 = dim, 4 = bright
Killed - 70% Isopropanol killed, Dead - 3.7% formaldehyde killed, Fixed/Permeabilized - Dead, then acetone fixed
DNA - Stains DNA spot on Yeast
Mitoch - Stains mitochondria, either spotty or whole
Cyto Bkg - Cytoplasmic background, 0 = no background, 4 = high background The nucleic acids in the sample, both natural and synthetic, may be obtained from a wide variety of sources. The presence of the nucleic acid in the sample may be due to natural biological processes, or the result era successful or unsuccessful synthesis or experimental methodology, undesirable contamination, or a disease state. The nucleic acid may be endogenous to the natural source or introduced as foreign material, such as by infection, transfection, or therapeutic treatment. Nucleic acids may be present in all, or only part, of a sample, and the presence of nucleic acids may be used to distinguish between individual samples, or to differentiate a portion or region within a single sample, or to identify the sample or characteristics of the sample.

Typically, the sample containing nucleic acids is a cell or is an aqueous or aqueous miscible solution that is obtained directly from a liquid source or as a wash from a solid material (organic or inorganic) or a growth medium in which cells have been introduced for culturing or a buffer solution in which nucleic acids or biological structures have been placed for evaluation. Where the nucleic acids are in cells, the cells are optionally single cells, including microorganisms, or multiple cells associated with other cells in two or three dimensional layers, including multicellular organisms, embryos, tissues, biopsies, filaments, biofilms, etc. Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids (Example 50). Alternatively, the sample is obtained from an environmental source such as soil, water, or air; or from an industrial source such as taken from a waste stream, a water source, a supply line, or a production lot. Industrial sources also include fermentation media, such as from a biological reactor or food fermentation process such as brewing; or foodstuffs, such as meat, gain, produce, or dairy products (Examples 45, 46).

Where the nucleic acid is present in a solution, the sample solution can vary from one of purified or synthetic nucleic acids such as oligonucleotides to crude mixtures such as cell extracts or homogenates or other biological fluids, or dilute solutions from biological, industrial, or environmental sources. In some cases it is desirable to separate the nucleic acids from a mixture of biomolecules or fluids in the solution prior to combination with the dye. Numerous techniques exist for separation and purification of nucleic acids from generally crude mixtures with other proteins or other biological molecules. These include such means as chromatographic techniques and electrophoretic techniques, using a variety of supports or solutions or in a flowing stream. Alternatively, mixtures of nucleic acids may be treated with RNase or DNase so that the polymer that is not degraded in the presence of the nuclease can be discriminated from degradation products using the subject dyes.

The source and type of sample, as well as the use of the dye, will determine which dye characteristics, and thus which dyes, will be most useful for staining a particular sample. For most applications, dyes are selected to give a quantum yield greater than about 0.3, preferably greater than 0.6, when bound to nucleic acid; preferably the dyes have a quantum yield <0.01 when not bound to nucleic acid, and a fluorescence enhancement greater than about 200 fold, preferably greater than 1000 fold. Where the fluorescence of the dye-nucleic acid complex is detected utilizing sustained high intensity illumination (e.g. microscopy), dyes with rate of photobleaching lower than commonly used dyes (e.g. fluorescein) are preferred, particularly for use in live cells. The relatively low toxicity of the dyes to living systems generally enables the examination of nucleic acids in living samples with little or no perturbation caused by the dye itself. Where the dye must penetrate cell membranes or a gel, more permeant dyes are preferred, although some cells readily take up dyes that are shown to be impermeant to other cells by means other than passive diffusion across cell-membranes, e.g. by phagocytosis or other types of ingestion. Dyes that rapidly and readily penetrate cells do not necessarily rapidly penetrate gels. In applications where the nucleic acids are stained on a gel, the dye is also selected to have a high binding affinity (preferably $K_d > 10^{-6}$M); whereas in applications where the nucleic acid will be prestained prior to undergoing a separation step, such as gel or capillary electrophoresis, even higher binding affinity (preferably $K_d > 10^{-8}$M) is preferred to ensure good separation. In staining nucleic acids in solution, high binding affinity translates into greater sensitivity to small amounts of nucleic acid, but dyes with a moderate binding affinity (preferably $10^{-6}$M$<K_d<10^{-8}$M) are more effective over a greater dynamic range. The photostability, toxicity, binding affinity, quantum yield, and fluorescence enhancement of dyes are determined according to standard methods known in the art.

Formation of Dye-Nucleic Acid Complex

The sample is combined with the staining solution by any means that facilitates contact between the dye and the nucleic acid. Typically the contact occurs through simple mixing, as in the case where the sample is a solution. A staining solution containing the dye may be added to the nucleic acid solution directly or may contact the nucleic acid solution in a liquid separation medium such as an electrophoretic liquid, sieving matrix or running buffer, or in a sedimentation (e.g. sucrose) or buoyant density gradient (e.g. containing CsCl), or on an inert matrix such as a blot or gel, a testing strip, or any other solid or semi-solid support. Suitable supports also include, but are not limited to, polymeric microparticles (including paramagnetic microparticles), polyacrylamide and agarose gels, nitrocellulose filters, computer chips (such as silicon chips for photolithography), natural and synthetic membranes, liposomes and alginate hydrogels, and glass (including optical filters), and other silica-based and plastic support. The dye is optionally combined with the nucleic acid solution prior to undergoing gel or capillary electrophoresis, gradient centrifugation, or other separation step, during separation, or after the nucleic acids undergo separation. Alternatively, the dye is combined with an inert matrix or solution in a capillary prior to addition of the nucleic acid solution, as in pre-cast gels, capillary electrophoresis or preformed density or sedimentation gradients.

Where the nucleic acids are enclosed in a biological structure, the sample is typically incubated with the dye. While permeant dyes of this class have shown an ability to permeate biological structures rapidly and completely upon addition of the dye solution, any other technique that is suitable for transporting the dye into the biological structure is also a valid method of combining the sample with the subject dye. Some cells actively transport the dyes across cell membranes (e.g. endocytosis or ingestion by an organism or other uptake mechanism) regardless of their cell membrane permeability. Suitable artificial means for transporting the dyes (or pre-formed dye-nucleic acid complexes) across cell membranes include, but are not limited to, action of chemical agents such as detergents, enzymes or adenosine triphosphate; receptor- or transport protein-mediated uptake; liposomes or alginate hydrogels; phagocytosis; pore-forming proteins; microinjection; electroporation; hypoosmotic shock; or minimal physical disruption such as scrape loading, patch clamp methods, or bombardment with solid particles coated with or in the presence of the dyes. Preferably, where intact structures are desired, the methods for staining cause minimal disruption of the viability of the cell and integrity of cell or intercellular membranes. Alternatively, the cells are fixed and treated with routine histochemical or cytochemical procedures, particularly where pathogenic organisms are suspected to be present. The cells are typically fixed immediately after staining with an aldehyde fixative that keeps the dye in the cells. In some cases, live or dead cells may even be fixed prior to staining without substantially increasing cell membrane permeability of previously live cells so that only cells that were already dead prior to fixation stain with the cell-impermeant dye (Example 54).

The sample is combined with the dye for a time sufficient to form the fluorescent nucleic acid-dye complex, preferably the minimum time required to give a high signal-to-background ratio. Although all of the novel class of dyes are nucleic acid stains, detectable fluorescence within biological structures or in gels requires entry of the dye across the biological membrane or into gels. Optimal staining with a particular dye is dependent upon the physical and chemical nature of the individual sample and the sample medium, as well as the property being assessed. The optimal time is usually the minimum time required for the dye, in the concentration being used, to achieve the highest target-specific signal while avoiding degradation of the sample over time and minimizing all other fluorescent signals due to the dye. For example, where the dye is chosen to be selective for a particular nucleic acid polymer or type of cell, the optimal time is usually the minimum time required to achieve the highest signal on that polymer or type of cell, with little to no signal from other nucleic acids or other cell types. Over time, undesirable staining may occur as even very low rates of diffusion transport small amounts of the very sensitive dyes into other cell types, or as the cell membranes degrade, or as nucleases degrade nucleic acid polymers in cell free systems.

Preferably, the dye is combined with the sample at a temperature optimal for biological activity of the nucleic acids within the operating parameters of the dyes (usually between 5° C. and 50° C., with reduced stability of the dyes at higher temperatures). For in vitro assays, the dye is typically combined with the sample at about room temperature (23° C.). At room temperature, detectable fluorescence in a solution of nucleic acids is essentially instantaneous depending on the sensitivity of the instrumentation that is used; fluorescence in solutions is generally visible by eye within 5 seconds after the dye is added, and is generally measurable within 2 to 5 minutes, although reaching equilibrium staining may take longer. Where a biological process is underway during in vitro analysis (e.g. in vitro transcription, replication, splicing, or recombination), the rapid labeling that occurs with the subject dyes avoids perturbation of biological system that is being observed. Gel staining at room temperature usually takes from 5 minutes to 2 hours depending on the thickness of the gel and the percentage of agarose or polyacrylamide, as well as the degree of cross-linking. Typically, post-stained minigels stain to equilibrium in 20–30 minutes. For cells and other biological structures, transport of dyes across membranes is required whether the membranes are intact or disrupted. For preferred embodiments, visibly detectable fluorescence is obtained at room temperature within 15–20 minutes of incubation with cells, commonly within about 5 minutes. Some embodiments give detectable fluorescence inside cells in less than about 2 minutes. Lymphocytes loaded with 5 μM dye solutions give a fluorescence response in less than 5 seconds. This property is useful for observing nuclear structure and rearrangement, for example such as occurs during mitosis or apoptosis. Some of the dyes are generally not permeant to live cells with intact membranes; other dyes are generally permeant to eukaryotes but not to prokaryotes; still other dyes are only permeant to cells in which the cell membrane integrity has been disrupted (e.g. some dead cells). The relative permeability of the cell membrane to the dyes is determined empirically, e.g. by comparison with staining profiles or staining patterns of killed cells. The dye with the desired degree of permeability, and a high absorbance and quantum yield when bound to nucleic adds, is selected to be combined with the sample.

Fluorescence of the Dye-Nucleic Acid Complex

The nucleic acid-dye complex formed during the staining of the sample with a dye of the present invention comprises a nucleic acid polymer non-covalently bound to one or more molecules of dye. The combination of dye and nucleic acid results in a fluorescent signal that is significantly enhanced over the fluorescence of the dye alone. Typically, fluorescence of the dye-nucleic acid complex decreases at pH lower than 6.5 or greater than 8, but can be restored by returning to moderate pH.

Because the fluorescence for most of this class of dyes in solution is extremely low, the absolute degree of enhancement is difficult to determine. The quantum yield of unbound dye is typically <0.01, usually <0.002, and frequently <0.001, which would yield a maximum enhancement of >100x, >500x, and >1000x respectively. The l of fluorescence enhancement of the bound dye is generally about 100–1000 fold greater than that of unbound dye, typically greater than about 300-fold, such that the dyes have a readily detectable increase in quantum yield upon binding to nucleic acids. The molar absorptivity (extinction coefficient) at the longest wavelength absorption peak of the dyes is typically >50,000 and frequently >60,000 for the dyes where n=0; for dyes where n=1 or 2, the molar absorptivity is typically greater than 90,000. Dyes with high extinction coefficients at the excitation wavelength are preferred for the highest sensitivity. A useful level of quantum yield in combination with other attributes of the subject dyes, including selectivity for rate of permeation, for binding affinity and/or the selectivity of excitation and emission bands to suit specific instrumentation, make the dyes useful for a very wide range of applications.

The presence, location, and distribution of nucleic acid is detected using the spectral properties of the fluorescent dye-nucleic acid complex. Spectral properties means any parameter that may be used to characterize the excitation or emission of the dye-nucleic acid complex including absorption and emission wavelengths, fluorescence polarization, fluorescence lifetime, fluorescence intensity, quantum yield, and fluorescence enhancement. Typically the spectral properties of excitation and emission wavelength are used to detect the dye-nucleic acid complex. The wavelengths of the excitation and emission bands of the dyes vary with dye composition to encompass a wide range of illumination and detection bands (Table 7). This allows the selection of individual dyes for use with a specific excitation source or detection filter. In particular, complexes formed with dyes having a monomethine bridge (n=0) generally match their primary excitation band with the commonly used argon laser (488 nm) or HeCd laser (442 nm); whereas those with dyes with a trimethine bridge (n=1) primarily tend to match long wavelength excitation sources such as green HeNe (543 nm), the orange HeNe laser (594 nm), the red HeNe laser (633 nm), mercury arc (546 nm), or the Kr laser (568 or 647 nm); and complexes formed with dyes having a pentamethine bridge (n=2) primarily match very long excitation sources such as laser diodes or light emitting diodes (LEDs). In addition to the primary excitation peak in the visible range, the dye-nucleic acid complexes of the invention have a secondary absorption peak that permits excitation with UV illumination (FIG. 1). Dyes with n=1 and n=2 form complexes that permit excitation beyond 600 nm.

TABLE 7

Quantum Yields of Indicated Nucleic Acid/Dye Complexes

| DYE | Ex./Em. | ds DNA | RNA | ss DNA | oligos |
|---|---|---|---|---|---|
| ethidium bromide | 526/605 | 0.16 | 0.07 | | |
| thiazole orange | 509/525 | 0.20 | | | |
| TOTO-1 | 514/530 | 0.40 | | 0.12 | |
| TO-PRO-1 | 515/530 | 0.19 | 0.16 | | |
| 224 | 470/496 | 0.85 | 0.73 | 0.70 | 0.74 |
| 309 | 496/518 | 0.69 | 0.53 | 0.44 | |
| 314 | 618/634 | 0.16 | 0.18 | | |
| 316 | 617/634 | 0.16 | 0.17 | | |
| 345 | 479/500 | 0.90 | 0.79 | 0.64 | 0.75 |
| 352 | 488/507 | 0.23 | 0.31 | | |
| 377 | 492/521 | 0.70 | 0.47 | | |
| 378 | 485/516 | 0.63 | 0.46 | | |
| 379 | 527/570 | 0.10 | 0.12 | | |
| 381 | 506/527 | 0.37 | 0.33 | | |
| 388 | 519/555 | 0.13 | 0.20 | | |
| 396 | 472/499 | 0.84 | 0.87 | 0.72 | 0.82 |
| 398 | 475/499 | 0.87 | 0.77 | 0.86 | 0.83 |
| 410 | 470/496 | 0.92 | 0.87 | 0.75 | 0.80 |
| 6101 | 504/524 | 0.39 | 0.39 | 0.21 | 0.31 |
| 756 | 513/539 | 0.17 | | | |
| 937 | 494/521 | 0.73 | | 0.39 | |
| 993 | 500/523 | 0.57 | 0.53 | | |

TABLE 7-continued

Quantum Yields of Indicated Nucleic Acid/Dye Complexes

| DYE | Ex./Em. | ds DNA | RNA | ss DNA | oligos |
|---|---|---|---|---|---|
| 996 | 511/532 | 0.16 | 0.22 | | |
| 1004 | 492/513 | 0.36 | 0.54 | | |
| 1107 | 494/522 | 0.67 | | | |
| 1114 | 502/523 | 0.53 | 0.37 | | |
| 1120 | 498/521 | 0.22 | 0.20 | 0.09 | 0.12 |
| 1155 | 511/539 | 0.11 | 0.13 | | |
| 1167 | 509/551 | 0.08 | 0.11 | | |
| 1168 | 498/523 | 0.62 | 0.48 | | |
| 1169 | 508/541 | 0/09 | 0.13 | | |
| 1170 | 498/522 | 0.57 | 0.46 | | |
| 1172 | 492/520 | 0.66 | 0.46 | | |

Fluorescence properties of dyes. Quantum yields of selected dyes bound to double-stranded calf thymus DNA (ds DNA), E. coli ribosomal RNA, single-stranded M13 phage DNA (ss DNA) and oligonucleotides (a synthetic 24 mer). Fluorescence excitation and emission maxima on double-stranded DNA are indicated; units are nm.

Typically, the sample is excited by a light source capable of producing light at or near the wavelength of maximum absorption of the fluorescent complex, such as an ultraviolet or visible wavelength emission lamp, an arc lamp, a laser, or even sunlight or ordinary roomlight. Preferably the sample is excited with a wavelength within 20 nm of the maximum absorption of the fluorescent complex. Although excitation by a source more appropriate to the maximum absorption band of the nucleic acid-dye complex results in higher sensitivity, the equipment commonly available for excitation of samples can be used to excite the dyes of the present invention.

The fluorescence of the complex is detected qualitatively or quantitatively by detection of the resultant light emission at a wavelength of greater than about 450 nm, preferably greater than about 480 nm, more preferably at greater than about 500 nm. Dyes having a quinolinium ring system usually absorb and emit at longer wavelength maxima than similarly substituted dyes having a pyridinium ring system. The emission is detected by means that include visual inspection, CCD cameras, video cameras, photographic film, or the use of current instrumentation such as laser scanning devices, fluorometers, photodiodes, quantum counters, plate readers, epifluorescence microscopes, scanning microscopes, confocal microscopes, flow cytometers, capillary electrophoresis detectors, or by means for amplifying the signal such as a photomultiplier tube. Many such instruments are capable of utilizing the fluorescent signal to sort and quantitate cells or quantitate the nucleic acids. Dyes can be selected to have emission bands that match commercially available filter sets such as that for fluorescein or for detecting multiple fluorophores with several excitation and emission bands.

Use of Complex

Figure 3:
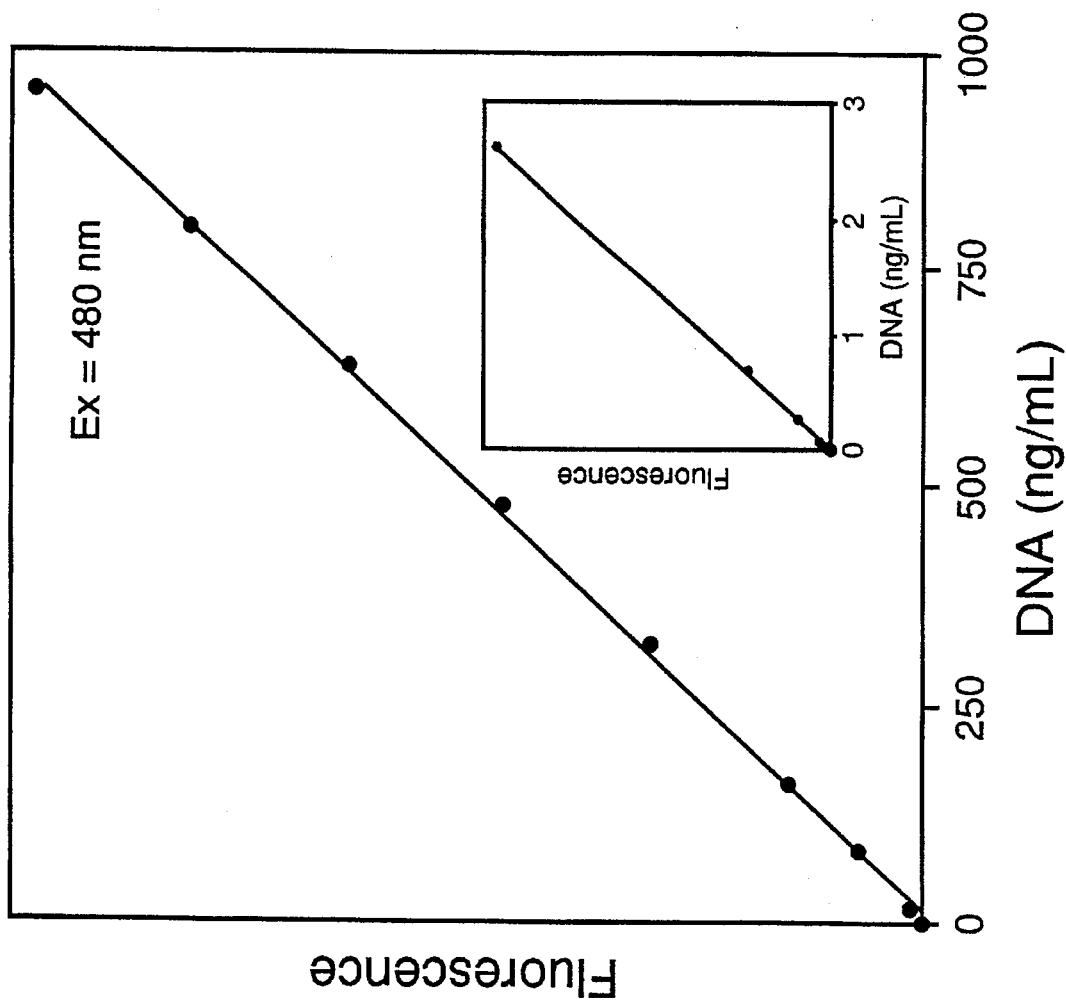
FIG. 3: Linear fluorescence response as a function of DNA concentration, as described in Example 23. The assay is linear from 25 pg/mL (see inset) to 1000mg/mL.
Figure 4:
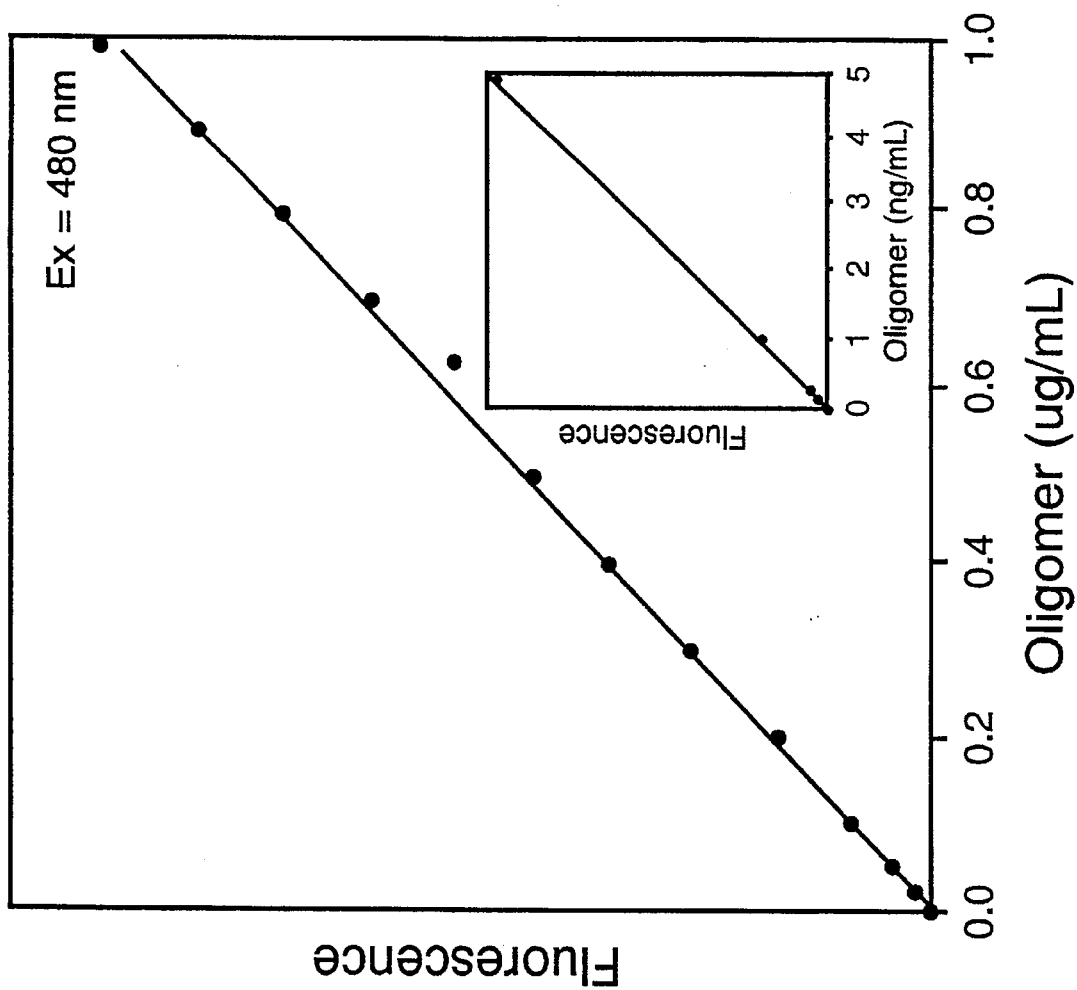
FIG. 4: Linear fluorescence response as a function of oligonucleotide concentration, as described in Example 24. The assay is linear from an oligonucleotide concentration of 100 pg/mL (see inset) to 1 µg/mL

Once the dye-nucleic acid complex is formed, its presence may be detected and used as an indicator of the presence, location, or type of nucleic acids in the sample, or as a basis for sorting cells, or as a key to characterizing the sample or cells in the sample. Such characterization may be enhanced by the use of additional reagents, including fluorescent reagents. The nucleic acid concentration in a sample can also be quantified by comparison with known relationships between the fluorescence of the nucleic acid-dye complex and concentration of nucleic acids in the sample (Examples 23, 24 and 41; FIGS. 3, 4 and 5).

Figure 2:
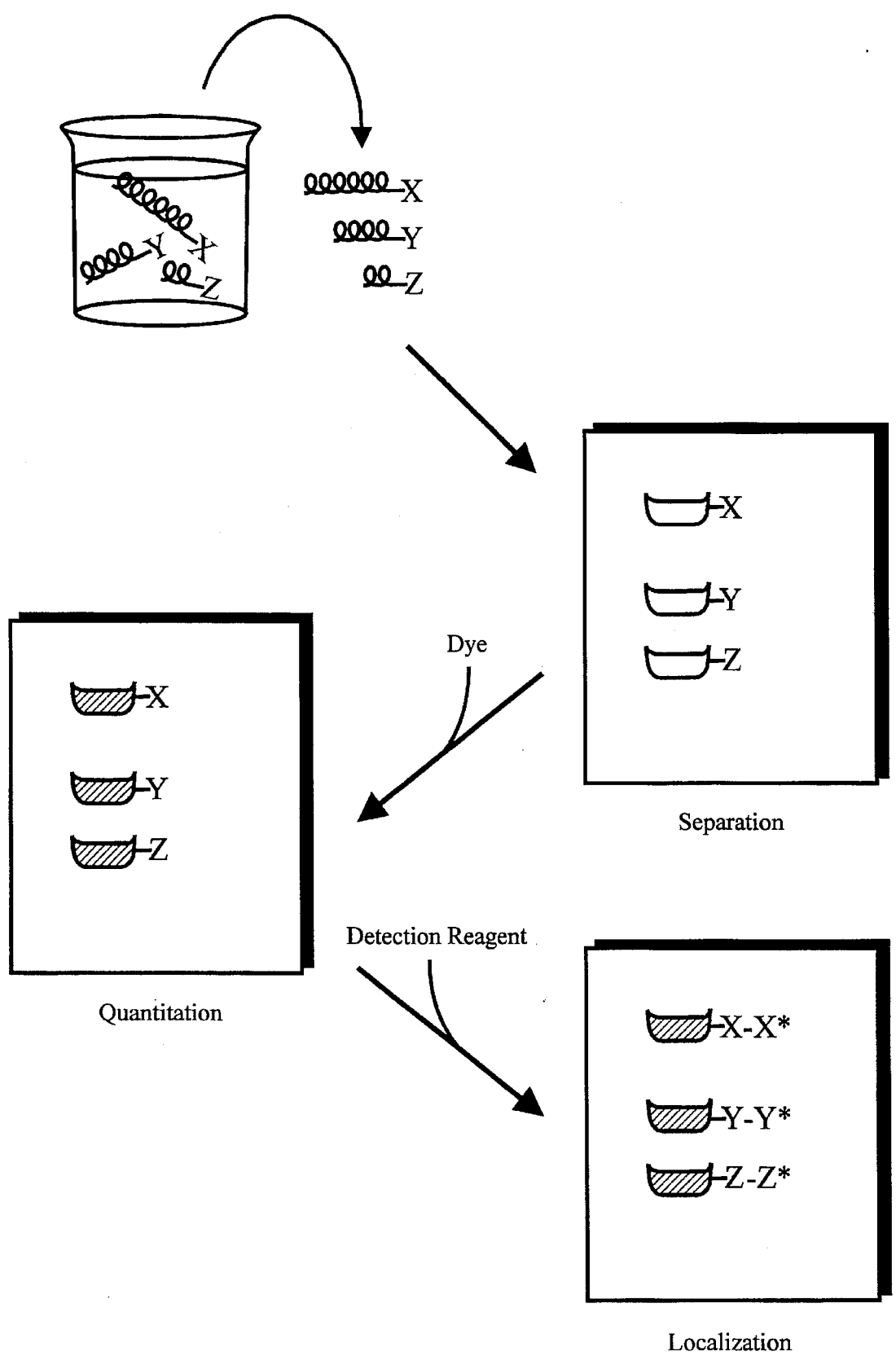
FIG. 2: A multiple labeling experiment using the dyes of the present invention. Nucleic acid polymers are generated that are labeled with a detection reagent that is a fluorophore, avidin, streptavidin or other hapten (X, Y, and Z). After separation, the resulting bands are visualized and quantitated by staining with a dye of the present invention. The bands can be individually identified by treatment with the appropriate reagent, such as biotin, or an antibody (X*, Y* or Z*). This technique is generally described in Example 36.

In one aspect of the invention, the dye-nucleic acid complex is used as a means for detecting the presence or location of nucleic acids in a sample, where the sample is stained with the dye as described above, and the presence and location of a fluorescent signal indicates the presence of nucleic acids at the corresponding location. The fluorescent signal is detected by eye or by the instrumentation described above. The general presence or location of nucleic acids is typically detected in a static liquid solution, or in a flowing stream such as a flow cytometer, or in a centrifugation gradient, or in a separation medium, such as a gel or electrophoretic fluid, or when leaving the separation medium, or affixed to a solid or semisolid support. Alternatively, the dye is selective for a particular type of nucleic acid, and the presence or location of particular nucleic acids are selectively detected. Attachment of covalent labels to the polymers used to form the dye-nucleic acid complex does not prevent subsequent formation of the fluorescent complex (FIG. 2; Example 36).

Nucleic acid polymers are detected with high sensitivity in a wide variety of solutions and separation media, including electrophoretic gels such as acrylamide and agarose gels, both denaturing and non-denaturing, and in other electrophoretic fluids, such as in capillary electrophoresis. The dyes of the invention give a strong fluorescent signal with small nucleic acid polymers (as few as 8 bases or base pairs with some embodiments) even with very small amounts of nucleic acids. Using a fluorescence microscope, a single nucleic acid molecule can be detected (Example 40). Nucleic acid content from as few as 5 mammalian cells can be detected in cell extracts (Example 41). As little as picograms of ds DNA/mL of solution is detected in a fluorometer (Example 23). In conjunction with an ultraviolet transilluminator, it is possible to detect as little as 10 picograms of ds DNA per band in an electrophoretic gel (Example 21); some dyes give such a bright signal even with illumination by ordinary fluorescent room lights, that as little as 1 ng DNA per band is detected. When used for pre- or post-staining of electrophoresis gels, the high sensitivity of the dyes of the present invention allows the detection of previously unmeasurable amounts of nucleic acids using inexpensive instrumentation (e.g. UV trans- and epi-illuminators) without requiring destaining (see Table 8).

TABLE 8

Sensitivity of nucleic acid detection in electrophoretic gels

| Dye Name | DNA (254 nm) | DNA (300 nm) | RNA (254 nm) | RNA (300 nm) |
|---|---|---|---|---|
| ethidium bromide | | 500 pg | | 1.5 ng |
| thiazole orange | 1–2 ng | | | |
| oxazole yellow | 300–600 pg | | | |
| 395 | 20–30 pg | 90–100 pg | 300 pg | 2 ng |
| 630 | 30–40 pg | 90–100 pg | 300–400 pg | 1–2 ng |
| YO-PRO-I | 60 pg | 180–200 pg | 100–200 pg | 580 pg |
| 211 | 20 pg | 150–200 pg | 100 pg | 500 pg |
| 322 | 250 pg | 1 ng | 300 pg | 2–3 ng |
| 345 | 30–40 pg | 90–100 pg | 100–200 pg | 900 pg |
| 352 | 30–40 pg | 90–100 pg | 200–300 pg | 900 pg |
| 374 | 100 pg | 500 pg | 500 pg | 1–1.2 ng |
| 377 | 20 pg | 60 pg | 100–200 pg | 1 ng |
| 378 | 10–20 pg | 60 pg | 100–200 pg | 1 ng |
| 381 | 10–20 pg | 80–100 pg | 300 pg | 1 ng |
| 388 | 60 pg | 300 pg | 100 pg | 300–500 pg |
| 390 | 30–40 pg | 90–100 pg | 200 pg | 2 ng |
| 396 | 30–40 pg | 150 pg | 100–200 pg | 800–900 pg |

TABLE 8-continued

Senstivity of nucleic acid detection in electrophoretic gels

| Dye Name | DNA (254 nm) | DNA (300 nm) | RNA (254 nm) | RNA (300 nm) |
|---|---|---|---|---|
| 398 | 30–40 pg | 150 pg | 100 pg | 500 pg |
| 410 | 20 pg | 100 pg | 200 pg | 2 ng |
| 937 | 10–20 pg | 50–60 pg | 200 pg | 800–900 pg |
| 1004 | 20 pg | 60 pg | 100 pg | 300–500 pg |
| 1151 | 20 pg | 80–100 pg | 300 pg | 1 ng |
| 1169 | 60 pg | 150–180 pg | 300 pg | 1 ng |
| 1170 | 20–30 pg | 60 pg | 300 pg | 1 ng |
| 1172 | 20–30 pg | 60 pg | 200 pg | 900 pg |
| 3100 | 700 pg | >1 ng | 300 pg | 900 pg |

For each test, a dilution series of λcI857 DNA cut with Hind III restriction endonuclease or a dilution series of E. coli ribosomal RNA was electrophoresed in 10 cm×10 cm×0.4 cm 1% agarose gels. Gels were poststained with a 1 µM solution of each dye in TBE buffer for 20 minutes and photographed through a Wratten 15 gelatin filter, with Polaroid black and white print film, using 254 nm epi-illumination or 300 nm transillumination as indicated. Numbers indicate the amount of nucleic acid in the lowest intensity band that was visible in the Polaroid photograph; bands were 3.5 mm wide.

Figure 9:
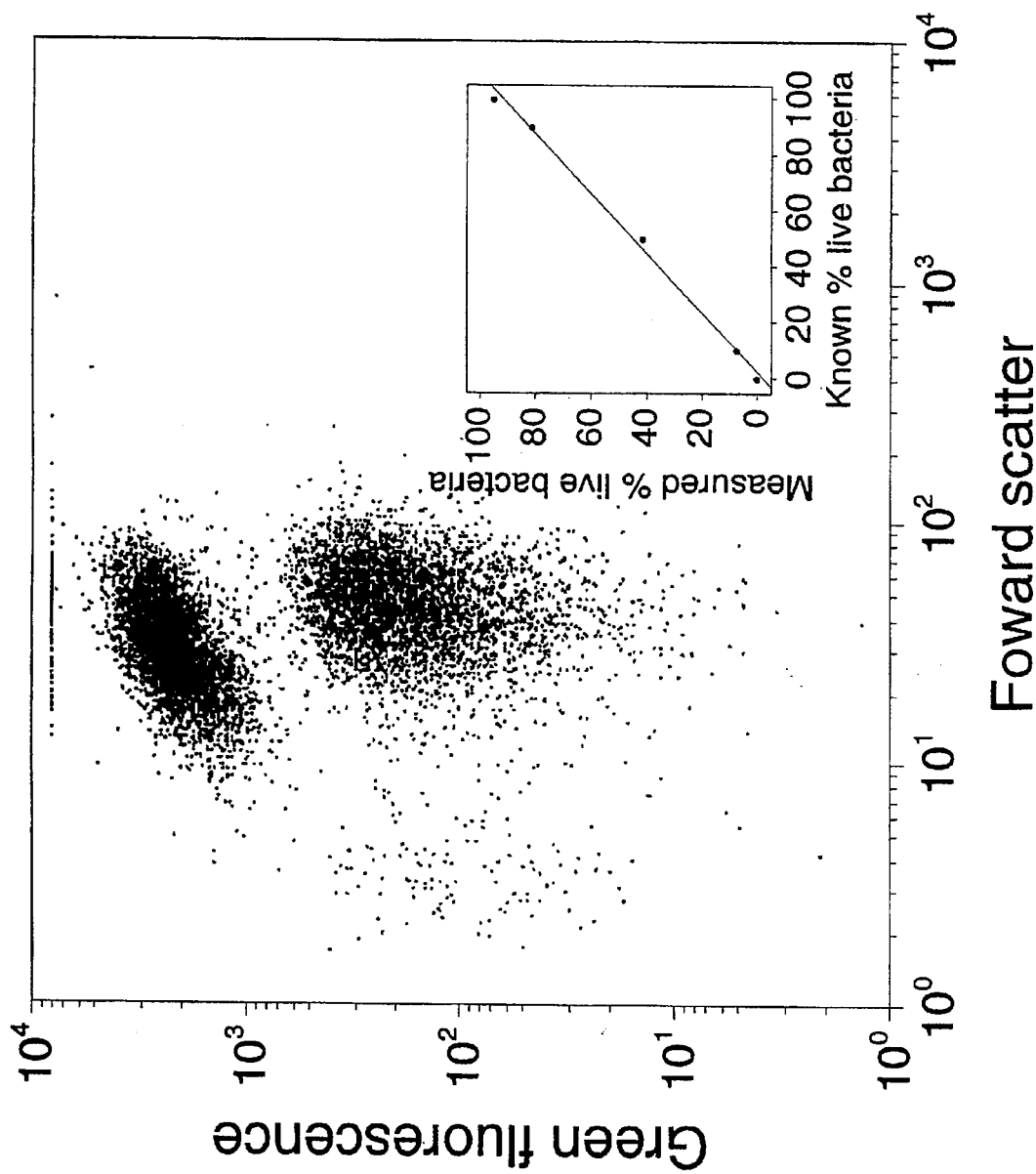
FIG. 9: Analysis of a cell suspension by flow cytometry, as described in Example 53. A linear relationship exists between the distribution of cells in the two regions and the actual percentage of live cells in the sample, as shown in the inset figure.

Alternatively, the presence or location of nucleic acids, stained as above, can in turn be used to indicate the presence or location of organisms, cells, or organelles containing the nucleic acids, where the presence or location of the fluorescent signal corresponds to the presence or location of the biological structure (e.g. stained cells or organelles). Infective agents such as bacteria, mycoplasma, mycobacteria, viruses and parasitic microorganisms, as well as other cells, can be stained and detected inside of eukaryote cells, although the fluorescent signal generated by an individual virus particle is below the resolution level of standard detection instrumentation. In a further embodiment of the invention the fluorescent signal resulting from formation of the dye-nucleic acid complex is used as a basis for sorting cells, for example sorting stained cells from unstained cells or sorting cells with one set of spectral properties from cells with another set of spectral properties (Examples 49, 53; FIGS. 8, 9).

In addition to detection of the presence or location of nucleic acids as well as their enclosing structures, the staining profile that results from the formation of the dye-nucleic acid complex is indicative of one or more characteristics of the sample. By staining profile is meant the shape, location, distribution, spectral properties of the profile of fluorescent signals resulting from excitation of the fluorescent dye-nucleic acid complexes. The sample can be characterized simply by staining the sample and detecting the staining profile that is indicative of a characteristic of the sample. More effective characterization is achieved by utilizing a dye that is selective for a certain characteristic of the sample being evaluated or by utilizing an additional reagent (as described below), where the additional reagent is selective for the same characteristic to a greater or lesser extent or where the additional reagent is selective for a different characteristic of the same sample. The dyes of the invention exhibit varying degrees of selectivity with regard to nucleic acid structure, location, and cell type, and with regard to cell permeability. Some dyes selectively stain the nucleus, other selectively stain the mitochondria or mitochondrial nucleoids in certain cell types; some stain only dead cells (i.e. with compromised cell membranes); some dyes selectively give a better signal on RNA than DNA or vice versa; some give a greater signal on AT or GC rich polymers; and some dyes are relatively non-selective in staining all nucleic acids, all intracellular nucleic acids, or all cell types (Tables 6–9 and 12; Example 44).

TABLE 9

Staining Pattern of Selected Dyes

| DYE | Yeast (Saccharomyces cerevisiae) | Mouse fibroblasts (NIH 3T3) | Canine kidney cells (MDCK) | Human carcinoma cells (A431) | Mouse myeloma cells (P3X) | Mouse monocyte macrophages (MMM) |
|---|---|---|---|---|---|---|
| Hoechst 33342 | nucleus | nucleus | nucleus | nucleus | nucleus | nucleus |
| SYTO 14 | mitochondria | nucleus, faint cytoplasm | n.d. | n.d. | n.d. | n.d. |
| 352 | mitochondria | n.d. | n.d. | n.d. | n.d. | n.d. |
| 381 | nucleus | n.d. | n.d. | n.d. | n.d. | n.d. |
| 224 | mitochondria | mitochondrial nucleoids | mitochondrial nucleoids | mitochondrial nucleoids | mitochondrial nucleoids | mitochondrial nucleoids |
| 410 | mitchondria and vacuole | mitonchondrial nucleoids | mitonchondrial nucleoids | mitonchondrial nucleoids | mitonchondrial nucleoids | mitonchondrial nucleoids |
| 937 | nucleus and mitochondria | nucleus and mitochondrial nucleoids | n.d. | n.d. | n.d. | n.d. |

In one embodiment of the invention, where the dye is selected to be membrane permeable or relatively impermeant to cell membranes, the staining profile that results from the formation of the dye-nucleic acid complex is indicative of the integrity of the cell membrane, which in turn is indicative of cell viability. The cells are stained as above for a time period and dye concentration sufficient to give a detectable fluorescent signal in cells with compromised membranes. The required time period is dependent on temperature and concentration, and can be optimized by standard procedures within the general parameters as previously described. Relatively impermeant dyes of the invention are used to indicate cells where the cell membranes are disrupted. Where the dye selected is impermeant to cells with intact membranes, formation of the fluorescent dye-nucleic acid complex inside the cell is indicative that the integrity of the cell membrane is disrupted and the lack of fluorescent dye-nucleic acid complexes inside the cell is indicative that the cell is intact or viable. The impermeant dye is optionally used in conjunction with a counterstain that gives a detectably different signal and is indicative of metabolically active cells or, in combination with the impermeant dye, is indicative of cells with intact membranes. Alternatively, the more permeant dyes of the invention are used to stain both cells with intact membranes and cells with disrupted membranes, which when used in conjunction with a counterstain that gives a detectably different signal in cells with disrupted membranes, allows the differentiation of viable cells from dead cells. The counterstain that gives a detectably different signal in cells with disrupted membranes is optionally an impermeant dye of the invention or another reagent that indicates loss of integrity of the cell membrane or lack of metabolic activity of the dead cells. When the cells are stained with a concentration of dye that is known to stain live bacteria, the relative reduction of a fluorescence intensity can be used to distinguish quiescent bacteria, which are not actively expressing proteins, from metabolically active bacteria (FIGS. 8A & 8B; Example 49).

In a further embodiment of the invention, the shape and distribution of the staining profile of dye-nucleic acid complexes is indicative of the type of cell or biological structure that contains the stained nucleic acids. Cells may be discriminated by eye based on the visual fluorescent signal or be discriminated by instrumentation as described above, based on the spectral properties of the fluorescent signal. For example, dyes that are non-selective for staining nucleic acids in intracellular organelles can be used to identify cells that have an abundance or lack of such organelles, or the presence of micronuclei and other abnormal subparticles containing nucleic acids and characteristic of abnormal or diseased cells. A sample may be characterized as containing blebbing cells or nuclei based on the visible staining profile. Dyes that are selective for the nucleic acids in a particular organelle (e.g. in the nucleus or in mitochondria), even in the presence of limited staining of nucleic acids in the cytoplasm or other organelles, can be used to characterize cells as containing or lacking such organelles based on the intensity as well as the location of the signal, allowing the use of instrumentation to characterize the sample. Typically the staining profile used to characterize the sample is indicative of the presence, shape, or location of organelles or of cells, where the cells are located in a biological fluid, in a tissue, or in other cells.

Furthermore, the differential permeability of bacterial and higher eukaryotic cells to some dyes allows selective staining of live mammalian cells with little or no staining of live bacteria. A dye selected to be permeant to bacteria can be used in combination with a dye that is only permeant to eukaryotes to differentiate bacteria in the presence of eukaryotes. Dead bacteria with compromised membranes, such as those in the phagovacuoles of active macrophages or neutrophils, may be rendered permeable to the dyes that are otherwise only permeant to eukaryotes, as a result of toxic agents produced by the phagocytic cells (Example 48).

In another embodiment of the invention, the staining profile results from the formation of the dye-nucleic acid complex in an electrophoretic gel, or sedimentation or centrifugation gradient. In addition to indicating the presence of nucleic acids in the gel, the staining profile is indicative of one or more characteristics of the nucleic acid solution applied to the gel. The number of bands and/or the intensity of the signal per band of the staining profile, for example, is indicative of the purity or homogeneity of the nucleic acid solution. Band tightness and degree of smearing is indicative of the integrity of the nucleic acid polymers in the solution. The size, conformation, and composition of the polymers, are indicated by the relative mobility of the polymer through the gel (Examples 37, 38), which can be used to detect changes caused by interaction of analytes with the nucleic acid polymer such as protein binding or enzymatic activity. Preferred embodiments of the dyes have low intrinsic fluorescence so there is no need to destain gels to remove free dye. Furthermore, the fluorescence of the dye-nucleic acid complex is not quenched by denaturants such as urea and formaldehyde, eliminating the need for their removal from the gels prior to staining.

In yet another embodiment of the invention, the staining profile is indicative of the presence or predominance of a type of nucleic acid that is used to characterize the sample. In one embodiment of the invention, the dye is chosen to be more selective for AT or GC rich polymers, such that staining profile is indicative of the relative proportion of these bases (Example 44, Table 12). In another embodiment of the invention, the spectral properties of the nucleic acid-dye complex vary depending on the secondary structure of the nucleic acid present in the complex. Typically, the spectral properties will vary in fluorescence enhancement, fluorescence polarization, fluorescence lifetime, excitation wavelength or emission wavelength, preferably emission wavelength. A comparison of the fluorescence response of a sample of unknown nucleic acids with that of a stained nucleic acid of known secondary structure allows the secondary structure of the unknown nucleic acids to be determined, and the amount of nucleic acids in the sample to be quantified. In this manner, RNA and single-stranded DNA can be differentiated from double-stranded DNA (Example 43). Where nuclease is added to the nucleic acid polymers in solution or in fixed cells to digest the RNA or DNA prior to combining with the dye, the fluorescent signal from the dye-nucleic acid complex can be used to discriminate the nucleic acid polymer that was not digested in the presence of the nuclease from undigested polymers (Example 42).

Figure 6:
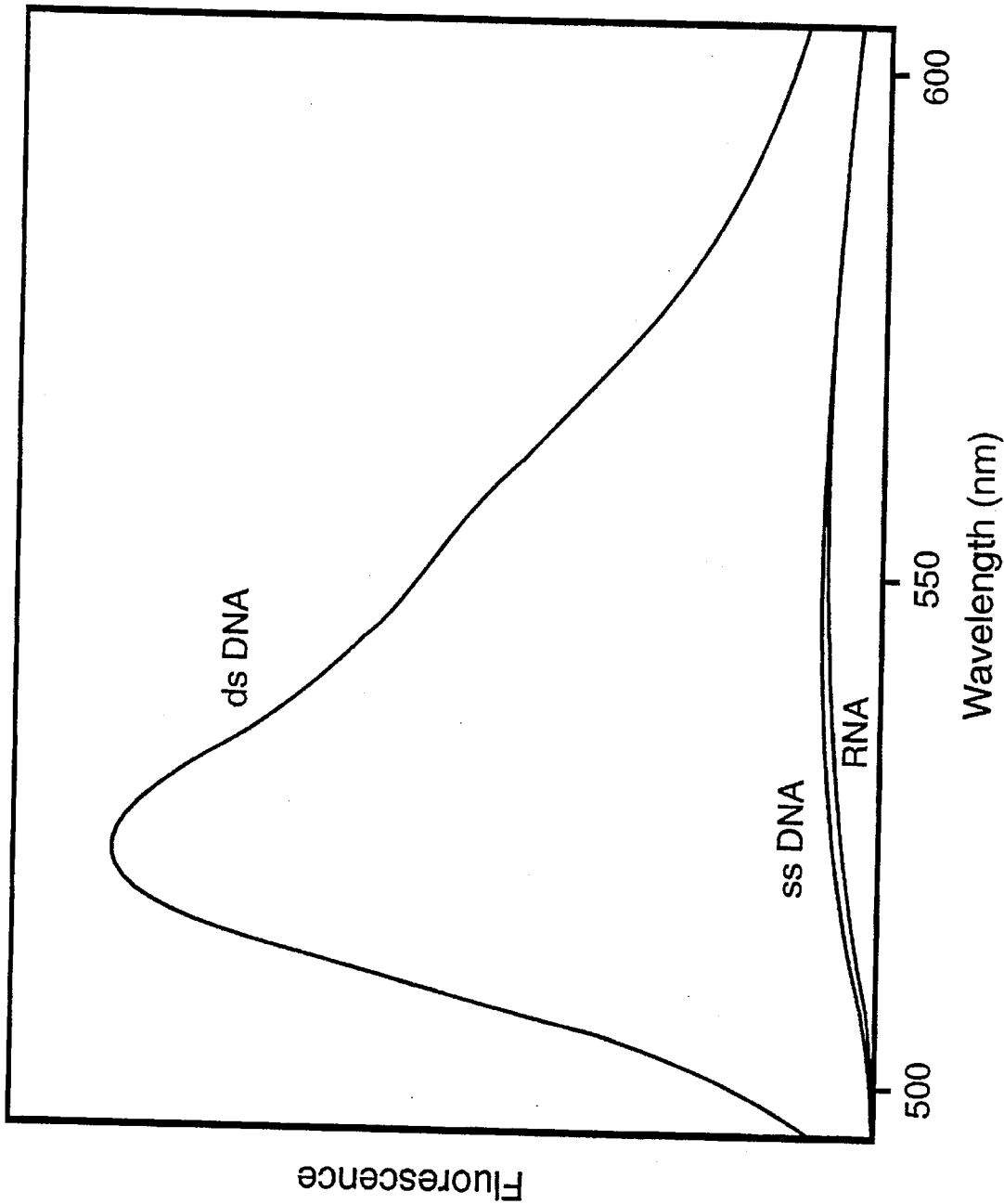
FIG. 6: Fluorescence emission as a function of nucleic acid type, as described in Example 43.

This same property of sensitivity to secondary structure by monomethine dyes can be used to quantitate ds nucleic acids in the presence of ss nucleic acids. Samples containing both ds and ss DNA or RNA yield emission maxima in both the green and longer wavelength regions at high dye:base ratios. Meaningful information about the amounts of ss and ds nucleic acids in solution can be gathered by a direct comparison of the spectra of the low dye ratio sample and high dye ratio sample. For example, where a nucleic acid solution such as purified oligonucleotides, DNA amplification reactions, a cDNA synthesis, plasmid preparation, or cell extraction is stained with a high dye concentration (i.e. greater than or equal to the concentration of nucleic acid bases), the fluorescent signal that results from complexes formed by ss nucleic acids is red-shifted from the fluorescent signal formed by ds nucleic acids. Where the dye is selected to give a high quantum yield with ds nucleic acids and the quantum yield of the red-shifted fluorescent signal is minimal, the quantum yield of the stronger signal can be used to quantitate the amount of ds nucleic acid in the sample, even in the presence of ss nucleic acids (Example 43; FIG. 6).

The nucleic acids for this and other applications are quantitated by comparison of the detectable fluorescent signal from the dye-nucleic acid complex, with a fluorescent standard characteristic of a given amount of nucleic acid (Examples 23, 24, 41, 42). Where one type of nucleic acid in a sample is selectively digested to completion, the fluorescent signal can be used to quantitate the polymer remaining after digestion (Example 42). Alternatively, prior to being stained, a solution of nucleic acid polymers is separated into discrete fractions using standard separation techniques and the amount of nucleic acid present in each fraction is quantitated using the intensity of the fluorescent signal that corresponds to that portion. The solution may be purified synthetic or natural nucleic acids or crude mixtures of cell extracts or tissue homogenates. Where aliquots from a single sample are taken over time, and the nucleic acid content of each aliquot is quantitated, the rate of cell or nucleic acid proliferation is readily determined from the change in the corresponding fluorescence over time (Example 41).

In another aspect of the invention, the dye-nucleic acid complex is used as a fluorescent tracer or as probe for the presence of an analyte. In one aspect of the invention, the dye-nucleic acid complex is used as a size or mobility standard, such as in electrophoresis or flow cytometry. Alternatively, the fluorescent signal that results from the interaction of the dye with nucleic acid polymers can be used to detect or quantitate the activity or presence of other molecules that interact with nucleic acids. The nucleic acid polymers used to form the dye-nucleic acid complex are optionally attached to a solid or semi-solid support, such as described above, or is free in solution, or is enclosed in a biological structure. Such molecules include drugs, other dyes, proteins such as histones or ds or ss DNA or RNA binding proteins, or enzymes such as endonucleases or topoisomerases. In one aspect of the invention, a dye having a binding affinity for nucleic acid greater than that of the analyte being assayed displaces the analyte or prevents the interaction of the analyte with the nucleic acid polymer. For example, DNA templates that are heavily bound with a high affinity dye such as dye 937 (i.e. at ratios of greater than 3 bp:dye molecule in the staining solution) are protected from DNase I activity. Typically the dyes having a binding affinity greater than $10^{-6}$M, more typically greater than $10^{-8}$M, are effective to displace analytes that interact with nucleic acids. Dye affinity is determined by measuring the fluorescence of the dye-nucleic acid complex, fitting the resulting data to an equilibrium equation and solving for the association constant. In another aspect of the invention, dyes having a binding affinity that is less than that of the analyte being assayed are displaced from the dye-nucleic acid complex by the presence of the analyte, with the resultant loss of fluorescence. For example, lower affinity dye molecules prebound to double-stranded DNA are displaced by histones.

In one embodiment, the complex is used as an indicator of enzymatic activity, that is, as a substrate for nucleases, topoisomerases, gyrases, and other enzymes that interact with nucleic acids (Example 26). Alternatively, the complex is used to quantitate the abundance of proteins (such as histones) that bind nucleic acids, or of DNA binding drugs (such as distamycin, spermine, actinomycin, mithramycin, chromomycin). The fluorescent complex is combined with the sample thought to contain the analyte and the resultant increase or decrease in fluorescent signal qualitatively or quantitatively indicates the presence of the analyte.

Additional Reagents

The dyes of the invention can be used in conjunction with one or more additional reagents that are separately detectable. The additional reagents may be separately detectable if they are used separately, e.g. used to stain different aliquots of the same sample (e.g. Example 42) or if they stain different parts or components of a sample (e.g. Examples 45 and 46), regardless of whether the signal of the additional reagents is detectably different from the fluorescent signal of the dye-nucleic acid complex. Alternatively, the dye of the invention is selected to give a detectable response that is different from that of other reagents desired to be used in combination with the subject dyes. Preferably the additional reagent or reagents are fluorescent and have different spectral properties from those of the dye-nucleic acid complex. For example, dyes that form complexes that permit excitation beyond 600 nm can be used in combination with commonly used fluorescent antibodies such as those labelled with fluorescein isothiocyanate or phycoerythrin. Any fluorescence detection system (including visual inspection) can be used to detect differences in spectral properties between dyes, with differing levels of sensitivity. Such differences include, but are not limited to, a difference in excitation maxima, a difference in emission maxima, a difference in fluorescence lifetimes, a difference in fluorescence emission intensity at the same excitation wavelength or at a different wavelength, a difference in absorptivity, a difference in fluorescence polarization, a difference in fluorescence enhancement in combination with target materials, or combinations thereof. The detectably different dye is optionally one of the dyes of the invention having different spectral properties and different selectivity. In one aspect of the invention, the dye-nucleic acid complex and the additional detection reagents have the same or overlapping excitation spectra, but possess visibly different emission spectra, generally having emission maxima separated by >10 nm, preferably >20 nm, more preferably >50 nm. Simultaneous excitation of all fluorescent reagents may require excitation of the sample at a wavelength that is suboptimal for each reagent individually, but optimal for the combination of reagents. Alternatively, the additional reagent(s) can be simultaneously or sequentially excited at a wavelength that is different from that used to excite the subject dye-nucleic acid complex (e.g. Example 48). In yet another alternative, one or more additional reagents are used to quench or partially quench the fluorescence of the dye-nucleic acid complex, such as by adding a second reagent to improve the selectivity for a particular nucleic acid or the AT/GC selectivity (Example 29).

The additional dyes are optionally used to differentiate cells or cell-free samples containing nucleic acids according to size, shape, metabolic state, physiological condition, genotype, or other biological parameters or combinations thereof. The additional reagent is optionally selective for a particular characteristic of the sample for use in conjunction with a non-selective reagent for the same characteristic, or is selective for one characteristic of the sample for use in conjunction with a reagent that is selective for another characteristic of the sample. In one aspect of the invention, the additional dye or dyes are metabolized intracellularly to give a fluorescent product inside certain cells but not inside other cells, so that the fluorescence response of the cyanine dye of the invention predominates only where such metabolic process is not taking place. Alternatively, the additional dye or dyes are specific for some external component of the cell such as cell surface proteins or receptors, e.g. fluorescent lectins or antibodies (Examples 34, 45). In yet another aspect of the invention, the additional dye or dyes actively or passively cross the cell membrane and are used to indicate the integrity or functioning of the cell membrane (e.g. calcein AM or BCECF AM). In another aspect, the additional reagents bind selectively to AT-rich nucleic acids and are used to indicate chromosome banding. In another aspect of the invention, the additional reagent is an organelle stain, i.e. a stain that is selective for a particular organelle, for example the additional reagent(s) may be selected for potential sensitive uptake into the mitochondria (e.g. rhodamine 123 or tetramethyl rosamine) or for uptake due to pH gradient in an organelle of a live cell (e.g. Diwu, et al., CYTOMETRY supp.7, p77, Abstract 426B (1994)).

The additional dyes are added to the sample being analyzed to be present in an effective amount, with the optimal concentration of dye determined by standard procedures generally known in the art. Each dye is optionally prepared in a separate solution or combined in one solution, depending on the intended use. After illumination of the dyed cells at a suitable wavelength, as above, the cells are analyzed according to their fluorescence response to the illumination. In addition, the differential fluorescence response can be used as a basis for sorting the cells or nucleic acids for further analysis or experimentation. For example, all cells that "survive" a certain procedure are sorted, or all cells of a certain type in a sample are sorted. The cells can be sorted manually or using an automated technique such as flow cytometry, according to the procedures known in the art, such as in U.S. Pat. No. 4,665,024 to Mansour, et al. (1987).

The examples below are given so as to illustrate the practice of this invention. They are not intended to limit or define the entire scope of this invention.

Example 1: Preparation of 1,2-dihydro-4-methyl-1-phenyl-2-quinolone (1)

The following compound is prepared:

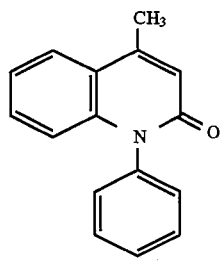

The synthetic precursor (1) is prepared either by an Ullmann coupling according to a literature procedure (Wawzonek, et al., J. HETEROCYCLIC CHEM., 25, 381 (1988)) or via the reaction of the corresponding diarylamine with diketene followed by acid cyclization (Elderfield, HETEROCYCLIC COMPOUNDS, Vol. 4, pp. 1–331, (1952)). Thus 10.0 g (62.9 mmoles) of 2-hydroxy-4-methylquinoline is heated at reflux with 24.0 g (377 mmoles) of copper powder, 8.68 g (62.9 mmoles) of potassium carbonate and 19.2 g (94 mmoles) of iodobenzene for 48 hours. The reaction is cooled to room temperature, partitioned between water and ethyl acetate, filtered, and the organic layer is dried over magnesium sulfate. The crude product is purified on a silica gel column, eluting with 1:1 ethyl acetate/hexanes to yield 8.1 g of the desired product.

Example 2: Preparation of 2-chloro-4-methyl-1-phenylquinolinium chloride (2)

The following compound is prepared:

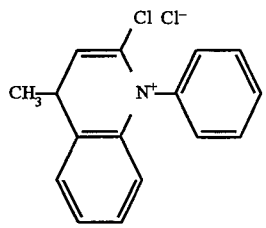

To 2.8 g (11.9 mmoles) of 1 in 20 mL of methylene chloride is added 1.85 g of POCl$_3$ and a catalytic amount of dimethylformamide (Marson, TETRAHEDRON., 48, 3659 (1992)). The resulting mixture is heated to reflux for 24 hours. The crude product is used in a further reaction, or is purified using column chromatography.

The methoxyquinolinium analog is prepared in the same way, except using 1,2-dihydro-7-methoxy-4-methyl-1-phenyl-2-quinolone in place of 1.

Example 3. Preparation of Dye 640

The following compound is prepared:

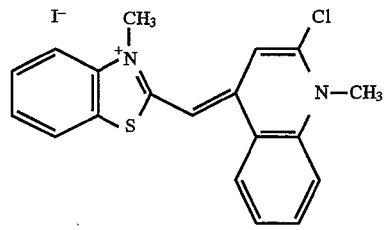

The commercially available 2-chloro-3-methylquinoline is methylated by heating with an excess of methyl iodide in a sealed tube at 120° C. for one hour. At the end of the reaction, ethyl acetate is added and the precipitate is filtered to isolate the quinolinium iodide. This intermediate compound is then stirred with 3-methyl-2-methylthiobenzothiazolinium tosylate in methylene chloride in the presence of one equivalent of triethylamine to yield the desired product.

An alterative synthetic route utilizes 4-[2,3-dihydro-3-methyl-(benzo-1,3-thiazol-2-yl)-methylidene-1,2-dihydro-1-methyl-2-quinolone, which in turn is prepared from 1,2-dihydro-4-methyl-1-methyl-2-quinolone (1) and 3-methyl-2-methylthiobenzothiazolium tosylate. For example, the lithium enolate or silyl enolate of the quinoline is stirred with the benzothiazolium tosylate.

Example 4: Preparation of 2-chloro-4-[2,3-dihydro-3-methyl-(benzo-1,3-thiazol-2-yl)-methylidene]-1-phenylquinolinium iodide (3)

The following compound is prepared:

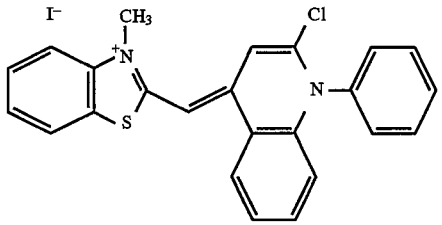

A room temperature solution of 2 (11.9 mmoles) is prepared, and 3.5 g (9.6 mmoles) of 3-methyl-2-methylthiobenzothiazolium tosylate (4) (commercially available, TCI) is added followed by 1.3 mL (9.4 mmoles) of triethylamine. The mixture is stirred for an additional 6 hours. The crude product is purified on silica gel using ethyl acetate:chloroform:methanol, 3:3:1 as eluant. The product is then recrystallized from methanol/chloroform/ethyl acetate.

The pyridinium analog is prepared in the same way, except using the pyridinium analog of 2.

The trimethine dye analog is prepared similarly, except using 2-(2-anilinovinyl)-3-methylbenzothiazolium tosylate in place of 4.

An additional synthetic route to the product utilizes 4-[2,3-dihydro-3-methyl-(benzo-1,3-thiazol-2-yl)-methylidene]-1,2-dihydro-1-phenyl-2-quinolone (5), which in turn is prepared from 1,2-dihydro-4-methyl-1-phenyl-2-quinolone (1) and 4. Thus the lithium enolate of 1 (prepared from treating the quinolone with 2.7 equivalent of lithium diisopropyl amide) or the silyl enolate of 1 (from (1) and trimethylsilyl trifluoromethanesulfonate and diisopropylethylamine) is stirred with 4. The desired intermediate is isolated by column chromatography. The quinolone (5) is then treated with POCl$_3$ to generate the desired 2-chloro intermediate.

Example 5: Preparation of Dye 937

The following compound is prepared:

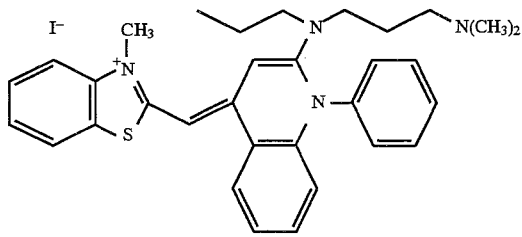

Dye 937 is prepared by heating 3 at 55° C. in the presence of N-(3-dimethylaminopropyl)-N-propylamine in 1,2-dichloroetheane for two hours.

A family of analogous aminoalkylamino-substituted dyes are prepared similarly, by treating the appropriate 2-chloro derivative with a selected amine (For example Dyes 211, 298, 342, 377, 396, 397, 856, 938, 993, 10101, 1004, and 1168).

Example 6. Preparation of Dye 1107

The following compound is prepared:

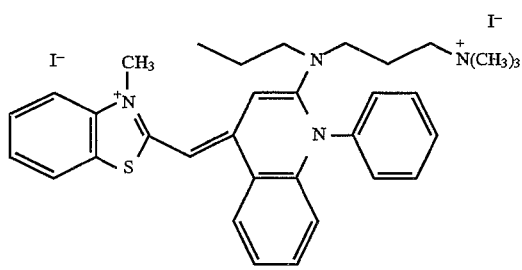

Dye 937 is treated with an excess of methyl iodide and PROTON-SPONGE (Aldrich) to methylate the dimethylamine and give the quaternary ammonium salt. A family of analogous ammoniumalkylamino-substituted dyes are prepared similarly, by treated an appropriate aminoalkylamino-substituted dye (See Example 5) with methyl iodide and PROTON-SPONGE (For example, Dyes 308, 309, 345, 398, 1107, 1114, 1170, 1172, and 3102).

Example 7: Preparation of Dye 1004

The following compound is prepared:

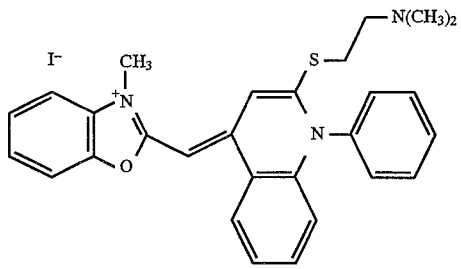

2-Dimethylaminoethanethiol is added to 2-chloro-4-[2,3-dihydro-3-methyl-(benzo-1,3-oxazol-2-yl)-methylidene]-1-phenylquinolinium iodide (the benzoxazolium analog of 3) in methylene chloride, followed by triethylamine, and the resulting mixture is stirred at room temperature for 1.5 hours. The volume of solvent is reduced under reduced pressure and the product is isolated by filtration.

A family of analogous aminoalkylthioether-substituted dyes are prepared similarly, by treating the appropriate 2-chloro derivative with a selected aminoalkylthiol in the presence of one equivalent of triethylamine (For example Dyes 365, 380, 387, 996, 1004, and 1169). The resulting dyes are quaternized using the method of Example 6 to yield the corresponding ammoniumalkylthioether-substituted dyes (For example Dyes 352, 391, 1155, and 1167).

Example 8. Preparation of Dyes 314 and 316

The following compound is prepared:

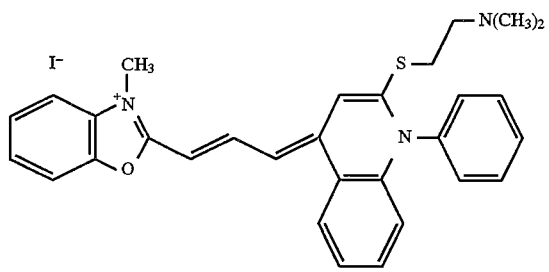

The 1,2-dihydro-4-methyl-1-phenyl-2-quinolone is heated at reflux with 1.3 equivalents of phosphorus oxychloride and 1 equivalent of DMF in toluene for one hour to generate the 2-chloro-4-methyl-1-phenylquinolinium chloride (3). The chloride is then stirred in the corresponding dimethylaminoethanethiol in methylene chloride to produce the corresponding 2-dimethylaminoethylthio-1-phenylquinolinium chloride. This is then reacted with one equivalent each of the 2-(2-anilinovinyl)-3-methyl-benzoxazolium tosylate, triethylamine and acetic anhydride to generate the corresponding trimethine derivative.

The dimethylamino derivative is quaternized using excess methyl iodide and PROTON-SPONGE to yield Dye 316.

Example 9. Preparation of Dye 381

The following compound is prepared:

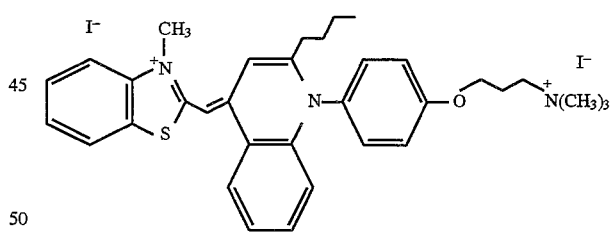

The starting 1,2-dihydro-4-methyl-1-(4'-methoxyphenyl)-2-quinolone is prepared by an Ullmann reaction of the 2-hydroxy-4-methylquinoline with 4-iodoanisole. The methyl ether is demethylated with boron tribromide and the resulting phenol is alkylated in acetone with 3-dimethylaminopropyl chloride and potassium carbonate to yield the dimethylaminoalkylether quinolone. To this quinolone in THF at −78° C. is added 3 equivalents of n-butyllithium. After one hour at low temperature the reaction is quenched with 5 equivalents of acetic acid and allowed to warm to room temperature, where it is stirred for an additional several hours. The volatile components are removed under vacuum and the resulting crude quinolinium salt is stirred with 3-methyl-2-methylthiobenzothiazolium tosylate in methylene chloride in the presence of triethylamine to generate the corresponding 2-butyl-1-((3'-dimethylaminopropoxy)phenyl)-cyanine, which is quarternized as above with methyl iodide and PROTON-SPONGE to yield the desired product.

Example 10. Preparation of Dye 374

The following compound is prepared:

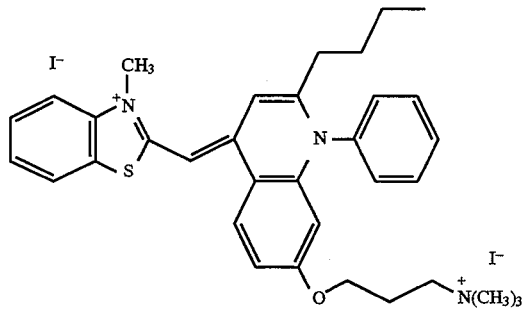

The procedure is similar to that used to prepared Dye 381 (Example 8) except that 1,2-dihydro-7-(3'-dimethylaminopropoxy)-4-methyl-1-phenyl-2-quinolone is used as the starting material instead of 1,2-dihydro-4-methyl-1-(4'-(3"-dimethylaminopropoxyphenyl)-2-quinolone.

Example 11. Preparation of Dye 3100

The following compound is prepared:

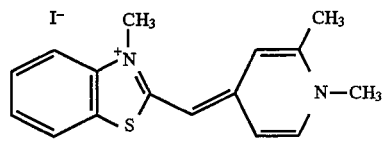

2,4-Lutidine is heated with methyl iodide in a sealed tube at 100° C. to generate the pyridinium iodide, which is then treated with the 3-methyl-2-methylthiobenzothiazolium tosylate in the presence of one equivalent of triethylamine to generate the desired product.

Example 12. Preparation of Dye 3103

The following compound is prepared:

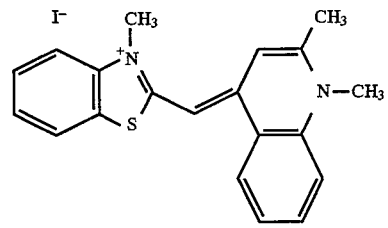

The corresponding 2-chloro derivative is heated at about 90° C., in a sealed tube, in a 1:1 v/v mixture of chloroform/methanol for 10 hours to yield the desired product.

Example 13. Preparation of Dye 388

The following compound is prepared:

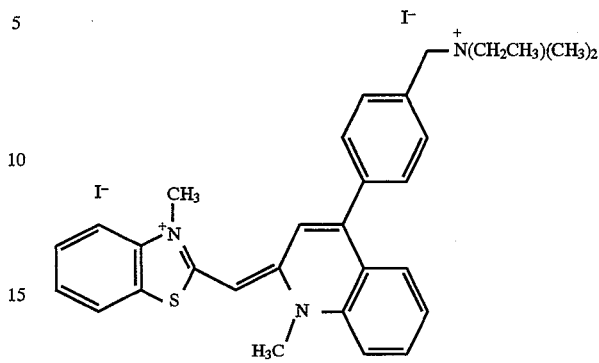

To 1,2-dimethyl-4-quinolone in THF at −78° C., is added 3 equivalents of 4-diethylaminomethylphenyllithium. The reaction mixture is stirred at room temperature for one hour, after which 5 equivalents of acetic acid is added, the mixture is warmed to room temperature and stirred for an additional 3 hours. All the volatile materials are removed under vacuum and the crude residue is stirred with one equivalent each of 3-methyl-2-methylthiobenzothiazolium tosylate and triethylamine in methylene chloride to yield the diethylaminoalkyl derivative. This is quarternized directly with excess methyl iodide and PROTON-SPONGE to yield the desired product.

Example 14. Preparation of Dye 390

The following compound is prepared:

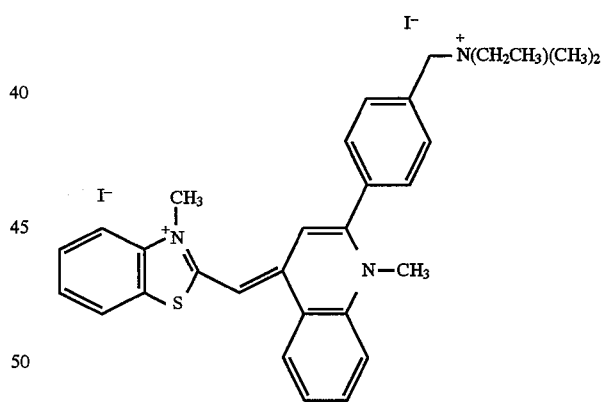

To a solution of 1,2-dihydro-1,4-dimethyl-2-quinolone in THF at −78° C. is added 3 equivalents of 4-diethylaminomethylphenyllithium, and the resulting solution is stirred for one hour. At the end of this period, 5 equivalents of acetic acid is added and the reaction mixture is allowed to warm to room temperature for several hours. All volatile components are removed under vacuum. The resulting residue is stirred with one equivalent of each of 3-methyl-2-methylthiobenzothiazolium tosylate and triethylamine in methylene chloride to yield the diethylamino derivative. The diethylamino derivative is quarternized with methyl iodide and PROTON-SPONGE to yield the desired product

Example 15. Preparation of Dye 365

The following compound is prepared:

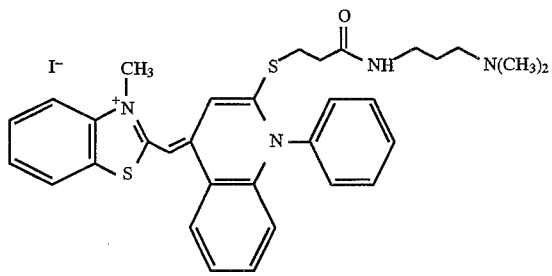

To a solution of 2-chloro-4-[2,3-dihydro-3-methyl-(benzo-1,3-thiazol-2-yl)-methylidene]-1-phenylquinolinium iodide in methylene chloride is added one equivalent each of 3-mercaptopropionic acid and triethylamine in that order. The resulting mixture is stirred at room temperature for one hour and then filtered. The acid obtained is activated by transformation to the N-succinimidyl ester with dicyclohexylcarbodiimide and N-hydroxysuccinimide. The succinimidyl ester is then treated with N,N-dimethylpropanediamine to yield the desired product.

Example 16. Preparation of Dye 380

The following compound is prepared:

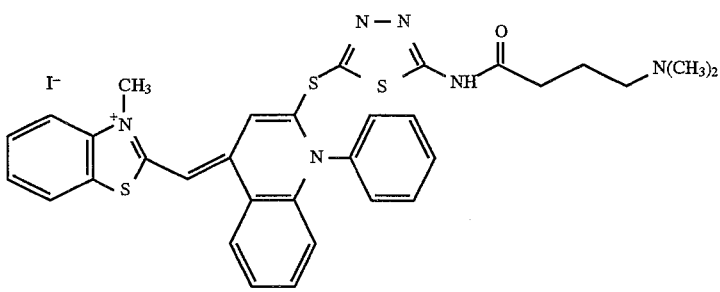

4-Dimethylaminobutyryl chloride is treated with one equivalent of 5-amino-1,3,4-thiadiazole-2-thiol (Aldrich) in the presence of triethylamine to generate the corresponding amide thiol. This intermediate product is then treated with 2-chloro-4-[2,3-dihydro-3-methyl-(benzo-1,3-thiazol-2-yl)-methylidene]-1-phenylquinolium iodide to yield the desired product.

Example 17. Preparation of Dye 1189

The following compound is prepared:

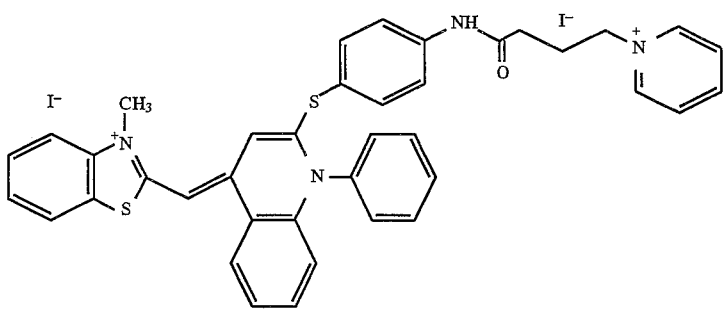

A solution of 2-chloro-4-(2,3-dihydro-3-methyl-(benzo-1,3-thiazol-2-yl)-methylidene)-1-phenylquinolium iodide is treated with 4-aminothiophenol to yield the corresponding 2-(4'-aminothiophenoxy) derivative. The aniline is then reacted with 4-bromobutyryl chloride (Lancaster) to yield the 4-bromobutyramide. This intermediate is heated with excess pyridine to yield the final product.

Example 18. Preparation of Dye 517

The following compound is prepared:

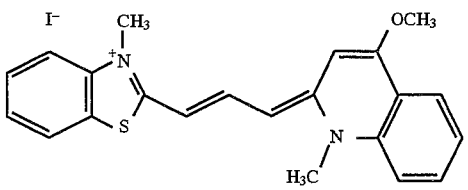

To 1,2-dimethyl-4-methoxy-quinolinium iodide in methylene chloride is added one equivalent each of 2-(2-anilinovinyl)-3-methylbenzothiazolium tosylate, triethylamine and acetic anhydride, in that order. The reaction is stirred at room temperature overnight to yield the product.

Example 19. Preparation of Dye 300
The following compound is prepared:

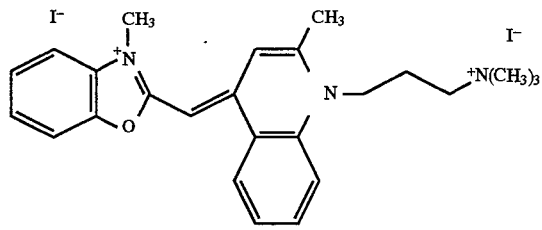

2,4-dimethylquinoline is heated with 10 equivalents of 1,3-diiodopropane, neat, at 150° C. to generate the quinolinium iodide. The iodide is then reacted with 3-methyl-2-methylthiobenzoxazolium tosylate in the presence of one equivalent of triethylamine to generate the 1-iodopropyl intermediate, which in turn is transformed to the final product by heating with a large excess of trimethylamine in a sealed tube at 100° C.

Example 20. Preparation of Dye 1199
The following compound is prepared:

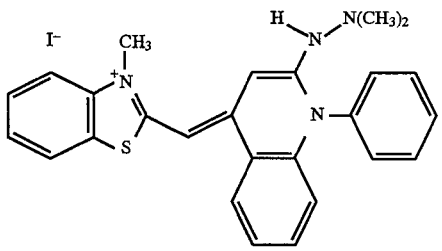

The 2-chloro dye derivative (3) is heated with 2 equivalents of N,N-dimethylhydrazine in 1,2-dichloroethane to generate the product.

Example 21. Detection of double-stranded DNA in electrophoretic gels

A dilution series of φX174 replicative form (double-stranded) bacteriophage DNA digested with either Hae III restriction endonuclease or λcI857 bacteriophage DNA digested with Hind III restriction endonuclease (both DNAs available commercially) is prepared in 10 mM Tris-HCl, pH 7.5, 1 mM ethylenediamine tetraacetic acid (EDTA) (TE). An equal volume of 15% FICOLL is added to each sample and samples are loaded onto a 5% polyacrylamide gel for the Hae III digest or to a 1% agarose gel for the Hind III digest. Electrophoresis is carried out under standard conditions. The resulting gels are transferred to small staining dishes containing a 1 μM solution of Dye 937 dye in 89 mM Tris base, 89 mM boric acid, 1 mM EDTA, pH 8 (TBE). The staining solution is then covered with foil to protect it from room light and agitated gently for 15–30 minutes. The gels are then transferred directly to a transilluminator and photographed using 300 nm transillumination or 254 nm epi-illumination, black and white Polaroid 667 print film and a Wratten 15 gelatin filter. DNA appears visually as bright green fluorescent bands.

Example 22. Detection of single-stranded nucleic acids in electrophoretic gels A dilution series of E. coli ribosomal RNA, M13 single-stranded DNA or a synthetic oligonucleotide is prepared in sterile water or TE. An equal volume of 15% FICOLL is added to each sample for native agarose or polyacrylamide electrophoresis. Samples are loaded onto native agarose gels, formaldehyde/agarose denaturing gels, native polyacrylamide gels and polyacrylamide/urea denaturing gels. Electrophoresis is carried out under standard conditions. The gels are then removed from the electrophoresis apparatus and placed directly in a solution containing 1 μM Dye 1004 in TBE. The staining gels are covered with foil to protect them from light and incubated for at least 20 minutes, with gentle agitation. The stained gels are then photographed directly, without destaining, exactly as in Example 21 for DNA detection. RNA and DNA bands appear as bright green fluorescent bands.

Example 23. Quantitation of double-stranded DNA in solution

A series of double-stranded DNA samples of unknown concentration is prepared in TE. A working solution of 0.8 μM Dye 993 is prepared in TE and kept protected from light. One mL of each DNA solution is placed in a fluorescence cuvette. One mL of working dye solution is added to each cuvette; the samples are mixed and incubated 2 to 5 minutes, protected from light. Fluorescence is measured in a standard fluorometer or microtiter plate reader, using 485 nm excitation light and measuring the emission at 520 nm. Fluorescence intensity is compared to a standard curve prepared from samples containing known DNA concentrations. The concentration of DNA in the unknown samples is determined by interpolation of the data in the standard curve. Samples containing DNA in excess of 1 μg/mL are diluted prior to quantitation. The assay is linear between about 25 pg/mL and 1 μg/mL in DNA concentration, as shown in FIG. 3. The assay is about 20-fold more sensitive than can be achieved with either YOYO-1 or YO-PRO-1 (0.5–1 ng/mL), about 400-fold more sensitive than Hoechst 33258 (10 ng/mL) and about 40,000-fold more sensitive than UV absorbance measurements (~1 μg/mL).

Example 24. Quantitation of single-stranded oligonucleotides in solution

A series of single-stranded synthetic oligonucleotides, synthesized from standard or morpholine-modified derivatives (AntiVirals Inc., Corvallis, Oreg.), at least 8 bases in length, in solutions of unknown concentration are diluted to 1 mL in TE in fluorescence cuvettes. One mL of a 0.5 μM solution of Dye 309 in TE is added to each sample, and the samples are incubated for 2–5 minutes at room temperature, protected from light. The samples are illuminated at 485 nm and the fluorescence of each sample is measured at 520 nm. The concentration of each solution is determined by comparison with a standard curve prepared using known amounts of oligonucleotides, as shown in FIG. 4. Samples containing in excess of about 1 μg/mL nucleic acid are diluted prior to analysis. Samples containing as little as about 100 pg/mL synthetic oligonucleotide with standard bases and links can be assayed. Samples containing morpholine modified links are detected at lower sensitivity, with such sensitivity being a function of sequence. Oligonucleotides of at least 8 bases in length can be measured. This sensitivity is greater than 10,000 times more sensitive than measurement of UV absorbance, which is the current method most commonly used for oligonucleotide detection and quantitation.

Example 25. Detection of oligonucleotides in blood

Whole blood is collected in vials containing EDTA. 0.5 mL aliquots of blood are transferred to 1.5 mL microfuge tubes. To each sample is added a 24 base oligonucleotide, in as small a volume as possible (1 to about 50 μL), in amounts ranging from 1 ng total up to about 10 μg total. Blood cells are pelleted by centrifugation in the microfuge for 1–2 minutes at 5000 rpm, at room temperature. The supernatant liquid is removed to fresh tubes, without disturbing the pellet. Remaining cells are removed by recentrifugation for 1–2 minutes at 10,000 rpm, at room temperature. The supernatant liquid is again carefully transferred to fresh tubes, without disturbing the pellet. An equal volume of phenol:CHCl$_3$:isoamyl alcohol, 24:24:1 is added to each tube, and the tubes are vortexed vigorously and centrifuged in the microfuge to separate phases (room temperature). The aqueous layer is removed to fresh tubes, carefully avoiding the interface. The extraction is repeated. Aliquots containing 200 μL of each sample are transferred to fluorescence cuvettes containing 800 μL TE. One mL of a 0.5 μM solution of Dye 309 in TE is added to each cuvette and samples mixed by inversion. The amounts of oligonucleotides present are determined by subtracting the fluorescence observed from a control sample containing no oligonucleotide, according to the method outlined in Example 24.

Example 26. Detection of DNase activity

Samples thought to exhibit DNase activity are incubated at 37° C. for five minutes with 10 ng of φX174 RF (double-stranded) DNA, digested with Pst I restriction endonuclease, in a buffer consisting of 50 mM Tris-HCl, pH 7.5, 10 mM MgCl$_2$, 1 mM CaCl$_2$, and 50 μg/mL bovine serum albumin in a total volume of 10 μL. Reactions are quenched by the addition of 2.5 μL, 100 mM EDTA and immediate vigorous mixing. An equal volume of 15% FICOLL is added to each sample and the samples are mixed briefly, then loaded onto a 1% agarose minigel along with molecular weight markers containing 0.05% bromophenol blue tracking dye and 7.5% FICOLL. The gel is electrophoresed under standard conditions, until the bromophenol blue has migrated at least 1½ to 2 inches. The gel is then removed from the electrophoresis apparatus and placed in a staining dish. A solution containing 1 μM Dye 937 in TBE is added to the gel and the gel is agitated gently, protected from light, for at least 20 minutes. The gel is transferred to a transilluminator, illuminated with 300 nm transillumination or 254 nm epi-illumination and photographed with Polaroid 667 black and white print film, through a Wratten 15 gelatin filter. DNase activity appears as smearing of the single, sharp Pst I digested DNA band. As little as 6.5 pg or ~2×10$^{-5}$ units of DNase I can be detected in this way. Restriction endonuclease activity or RNase activity can be assayed in a similar manner, using appropriate substrate nucleic acid molecules.

The assay is generalizable for topoisomerases, gyrases, restriction endonucleases, RNases, exonucleases, or any enzyme that acts on DNA in such a way that its electrophoretic mobility is altered.

Example 27. Detection of nucleic acids on a support

Plasmid pUC19 DNA is digested overnight with a single restriction endonuclease or a mixture of two enzymes. One μg of each sample is then loaded onto a 5% polyacrylamide gel and electrophoresed according to standard procedures. The gel is then stained with Dye 937 as described in Example 21 above. Bands are visualized by UV illumination, and the nucleic acids in the bands are denatured and electrophoretically transferred to a nylon membrane. After transfer, green fluorescent DNA bands are visualized using a hand-held UV lamp, due to the retention of Dye 937. The membrane is prehybridized, hybridized and washed according to standard procedures, using a biotin-labeled M13 sequencing primer (specific for the lacZ gene). Hybridized bands are detected using streptavidin alkaline phosphatase along with NBT/BCIP substrate. All fragments that contain a primer binding site show specific hybridization signals (a bluish/purple color). In addition, the presence of the dye also does not affect on the efficiency of hybridization, since an identical (control) gel that is not stained but is blotted and hybridized at the same time exhibits identical signals. The dye signal is lost during hybridization, so the blot is restained to visualize all of the DNA bands. RNA can also be detected on filter membranes by staining with an appropriate dye.

Example 28. Counterstaining metaphase chromosomes and interphase nuclei

Human metaphase chromosome spreads are prepared according to standard procedures. Spreads are denatured, prehybridized and hybridized, according to standard procedures, to alpha centromere repeat probes that have been labeled with a biotin-labeled nucleotide triphosphate by random pimg. The hybridized probes are then detected by further labeling with TEXAS RED fluorophore-labeled streptavidin and are counterstained by applying a 1 μM solution of Dye 1114 in phosphate-buffered saline (PBS). Samples are mounted, coverslips sealed and stained chromosomes are visualized with a fluorescence microscope and a fluorescein filter set to see the counterstain and a filter set appropriate for the TEXAS RED fluorophore to visualize the centromere signal. This assay can be generalized to be used with a fluorophore label, either on the nucleoside triphosphate or the streptavidin, that is spectrally distinct from the counterstain.

Example 29. Chromosome banding

The green fluorescent dyes of the present invention can be used to generate fluorescent banding on metaphase chromosomes, for karyotype or structural analysis, using a procedure essentially identical to that used for banding with YOYO-1 nucleic acid stain (Saitoh, et al., CELL, 76, 609 (1994)). The green fluorescent dye binds essentially nonselectively along the entire chromosome. Methyl Green binds selectively to regions with high AT content. Since Methyl Green quenches the green fluorescence, the result is a series of fluorescent green bands separated by dimmer high AT regions along the chromosome. Such bands are characteristic of particular chromosomes and can be used to distinguish them from one another. This enables karyotype analysis and the identification of genetic anomalies such as trisomies and translocations. Human metaphase chromosome spreads are prepared according to standard procedures. The coverslip is rinsed with PBS. The coverslip is then stained with 0.1 μM Dye 1114 in 0.1M sodium phosphate, pH 6.5 for 30 minutes at 37° C. and rinsed with PBS. Chromosomes are then counterstained with 10 mg/mL Methyl Green in the same buffer, for 30 minutes at 37° C. The slide is rinsed twice in PBS and then mounted in 10% PBS containing 1 mg/mL p-phenylenediamine and 78% glycerol. Chromosomes containing bands are observed through a fluorescence microscope equipped with a standard fluorescein filter set. The use of the dyes of the present invention has several advantages over the published procedure using YOYO-1 nucleic acid stain in that the present dyes do not repartition from the chromosomes onto the glass coverslip, and typically have greater quantum yields. Thus the fluorescent signal is more stable and the fluorescence background is lower.

Example 30. Detection of protein/DNA complexes in gels using pre-labeled DNA templates Single-stranded M13 phage DNA is incubated, in an appropriate binding buffer, with proteins required for T4 phage replication as follows: g41p, g61p and g41p in the presence of g61p. Since g41p is a DNA helicase, it binds DNA but does not form a stable complex in the absence of g61 p. The g61 p protein is a primase which binds DNA alone or in a complex with g41p. Samples are incubated for sufficient time for complex formation. Samples are then loaded onto an agarose gel and electrophoresed using a running buffer that is optimized for DNA/protein complex formation. The gel is stained with Dye 937 as described in Example 21 above. DNA containing bands are visualized directly using 254 nm epi-illumination or 300 nm transillumination. Samples containing primase alone or primase plus helicase result in shifted electrophoretic mobility complexes in comparison with samples containing no protein at all. The helicase does not yield a shifted complex by itself. This assay can be generalized to detect binding of any nucleic acid binding protein or factor that causes a shift in the electrophoretic mobility of the template upon binding.

Example 31. Detection of sequence-specific DNA binding proteins in cell extracts DNA templates of about 25 to about 200 base pairs in length, containing sequences of interest are incubated with Dye 1114 at a dye:bp ratio of 1:30, in the dark, at room temperature. A DNA template that is virtually identical, except for lacking the test sequence is labeled and treated in parallel. Extracts are prepared from cells of interest using standard techniques. Approximately 1 ng to 1 microgram of DNA is incubated with about 15 micrograms of protein from the crude extract, in the presence of about 2 micrograms of poly(dI-dC).poly(dI-dC) carrier nucleic acid and bovine serum albumin in a buffered solution. The sample is incubated for about 15 minutes at about 30° C., in the dark. Generally a titration of extract must be tested in order to determine the optimal concentration for detection of specific binding interactions. FICOLL or glycerol is added, to a final concentration of about 5–7.5% and the samples loaded onto a polyacrylamide gel that is cast using low ionic strength buffers. A sample containing bromophenol blue tracking dye and FICOLL or glycerol alone is loaded in parallel. Samples are electrophoresed until the bromophenol blue has run at least a few inches into the gel. The gel apparatus is disassembled and the green fluorescent bands directly observed following illumination using 254 nm or 300 nm UV light. Extracts containing sequence-specific binding factors that recognize the template of interest will yield bands of shifted mobility with respect to other extracts and the combination of such extracts with the control DNA template.

Example 32. Preparation and use of prelabeled marker DNA

Bacteriophage lambda DNA is digested with Hind III restriction endonuclease under standard conditions. The digested DNA is then extracted with an equal volume of 24:24:1 phenol:chloroform:isoamyl alcohol to remove nucleases. The DNA is precipitated by the addition of NaCl to a concentration of 0.2M followed by 2.5 volumes of cold ethanol. The DNA is pelleted by centrifugation, washed with 70% ethanol to remove salts, dried briefly and resuspended in a small volume of 10 mM Tris-HCl, pH 8.0, 1mM EDTA. Dye 1114 is added to a final dye:bp ratio of 1:30 and the samples incubated for at least 5 minutes at room temperature, protected from light. Labeled DNA is stored at 4° C., protected from light. For use, about 50 ng of total DNA is used per gel lane. An equal volume of 15% FICOLL is added to each sample and electrophoresis carried out under standard conditions, in the dark. Green fluorescent DNA bands are visualized either during or after electrophoresis using a handhold 254 nm UV light source or a trans or epi-illuminator, or a laser scanner with ~490 nm excitation light and ~530 nm collection filters. Some bands are visible in the presence of ordinary fluorescent room light alone. The position of the bands indicates the distance that the samples have migrated and can be used to determine the size of other DNA molecules that are electrophoresed in tandem on the same gel.

Example 33. Detection of ribosomal RNA in sucrose gradients

Mammalian cells are grown under standard conditions. RNA is prepared using standard protocols. Cells are collected by centrifugation, washed with ice cold PBS (phosphate buffered saline) and pelleted again. Cells are lysed by resuspension in 10–20 cell volumes of 0.14M NaCl, 1.5 mM $MgCl_2$, 10 mM Tris-HCl, pH 8.0, 0.5% NONIDET P-40 detergent, 1 mM dithiothreitol containing 1000 units/mL placental RNase inhibitor. To the suspension is added an equal volume of 0.2M Tris-HCl, pH 8.0, 25 mM EDTA, 0.3M NaCl, and 2% SDS. The solution is vortexed rapidly or mixed with a sterile rubber policeman, if the cells are adherent. Cellular DNA is sheared by drawing the resulting viscous solution repeatedly through a 21 gauge needle using a syringe. Proteinase K is added to a final concentration of 200 µg/mL, and the solution is mixed and incubated for 30 minutes at 37° C. The proteins are removed by phenol/chloroform extraction. Nucleic acids are precipitated with 2.5 volumes of ethanol and resuspended in 50 mM Tris-HCl, pH8.0, 1 mM EDTA. DNA is removed by incubation with DNase I at a final concentration of 2 µg/mL in the presence of 10 mM $MgCl_2$, 0.1 mM dithiothreitol and 1000 units/mL placental RNase inhibitor. The solution is brought to 10 mM EDTA and 0.2% SDS to inhibit nucleases and then extracted again with phenol and chloroform. The RNA is precipitated with 2.5 volumes of ethanol. in the presence of 0.3M sodium acetate. The RNA is then resuspended in a small volume of sterile 1 mM Tris-HCl, pH 8.0, 1 mM EDTA. A gradient of sucrose (10–40% w/v) is prepared in a buffer containing 20 mM Tris-Cl, pH 8.0, 5 mM EDTA, and 1 µM Dye 1004 in polypropylene centrifuge tubes. In a volume of 0.5 mL or less, the nucleic acids are carefully layered on top of the gradient. Gradients are kept protected from light. The tubes are loaded into a Beckman SW28 (or equivalent) rotor and centrifuged at 26,000 rpm for 24 hours at 15° C. The tubes are carefully removed from the rotor and the nucleic acids visualized as brightly green fluorescent bands using a handhold UV lamp. Ribosomal RNA's are visible as three independently migrating species; the most rapid is the 23S, the next is the 16S and the slowest are the 5S species, and tRNA's. Nucleic acids can be collected by piercing the bottom of the gradient, using a 21 gauge needle. Small (0.5 mL) fractions are collected and aliquots of each analyzed by gel electrophoresis in comparison with RNA's of known size.

Example 34. Counterstaining fixed tissue culture cells that have been probed with an additional detection reagent Mouse fibroblast cells (NIH 3T3) are grown under standard conditions. Cell media is removed and the cells washed briefly with HBSS (Hanks balanced salt solution with magnesium and calcium). Cells are fixed with 3.7% formaldehyde in HBSS and washed three times more with PBS. Cells are permeabilized with 0.1% TRITON X-100 in PBS, with agitation for 5 minutes. Cells are rinsed three times with PBS, blocked by incubation with 2% fetal calf serum, 0.1% Tween 20 in PBS for 30 minutes to an hour. A rabbit antibody directed against Golgi membranes is applied in blocking solution, for one hour. Cells are rinsed in PBS and then incubated with an anti-rabbit secondary antibody that has been conjugated to TEXAS RED (diluted in blocking buffer), then washed again in PBS. To counterstain, a solution containing 0.4–0.01 µM Dye 1114 or Dye 937 is applied to the cells and they are incubated for 10 minutes at room temperature. Cells are washed briefly in PBS and visualized with a fluorescence microscope and standard fluorescein filters to visualize counterstaining and through a TEXAS RED filter set to visualize Golgi staining. Nuclei show bright green fluorescence and the cytoplasm appears slightly dimmer green.

Example 35. Staining cells in tissue

Cryosections of zebrafish heads are allowed to warm to room temperature. A solution of Dye 937 in the concentration range of 0.01–1 µM is applied in PBS. The tissue is incubated for 10 minutes at room temperature, washed briefly in PBS and then visualized through a fluorescein filter set using a fluorescence microscope. The nuclei of stained cells appear bright green, while the cytoplasm shows no staining.

Example 36. Detection and quantitation of DNA amplification products

Primers specific for targets to be amplified are prepared synthetically. Primers can contain hapten or fluorophore labels on their 5' ends, such as biotin, dinitrophenyl, a fluorescein fluorophore, a BODIPY FL fluorophore, a BODIPY TMR fluorophore, or a BODIPY TR fluorophore. These labeled primers are available commercially (Molecular Probes, Eugene Oreg.), or the labels can be added during synthesis using modified phosphoramidites, or after synthesis using amine or phosphate-reactive dyes. The presence of such labels does not significantly interfere with DNA amplification or with subsequent analysis on gels or in solution. Target DNA-containing samples are combined with primer pairs in the presence of appropriate buffers and samples are amplified according to optimal conditions for each primer pair. Such conditions must be determined empirically. DNA amplification products are then detected by either loading aliquots of samples onto agarose or polyacrylamide gels followed by staining as described in Example 21, or by a solution assay as described in Example 23. The amount of the DNA amplification product present at the end of the amplification reaction is a direct indicator of the amount of target present in the original sample, thus it can be used to assay target number, even when such numbers are too low to assay by direct application of the technique described in Example 23. The enhanced sensitivity of the present dyes also allows analysis of amplification products after fewer amplification cycles. This procedure is illustrated schematically in FIG. 2.

Example 37. Detection of single-strand conformation polymorphisms

DNA amplification products with sizes ranging from 100–250 base pairs, containing sections of human p53 and K-ras genes are prepared from human gastric adenocarcinomas as described by Perkins, et al. (NUCLEIC ACIDS RESEARCH, 21, 3637 (1993)). About 20–100 ng of the DNA amplification products, in a volume of 5 µL, is mixed with 0.4 µL of 1M methylmercury hydroxide, 1 µL of 15% FICOLL and 13.6 µL of TBE buffer. The mixture is heated to 85° C. for 4 minutes and then quickly chilled on ice. A 20% polyacrylamide gel prepared using TBE buffer, pre-equilibrated at a set temperature (which must be determined empirically for each sample) and the samples loaded onto the gel along with a sample containing only FICOLL and tracking dye. The gel is electrophoresed under constant temperature control until the marker dye is close to the bottom of the gel. The gel is stained with a 1 µM solution of Dye 937 in TBE as described in Example 21 and visualized using 254 nm–300 nm UV illumination. DNA molecules that differ in sequence appear as bands with distinct separate mobilities. The presence of bands with different mobilities is therefore indicative of even single point mutations in the target genes.

Example 38. Determination of superhelical state by gel electrophoresis

Closed circular DNA is prepared using standard procedures. Samples of closed circular DNA and size marker DNA samples are applied to a series of 0.7% agarose minigels containing dyes in the concentration range of 0.01 µM to about 1 µM. Samples are electrophoresed until the circular forms have migrated at least half of the length of the gels. Gels are then visualized directly using ultraviolet illumination or are poststained with Dye 937 and then visualized, as described in Example 21. Closed circular samples generally contain both supercoiled and relaxed DNA molecules. Treatment with enzymes such as topoisomerases or gyrases can change the topological characteristics of closed circular DNA, such as the number of supercoils present in a given molecule. If intercalating dyes such as ethidium bromide are bound to templates with negative supercoils versus relaxed DNA molecules, more dye molecules bind to the negatively supercoiled template than to the relaxed molecule. In addition, as negatively supercoiled DNA is titrated with ethidium bromide, the molecule passes from a negatively supercoiled form to relaxed DNA and then finally becomes positively supercoiled. These three different topological forms are characterized by their migration in electrophoretic gels. In general, supercoiled DNA's migrate more rapidly than identically sized relaxed molecules or linear DNA's. There is a critical concentration of ethidium bromide that induces the change from negatively supercoiled to relaxed to positively supercoiled DNA. This concentration for ethidium bromide occurs at about 0.1 to 0.5 µg/mL dye. The dyes of the present invention, such as Dye 937 can also cause this change in topological form. Since these dyes allow detection of much less DNA in a band on a gel, they provide a much more sensitive assay than do dyes such as ethidium bromide for this application. In addition, the new dyes can be used in combination with ethidium bromide, as sensitive poststains. Thus Dye 937 can be used to probe the topological state of closed circular DNA molecules and can therefore be used to assay topoisomerase or gyrase activity on such templates.

Example 39. Labels for microinjection of DNAs

Plasmid DNA is labeled with Dye 1114 by incubation for at least five minutes at room temperature, protected from light, with a solution containing no more than 1 dye molecule per 5 base pairs of DNA. DNA is microinjected into cells using standard techniques (Noueiry et al., CELL, 76, 925 (1994)). Labeled DNA appears as bright green fluorescence in cells, using a fluorescence microscope fitted with a fluorescein filter set.

Example 40. Labeling and detection of single DNA molecules

Individual phage lambda DNA molecules are tethered to microscope slides by either tethering one end through biotin/streptavidin linkages or polylysine spread binding (Perkins et al. SCIENCE 264, 822 (1994); Perkins et al., SCIENCE, 264, 819 (1994)). A solution containing 10 µM Dye 937 in TE, with 2% β-mercaptoethanol is applied to the slide. Coverslips are mounted in the presence of the dye staining solution and a mounting medium. Single stained DNA molecules can be observed in the fluorescence microscope with a standard fluorescein optical filter set. Molecules can be spread or stretched using optical tweezers (Perkins et al. and Perkins et al. supra; Bensimon et al., SCIENCE 265, 2096 (1994)). Single nucleic acid molecules can also be detected and sized in a flow cytometer following staining with this dye, in a manner analogous to that used for staining with TOTO-1 nucleic acid stain (Goodwin et al., NUCLEIC ACIDS RESEARCH 21, 803 (1993); Castro et al., ANAL. CHEM. 65, 849 (1963)).

Example 41. Quantitation of cell number

Tissue culture cells are grown under standard conditions. Cells are harvested by centrifugation for nonadherent cells and by trypsinization followed by centrifugation and washing in PBS for adherent cells. Cell pellets are lysed by suspension in 100 µL of a solution of 0.1% TRITON X-100 detergent in water. Cell lysates are diluted to 1 mL with TBE and then added directly to 1 mL of a 0.8 µM solution of Dye 993 in TBE and mixed. Samples are incubated about 5 minutes in the dark and then fluorescence at 520 nm is measured following excitation at 485 nm using a standard fluorometer. The intensity of the fluorescence emission is directly proportional to the amount of double-stranded DNA present, which is directly proportional to the cell number, as shown in Table 10 below. Fluorescence emission is compared directly with a standard curve made from known amounts of DNA (as described in Example 23, FIG. 3) to determine the amount of DNA present and is compared with results from a standard curve prepared with known quantities of the identical type of cell in order to directly assay for cell number. While the dynamic range of this assay is exceptionally large, as shown in FIG. 5A, as few as 5–10 cells can be detected using this procedure, as shown in FIG. 5B). The dyes can also be used in this way to assay reagents, drugs or hormones that either inhibit or enhance cell proliferation.

TABLE 10

Relationship between cell number and DNA content

| Cell Type | Cells/mL | DNA equivalent/mL | DNA/cell |
|---|---|---|---|
| NIH/3T3 cells | 50,000 | offscale | nd |
| | 5,000 | 100 ng/mL | 20 pg/cell |
| | 500 | 10 ng/mL | 20 pg/cell |
| | 50 | 0.9 ng/mL | 18 pg/cell |
| | 25 | 0.4 ng/mL | 16 pg/cell |
| P3X cells | 50,000 | offscale | nd |
| | 5,000 | 50 ng/mL | 11 pg/cell |
| | 500 | 5.5 ng/mL | 11 pg/cell |
| | 50 | 0.7 ng/mL | 14 pg/cell |
| | 25 | 0.34 ng/mL | 14 pg/cell |

Example 42. Discrimination of RNA, ds DNA and ss DNA using nucleases in combination with fluorescent dyes Samples containing either RNA, double-stranded DNA or single-stranded or combinations of these nucleic acids in concentrations of about 100 pg/mL to about 1 µg/mL are incubated independently with the following reagents: a) DNase I (which digests double-stranded DNA), b) RNase A and T1 Nuclease (which digest RNA), c) mung bean nuclease (which digests single-stranded DNA) or d) RNase H (which digests DNA/RNA hybrids and some double-stranded RNA's) in the presence of the appropriate buffer for each enzyme. In addition, control samples that are not subjected to enzymatic digestion are prepared. After digestion is allowed to go to completion, samples are added to cuvettes containing 0.4–0.8 µM of a dye of the present invention, such as Dye 993 or Dye 309; samples are then mixed and incubated 5 minutes in the dark. Fluorescence intensity is measured in a fluorometer. The type of nucleic acid present in the sample is determined using Table 11. If a sample yields fluorescence (indicated by+ in the table) equal to the amount yielded by the undigested control, then it does not primarily consist of the nucleic acid targeted by the enzyme. This set of data can be used to determine the amount of each species of nucleic acid present in a mixed sample, using standard curves generated with pure double-stranded DNA, single-stranded DNA, RNA and RNA/DNA hybrids.

TABLE 11

Enzymatic digestion response to selected nucleases

| | DNase I | RNase I/T1 Nuclease | Mung bean nuclease | RNase H |
|---|---|---|---|---|
| double-stranded DNA | − | + | + | + |
| single-stranded DNA | + | + | − | + |
| RNA | + | − | + | + |
| DNA/RNA hybrids | + | + | + | − |

Example 43. Discrimination of ds DNA from RNA and ss DNA using fluorescent dyes

Two nucleic acid samples are prepared having concentrations of less than 0.2 µM. The fast sample is mixed with a monomethine dye of the present invention to a final concentration of 0.2 µM dye (1:1 ratio) in TE in a fluorescence cuvette. The second sample is mixed with the same dye to a final concentration of about 1 µM or higher, in TE buffer in a fluorescence cuvette. Both samples are incubated for at least 5 minutes at room temperature in the dark. A fluorescence emission spectrum is generated for each sample, following excitation at about 485 nm, using a standard fluorometer. Samples containing only double-stranded DNA yield fluorescence emission spectra with maxima in the green wavelengths, at about 500–535 nm at both dye:base ratios. Samples containing only single-stranded DNA or RNA, however, yield a fluorescence spectrum with a maximum in the green (at about 500–535 nm) only when the dye:base ratio is less than 1:1. At dye:base ratios greater than 1:1 the emission maxima for single stranded nucleic acids shifts to longer wavelengths (typically 550–580 nm).

Some of the dyes, such as Dye 937, have very low intensities for the longer wavelength emission and appear to simply lose the green fluorescence. Nucleic acids at a final concentration of 1.5 nM bases are incubated with Dye 937 at a concentration of 0.8 µM. Calf thymus DNA was used as the double-stranded molecule (ds DNA), M13 phage DNA was used for single-stranded DNA (ss DNA) and E. coli ribosomal RNA was used for RNA. The maximum emission wavelength for double-stranded DNA is at ~520 nm, but for single-stranded DNA and RNA under these conditions the peak emission is at ~550 nm (as shown in FIG. 6).

Figure 7:
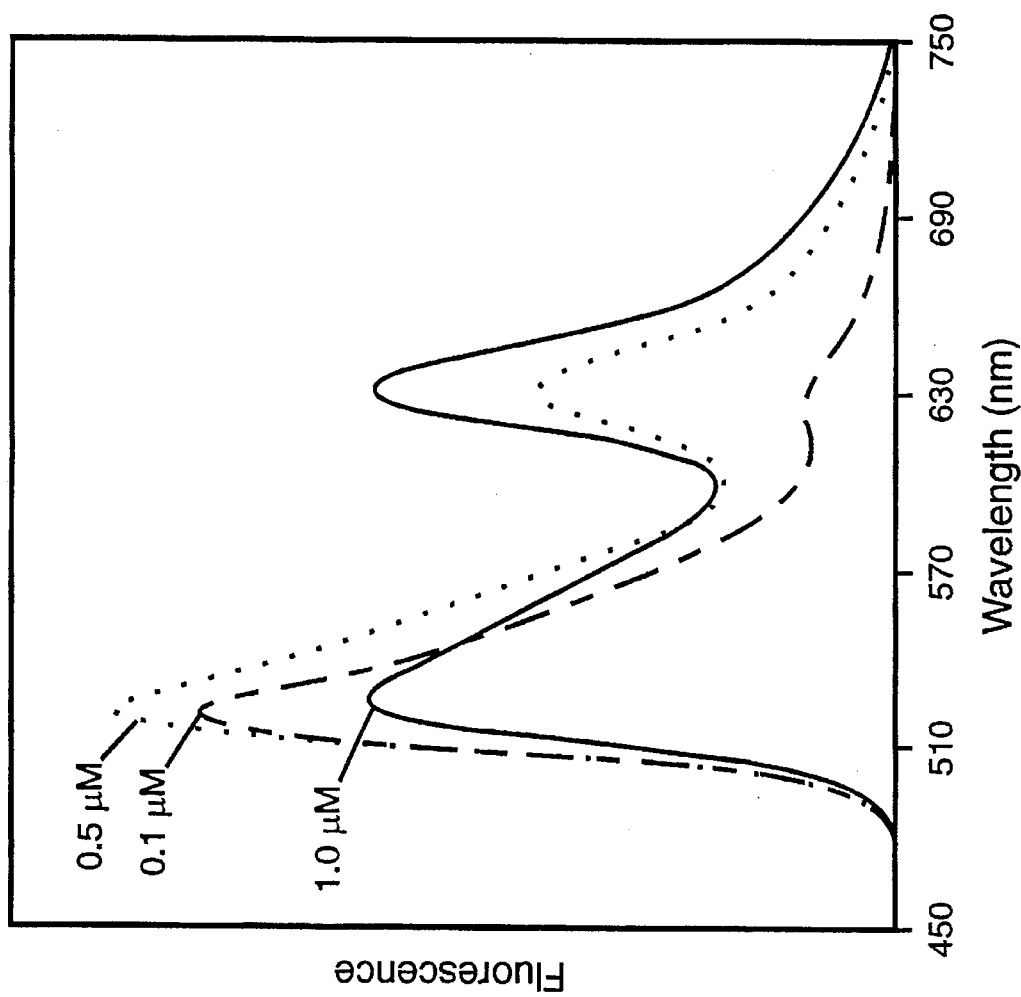
FIG. 7: Fluorescence emission as a function of dye loading, as described in Example 43.

Others, such as Dye 1114, have significant longer wavelength signals that are almost as intense as the green emission, and double-stranded and single-stranded nucleic acids can be discriminated in cells. Ethanol-killed E. coli cells are suspended in water at a concentration of ~$10^8$ cells/mL. Three bacterial suspensions are then incubated at room temperature with Dye 1114 at concentrations of 0.1 µM, 0.5 µM and 1.0 µM respectively. Following staining, the samples are illuminated at 480 nm and the fluorescence emission recorded from 490 nm to 700 nm, as shown in FIG. 7. At low staining concentrations (0.1 µM) the fluorescence response is primarily a strong green fluorescence (~520 nm). As the staining concentration increases (0.5 µM), the green fluorescence intensity increases somewhat, with an accompanying increase in red fluorescence (~630 nm). As dye concentration continues to increase (1.0 µM), the red fluorescence intensity matches the now-decreasing green fluorescence. The red fluorescence emission is due to the presence of single-stranded nucleic acids present in the stained E. coli.

Example 44. Base selectivity of several dyes

Synthetic homopolymers of ribo- or deoxyribo- nucleic acids are incubated at concentrations of 20–50 µM with Dyes 937, 1004, 993, 309, 396, 410, respectively, at concentrations of about 1 µM in TE, for about 5 minutes, at room temperature, in the dark. Fluorescence emission at about 500–530 nm is measured in a fluorometer for each sample following excitation at 485 nm. Certain of the dyes show pronounced selectivity in fluorescence according to the nature of the homopolymer as shown in Table 12. Thus these dyes can be used in combination with other dyes, such as Hoechst 33258 (which is AT selective) to determine information about primary nucleic acid structure.

TABLE 12

| POLYMER | Base selectivity of selected dyes | | | | | |
|---|---|---|---|---|---|---|
| | Dye 937 | Dye 1004 | Dye 993 | Dye 309 | Dye 396 | Dye 410 |
| ds DNA | 0.68 | 0.34 | 0.50 | 0.64 | 0.93 | 0.90 |
| poly dA/polydT | 0.68 | 0.59 | 0.67 | 0.59 | 0.81 | 0.92 |
| poly dG/poly dC | 0.59 | 0.27 | 0.35 | 0.50 | 0.86 | 0.88 |
| poly dA | 0.062 | 0.003 | 0.004 | 0.005 | 0.20 | 0.015 |
| poly dT | 0.054 | 0.015 | 0.064 | 0.13 | 0.19 | 0.28 |
| poly dC | 0.021 | 0.014 | 0.015 | 0.02 | 0.056 | 0.045 |
| poly dI | 0.07 | 0.029 | 0.036 | 0.52 | 0.13 | 0.32 |
| poly ribo G | 0.34 | 0.36 | 0.28 | 0.36 | 0.81 | 0.90 |
| poly ribo C | 0.002 | 0.006 | 0.009 | 0.007 | 0.027 | 0.012 |
| poly ribo U | 0.012 | 0.009 | 0.042 | 0.071 | 0.19 | 0.097 |
| poly ribo A | 0.027 | 0.018 | 0.034 | 0.057 | 0.12 | 0.23 |

Quantum yields are shown for several dyes bound to several different nucleic acid substrates. Poly ribo G probably shows extremely high quantum yields because it has formed higher order structures such as triple-stranded molecules, rather than as a result of base selectivity. Poly dI is a polymer of inosine, which behaves much like guanine in nucleic acids.

Example 45. Determination of relative viability of bacteria in a dairy product Fresh samples of pasteurized and unpasteurized milk are obtained and refrigerated immediately. To a 1 mL aliquot of each sample 50 µL of a 60 µM stock solution of AMCA-X-WGA (in bicarbonate buffer, pH 7.1) and 5 µL of a 1 mM DMSO stock solution of Dye 352 are added. The samples are incubated at 37° C. for 5 minutes and then 5 µL of a 1 mM DMSO stock solution of Dye 314 is added. The samples are then incubated for an additional 25 minutes. 5 µL of suspension, which has been trapped between a coverglass and slide, is examined using an epifluorescence microscope equipped with a 3-band filter set (DAPI/fluorescein/TEXAS RED). Bacteria with blue surface staining (Gram positive) and without surface label (Gram negative) are discriminated as live (red fluorescent) or dead (green fluorescent).

Example 46. Detection viable bacteria in a food sample

One gram samples of ground beef are agitated with 9 mL of sterile water at medium speed in a vortexer for 1 minute. Three 0.1 mL aliquots are removed and spread uniformly over the surface of three 100 mm eosin-methylene blue plates, which are subsequently incubated for 24–48 hours at 37° C. An 800 µL aliquot is removed and 200 µL of 5% bovine serum albumin in sterile distilled water are added. 1 µL of a 5 mM DMSO solution of Dye 345 and 100 µL of a 1 mg/mL solution of rabbit anti-0157:H7 IgG are added to the sample, which is then incubated for 15 minutes at room temperature with slow mixing. The sample is then washed by centrifugation at 10,000×g for 20 sec in a 1.5 mL tube, and resuspended in 1 mL of sterile water with 4% glutaraldehyde. After 15 minutes incubation at room temperature, the bacteria are pelleted by centrifugation as above and resuspended in 1 mL of sterile water. 2 µL of a 1 mM DAPI solution in DMSO, 1 µL of 5 mM Dye 345, and 20 µL 1 mg/mL TEXAS RED fluorophore-conjugated goat anti-rabbi IgG are subsequently added and the sample is incubated for 15 min at room temperature with slow mixing. Live bacteria are blue fluorescent and dead bacteria are green fluorescent. Only enteropathogenic *E. coli* are red fluorescent.

Example 47. MIC determination of an antibiotic for bacteria using flow cytometry A culture of *E. coli* is grown to mid-log phase in nutrient broth with shaking at 37° C. The minimum inhibitory concentration (MIC) of ampicillin in the concentration range between 1 µg/mL and 10 mg/mL, in ten-fold increments, is then determined. The log-phase culture is resuspended in 6 tubes of fresh 0.2µ-filtered tryptone broth, each containing 4 mL of 2×10$^6$ cfu/mL. To each tube is added 4 mL of fresh 0.2µ-filtered tryptone broth containing a 2X concentration of ampicillin (2,20, 200, 2000, 20000 µg/mL), or tryptone broth alone (control). The suspensions are incubated for 0, 2, 4 and 6 hours and 2 mL of sample is removed at each time point. To the 2 mL sample, 2 µL of 5 mM Dye 398 is added and the suspension is incubated for 10 minutes. The distributions of the fluorescence intensities are analyzed by flow cytometry with 488 nm excitation and channel 1 (green) fluorescence emission detection. Fluorescence intensity is then plotted against the forward scatter of the bacteria for each time of incubation with ampicillin.

Example 48. In situ assessment of neutrophil bactericidal activity

The test makes use of the differential permeability of Dye 397 for mammalian cells but not for live bacteria in order to determine the viability of phagocytosed bacteria. Adherent cells, including neutrophils and macrophages, are purified from human peripheral blood. *E. coli* are grown to late log-phase in nutrient broth and opsonized with rabbit anti-*E. coli* IgG, washed into sterile water to a density of 1×10$^7$ cfu/mL, and stained by addition of 1 µL/mL of a 1 mM DMSO stock solution of Dye 314. The bacteria are stained for 15 minutes and then washed extensively to remove all traces of extracellular dye. One µL/mL of a 1 mM DMSO solution of Dye 397 is added to the phagocytes and the culture is incubated for 15 minutes. The residual dye is rinsed off with medium and fresh medium containing 1 µM Dye 397 is added. The labeled bacteria are added to the dye-loaded cells and the bactericidal activity of the phagocytes is indicated by an increase in the progression of green fluorescent staining of the intracellular bacteria, as observed in a microscope equipped with a fluorescein long-pass filter set.

Example 49. Determination of metabolic activity of bacteria using flow cytometry

*Salmonella typhimurium* are grown to mid-log phase in nutrient broth at 37° C. Bacteria are washed twice in sterile E-pure water and $1\times10^5$/mL *S. typhimurium* are inoculated into 50 mL of tryptone medium of different strengths: 100%, 10%, 1%, and 0% (pure water). After 4 hours growth at 37° C. each culture of bacteria is concentrated by centrifugation at 10,000×g for 10 minutes, and permeabilized by subsequent resuspension in 70% isopropanol for 1 hour. To an aliquot of the bacteria cultured with 100% nutrient broth is added 20 µg of heat-inactivated RNase A, and the aliquot is incubated at 37° C. for 60 minutes. All the bacterial samples are then washed twice by centrifugation and stained with Dye 1114 at a final concentration of 5 µM for 30 minutes at room temperature.

The bacterial samples are analyzed using a flow cytometer equipped with an Argon laser set at 100 mW output for the 488 nm line. The forward (low angle) light scatter is set at maximal amplification, and the acquisition trigger logic of the instrument to the fluorescence detector is set to collect light around 530 nm (the "fluorescein detector"). The signal amplification rate of said detector is set such that signals exceed the threshold level, but do not range beyond the window of the light collecting device. The top signal cluster in FIG. 8A represents logarithmically growing bacteria (cultured in 100% broth). The somewhat lower signal cluster in FIG. 8B is obtained from a culture kept at 1% nutrient broth for 3 hours. The appearance of the resulting scatter plot, relative to the 100% and 0% standards, gives a measure of the metabolic activity of the bacterial samples.

Example 50. Determination of live and dead bacteria in a biological fluid

At least 10 mL of urine are collected aseptically. Particulates including bacteria are concentrated by centrifugation and resuspended in 50 µL of 0.85% NaCl (saline solution). 25 µL of 20 µM Dye 1151 in saline solution are added and the mixture is incubated at room temperature for 10 minutes. 25 µL of DAPI in saline solution are added and the mixture is incubated for an additional 20 minutes at room temperature. Numbers of live and dead organisms are enumerated by flow cytometry using excitation at 350–360 and 488 urn, with fluorescence emission detected at 450 nm (live bacteria) and at 530 nm (dead bacteria).

Example 51. Assay of attachment of bacteria to cell surfaces

Madin-Darby Canine Kidney (MDCK) cells are cultured in 96-well plates to 70% confluence. Growth medium is removed from the wells and replaced with 100 µL of sterile physiological saline (PS, 10 mM Na HEPES, 135 mM NaCl, 5 mM KCl, 1 mM $MgCl_2$, 2 mM $CaCl_2$, 5 mM glucose, pH 7.4). A culture of 100 mL of *Salmonella typhimurium* bacteria is grown by shaking at 200 rpm in 37° C. nutrient broth to mid log-phase. The bacteria are washed by centrifugation and resuspended in PS to a density of $2\times10^7$/mL. Ten mL of the bacterial suspension is removed and killed by treatment with 70% isopropyl alcohol for 1 hour. The killed bacteria are then washed twice in PS and resuspended to the original volume. A parallel aliquot is washed twice in PS and resuspended in the same volume. Five mL of each sample are mixed together and 10 µL of 5 mM Dye 1114 is added. The mixture is incubated for 10 minutes at room temperature. Ten µL of Dye 314 is then added and the mixture is incubated for an additional 20 minutes. The stained bacterial suspension is then washed twice in PS and serially diluted 1:10 four times. In triplicate, 100 µL of each bacterial dilution, or PS alone, is added to wells in the 96-well plate containing MDCK cells. The plate is incubated at 37° C. for 20 minutes with agitation every 30 sec. All wells are then gently washed three times with PS and filled with 150 µL of PS. The green fluorescence of the wells is quantified in a multi-well fluorescence plate reader using excitation at 485 nm and emission at 520 nm; the red fluorescence is determined by excitation at 590 nm and emission at 620 nm. The relative proportions of fluorescence are compared with standard wells containing cells with different mounts of bacterial suspension.

Example 52. Detection of cells or bacteria using a flow cytometer

A sample which is suspected to contain biological structures (eg. bacteria, yeast, mammalian cells) is stained with 5 µM Dye 938 for 30 minutes at room temperature. The sample is then analyzed using a flow cytometer equipped with an Argon laser set at 100 mW output for the 488 nm line. Forward (low angle) light scatter is set at maximal amplification for bacteria and biological objects of similar size, or at a suitable lower level of signal amplification if biological objects are deemed to be larger in size. The acquisition trigger logic of the instrument on the fluorescence detector is set to collect light around 530 nm (the "fluorescein detector"). The signal amplification rate of said detector is set such that signals are beyond the threshold level, but do not exceed the range of the light collecting device. Signals are acquired from the sample under investigation and compared to data recorded using bacterial or mammalian cells as controls.

Example 53. Determination of cell membrane integrity using flow cytometry

Bacterial samples are suspended in distilled water at a density of about $6\times10^6$ bacteria per mL of water. Mammalian cells are suspended in phosphate buffered saline (PBS) at a density of about $1\times10^6$ per mL. The sample is stained with Dye 1114, a universally cell-impermeant stain. Bacterial samples are stained with 5 µM Dye 1114, mammalian cells are stained with 1–5 µM Dye 1114. After 30 minutes of incubation the sample is analyzed by flow cytometry on an instrument equipped with an Argon laser set at 100 mW output for the 488 nm line. Forward (low angle) light scatter is set at maximal amplification for bacteria and biological objects of similar size, or at a suitable lower level of signal amplification if biological objects are deemed to be larger in size. The acquisition trigger logic of the instrument on the fluorescence detector is set to collect light around 530 nm (the "fluorescein detector"). The signal amplification rate of said detector is set such that signals are beyond the threshold level, but not to exceed the range of the light collecting device. Generally, bacteria require logarithmic signal amplification, while mammalian cells can be analyzed with linear signal amplification. Signals are acquired from the sample under investigation and from control bacterial or mammalian cells. The relative amounts of viable and non-viable cells can be quantitated by comparison with the fluorescence and scatter characteristics of the control samples. The results of this experiment are shown in FIG. 9 for a 1:1 mixture of living and dead bacteria. The uppermost cluster of signals corresponds to dead bacteria, while the lowermost cluster represents viable bacteria. The inset plot of FIG. 9 shows the excellent correspondence between calculated and measured live/dead ratios. Similar results can be obtained for mammalian cells.

Example 54. Staining of fixed bacteria

*E. coli* are grown to late log-phase in nutrient broth. The bacterial sample is incubated with 5 µM Dye 1114 for 30 minutes. The bacteria are then fixed by the addition of a 4% solution of glutaraldehyde, followed by incubation for 15 minutes. The bacterial sample is then washed twice with water. Visualization of the fixed sample using a fluorescence microscope shows only the bacterial cells that were dead at the time of staining show green fluorescence.

Alternatively, the bacterial culture is fixed using 3.7% formaldehyde or 4% glutaraldehyde for 15 minutes, followed by washing twice with water. The fixed cells are then stained by incubating in a 5 μM solution of Dye 1114 for 30 minutes. Again, only the bacterial cells that were dead at the time of fixation exhibit green fluorescence.

The fixation of the bacteria produces extensive cross-linking within the cellular membranes, so that membranes that were intact at the time of fixation remain impermeable to the dead cell stain. Pathogenic bacteria can therefore be assayed for viability after fixation, reducing the risk of exposure. The use of the currently used dead stain propidium iodide, before or after fixation, produces similar results.

It is to be understood that, while the foregoing invention has been described in detail by way of illustration and example, numerous modifications, substitutions, and alterations are possible without departing from the spirit and scope of the invention as described in the following claims.

What is claimed is:

1. A compound of the formula

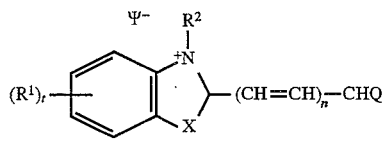

wherein
each $R^1$ is independently H; or an alkyl group having from 1–6 carbons; an alkoxy group having from 1–6 carbons; or a trifluoromethyl; or a halogen; and t=1–4;
$R^2$ is an alkyl group having 1–6 carbons;
X is O, S, Se or $NR^{15}$, where $R^{15}$ is H or an alkyl group having 1–6 carbons; or X is $CR^{16}R^{17}$ where $R^{16}$ and $R^{17}$, which may be the same or different, are independently alkyl groups having 1–6 carbons, or $R^{16}$ and $R^{17}$ taken in combination complete a five or six membered saturated ring;
n=0, 1 or 2;
$\Psi^-$ is a biologically compatible counterion;
Q has the formula Q1 or Q2

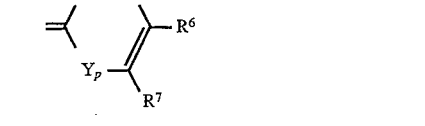

wherein
Y is $-CR^3=CR^4-$;
p and m=0 or 1, such that p+m=1;
$R^5$ is an alkyl, alkenyl, polyalkenyl, alkynyl or polyalkynyl group having 1–6 carbons; or $R^5$ is a cyclic substituent that is a substituted or unsubstituted aryl or heteroaryl; or a substituted or unsubstituted cycloalkyl having 3–10 carbons; or $R^5$ is a TAIL;

$R^3$, $R^4$, $R^6$ and $R^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or $-OR^8$, $-SR^8$, $-(NR^8R^9)$; or $-OSO_2R^{19}$; or a TAIL; where $R^8$ and $R^9$, which can be the same or different, are independently H; or alkyl groups having 1–6 carbons; or 1–2 alicyclic or aromatic rings; or $R^8$ and $R^9$ taken in combination are $-(CH_2)_4-$ or $-(CH_2)_5-$ to give a 5 or 6 membered ring; and where $R^{19}$ is alkyl having 1–6 carbons, or perfluoroalkyl having 1–6 carbons, or aryl;
or $R^6$ and $R^7$, taken in combination are $-(CH_2)_v-$ where v=3 or 4, or $R^6$ and $R^7$ form a fused aromatic ring according to formula Q2;
$R^{11}$, $R^{12}$, $R^{13}$, and $R^{14}$, which may be the same or different, are independently H; or an alkyl, alkenyl, polyalkenyl, alkynyl or polyalkynyl group having 1–6 carbons; or a halogen; or a TAIL; or $-OH$, $-OR^8$, $-SR^8$, or $-(NR^8R^9)$;
TAIL is a heteroatom-containing moiety having the formula LINK-SPACER-CAP;
wherein
LINK is a single covalent bond, $-O-$, $-S-$, or $-NR^{20}-$; where $R^{20}$ is H, a linear or branched alkyl having 1–8 carbons, or $R^{20}$ is $-SPACER'-CAP'$;
SPACER and SPACER', which may be the same or different, are covalent linkages, linear or branched, cyclic or heterocyclic, saturated or unsaturated, each having 1–16 nonhydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds;
CAP and CAP', which may be the same or different, are $-O-R^{21}$, $-S-R^{21}$, $-NR^{21}R^{22}$, or $-N^+R^{21}R^{22}R^{23}\Psi^-$;
wherein
$R^{21}$, $R^{22}$, and $R^{23}$ are independently H, or a linear or branched alkyl or cycloalkyl having 1–8 carbons, optionally further substituted by hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\Psi^-$ is a biologically compatible counterion;
or
CAP and CAP' are independently

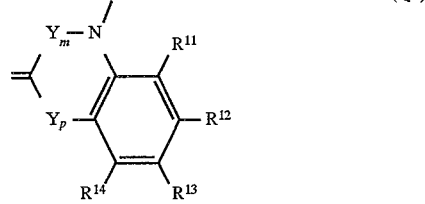

-continued

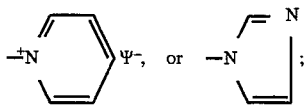

where $R^{21}$, $R^{22}$ and $\Psi^-$ are as defined previously;
such that at least one of $R^3$, $R^4$, $R^5$, $R^6$, $R^7$, $R^{11}$, $R^{12}$, $R^{13}$, and $R^{14}$ is a TAIL; and when $R^5$ is a TAIL, LINK is a single bond; and where only $R^5$ is a TAIL, $R^3$ or $R^4$ is not hydrogen; and, where more than one of $R^2$, $R^3$, $R^4$, $R^5$, $R^6$, $R^7$, $R^{11}$, $R^{12}$, $R^{13}$, and $R^{14}$ is a TAIL, each TAIL is optionally the same or different.

2. A compound, as claimed in claim 1, wherein each $R^1$ is H, and $R^2$ is ethyl or methyl.

3. A compound, as claimed in claim 1, wherein X is O or S.

4. A compound, as claimed in claim 1, wherein n=0 or 1.

5. A compound, as claimed in claim 1, wherein at least one of $R^3$, $R^4$, $R^5$, $R^6$, $R^7$, $R^{11}$, $R^{12}$, $R^{13}$, and $R^{14}$ is a substituted or unsubstituted naphthyl, phenyl, thienyl, or cycloalkyl having 3–8 carbons.

6. A compound, as claimed in claim 1, wherein neither CAP nor CAP' is —O—$R^{21}$ or —S—$R^{21}$.

7. A compound, as claimed in claim 1, wherein CAP and CAP', which may be the same or different, are —$NR^{21}R^{22}$, or —$N^+R^{21}R^{22}R^{23}\Psi^-$, wherein $R^{21}$, $R^{22}$, and $R^{23}$ are independently H, or a linear or branched alkyl or cycloalkyl having 1–8 carbons.

8. A compound, as claimed in claim 1, wherein $R^{20}$ is H or a linear or branched alkyl having 1–8 carbons.

9. A compound, as claimed in claim 1, wherein SPACER and SPACER' are independently linear alkylenes having 1–8 carbons.

10. A compound, as claimed in claim 1, wherein SPACER and SPACER' are the same, and CAP and CAP' are the same.

11. A compound, as claimed in claim 1, of the formula

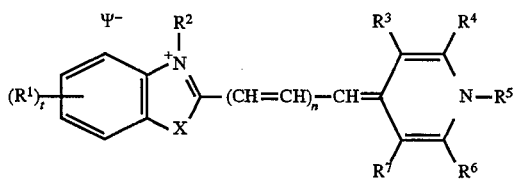

or of the formula

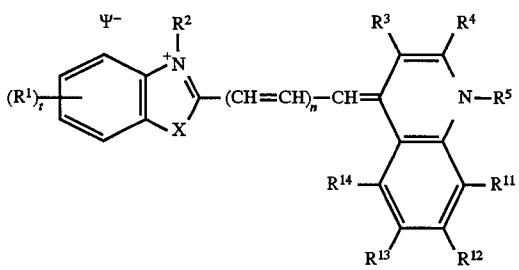

12. A compound, as claimed in claim 11, wherein $R^4$ is a TAIL.

13. A compound, as claimed in claim 11, wherein $R^5$ is a substituted or unsubstituted naphthyl, phenyl, thienyl, or cycloalkyl having 3–8 carbons.

14. A compound, as claimed in claim 11, wherein $R^5$ is phenyl or substituted phenyl.

15. A compound, as claimed in claim 13, wherein each of $R^3$, $R^6$, and $R^7$ is hydrogen.

16. A compound as claimed in claim 13, wherein each of $R^3$, $R^{11}$, $R^{12}$, $R^{13}$ and $R^{14}$ is hydrogen.

17. A compound, as claimed in claim 11, wherein $R^5$ is a linear or branched alkyl having 1–6 carbons.

18. A compound, as claimed in claim 11, wherein $R^5$ is a TAIL and $R^4$ is not hydrogen.

19. A compound of the formula

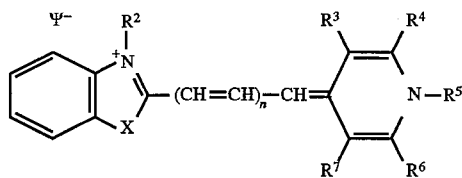

or having the formula

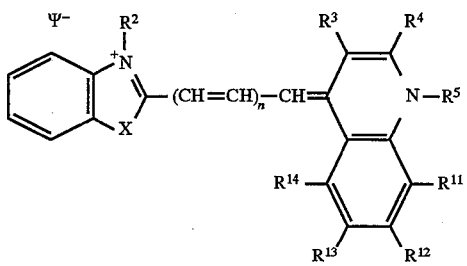

wherein
$R^2$ is an alkyl group having 1–6 carbons;
X is O or S;
n=0, 1 or 2;
$\Psi^-$ is a biologically compatible counterion;
$R^5$ is a substituted or unsubstituted naphthyl, phenyl, thienyl, or cycloalkyl having 3–8 carbons;
$R^4$ is an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —$(NR^8R^9)$; or —$OSO_2R^{19}$; or a TAIL; where $R^8$ and $R^9$, which can be the same or different, are independently H; or alkyl groups having 1–6 carbons; or 1–2 alicyclic or aromatic rings; or $R^8$ and $R^9$ taken in combination are —$(CH_2)_4$— or —$(CH_2)_5$— to give a 5 or 6 membered ring; and where $R^{19}$ is alkyl having 1–6 carbons, or perfluoroalkyl having 1–6 carbons, or aryl; having 1–6 carbons, or aryl;
$R^3$, $R^6$ and $R^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —$(NR^8R^9)$; or —$OSO_2R^{19}$; or a TAIL;
$R^{11}$, $R^{12}$, $R^{13}$, and $R^{14}$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–8 carbons; or a TAIL; or —$OR^8$, —$SR^8$, or —$(NR^8R^9)$;
TAIL is a heteroatom-containing moiety having the formula LINK-SPACER-CAP;
wherein
LINK is a single covalent bond, —O—, —S—, or —$NR^{20}$—; where $R^{20}$ is H, a linear or branched alkyl having 1–8 carbons, or $R^{20}$ is —SPACER'—CAP';
SPACER and SPACER', which may be the same or different, are covalent linkages, linear or branched, cyclic or heterocyclic, saturated or unsaturated, each having 1–16 nonhydrogen atoms selected from the group consisting of C, N, O and S, such that the linkage begins and ends with a carbon atom, and contains any combination of ether, thioether, amine, ester, amide, or aliphatic, oleic or aromatic carbon-carbon bonds, or aromatic carbon-nitrogen or nitrogen-nitrogen bonds; wherein all heteroatoms in the linear backbone of SPACER are separated by at least two carbon atoms;

CAP and CAP', which may be the same or different, are $-O-R^{21}$, $-S-R^{21}$, $-NR^{21}R^{22}$, or $-N^+R^{21}R^{22}R^{23}\Psi^-$;
wherein $R^{21}$, $R^{22}$, and $R^{23}$ are independently H, or a linear or branched alkyl or cycloalkyl having 1–8 carbons, optionally further substituted by halogen, hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\Psi^-$ is a biologically compatible counterion;

or

CAP and CAP' are independently

[chemical structures]

where $R^{21}$, $R^{22}$ and $\Psi^-$ are as defined previously;

such that at least one of $R^3$, $R^4$, $R^6$, $R^7$, $R^{11}$, $R^{12}$, $R^{13}$, and $R^{14}$ is a TAIL; and, where more than one substituent is a TAIL, each TAIL is optionally the same or different.

20. A compound, as claimed in claim 19, wherein $R^4$ is a TAIL.

21. A compound having the formula

[chemical structure]

or having the formula

[chemical structure]

wherein
$R^2$ is an alkyl group having 1–6 carbons;
X is O or S;
n=0, 1 or 2;
$\Psi^-$ is a biologically compatible counterion;
$R^5$ is an alkyl having 1–6 carbons;
$R^4$ is an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or $-OR^8$, $-SR^8$, $-(NRR^9)$; or $-OSO_2R^{19}$; or a TAIL; where $R^8$ and $R^9$, which can be the same or different, are independently H; or alkyl groups having 1–6 carbons; or 1–2 alicyclic or aromatic rings; or $R^8$ and $R^9$ taken in combination are $-(CH_2)_4-$ or $-(CH_2)_5-$ to give a 5 or 6 membered ring; and where $R^{19}$ is alkyl having 1–6 carbons, or perfluoroalkyl having 1–6 carbons, or aryl; having 1–6 carbons, or aryl;
$R^3$, $R^6$ and $R^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or $-OR^8$, $-SR^8$, $-(NR^8R^9)$; or $-OSO_2R^{19}$; or a TAIL;
$R^{11}$, $R^{12}$, $R^{13}$, and $R^{14}$, which may be the same or different, are independently H; or an alkyl, alkenyl polyalkenyl, alkynyl or polyalkynyl group having 1–6 carbons; or a halogen; or a substituted or unsubstituted aryl or heteroaryl; or a substituted or unsubstituted cycloalkyl having 3–8 carbons; or a TAIL; or $-OR^8$, $-SR^8$, or $-(NR^8R^9)$;
TAIL is a heteroatom-containing moiety having the formula LINK-SPACER-CAP;
wherein
LINK is a single covalent bond, $-O-$, $-S-$, or $-NR^{20}-$; where $R^{20}$ is H, a linear or branched alkyl having 1–8 carbons, or $R^{20}$ is $-SPACER'-CAP'$;
SPACER and SPACER', which may be the same or different, are covalent linkages, linear or branched, cyclic or heterocyclic, saturated or unsaturated, each having 1–16 nonhydrogen atoms selected from the group consisting of C, N, O and S, such that the linkage begins and ends with a carbon atom, and contains any combination of ether, thioether, amine, ester, amide, or aliphatic, olefinic or aromatic carbon-carbon bonds, or aromatic carbon-nitrogen or nitrogen-nitrogen bonds; wherein all heteroatoms in the linear backbone of SPACER are separated by at least two carbon atoms;

CAP and CAP', which may be the same or different, are $-O-R^{21}$, $-S-R^{21}$, $-NR^{21}R^{22}$, or $-N^+R^{21}R^{23}\Psi^-$;
wherein
$R^{21}$, $R^{22}$, and $R^{23}$ are independently H, or a linear or branched alkyl or cycloalkyl having 1–8 carbons, optionally further substituted by halogen, hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\Psi^-$ is a biologically compatible counterion;

or

CAP and CAP' are independently

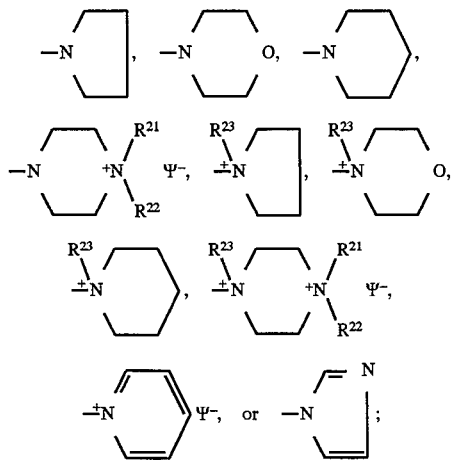

where $R^{21}$, $R^{22}$ and $\Psi^-$ are as defined previously; such that at least one of $R^3$, $R^4$, $R^6$, $R^7$, $R^{11}$, $R^{12}$, $R^{13}$, and $R^{14}$ is a TAIL; and, where more than one substituent is a TAIL, each TAIL is optionally the same or different.

22. A compound having the formula

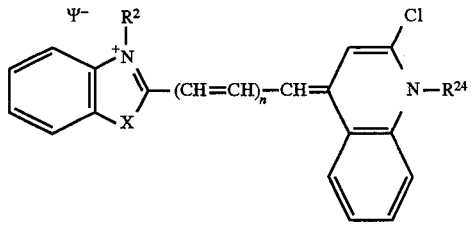

wherein $R^2$ and $R^{24}$ are independently a linear or branched alkyl having 1–6 carbons;

X is O, S, Se or $NR^{15}$, where $R^{15}$ is H or an alkyl group having 1–6 carbons; or X is $C(CH_3)_2$;

n=0, 1 or 2; and $\Psi^-$ is a biologically compatible counterion.

23. A fluorescent complex comprising a nucleic acid polymer non-covalently bound to one or more dye molecules of the formula

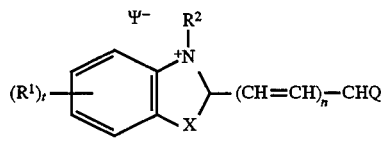

wherein each $R^1$ is independently H; or an alkyl group having from 1–6 carbons; an alkoxy group having from 1–6 carbons; or a trifluoromethyl; or a halogen; and t=1–4;

$R^2$ is an alkyl group having 1–6 carbons;

X is O, S, Se or $NR^{15}$, where $R^{15}$ is H or an alkyl group having 1–6 carbons; or X is $CR^{16}R^{17}$ where $R^{16}$ and $R^{17}$, which may be the same or different, are independently alkyl groups having 1–6 carbons, or $R^{16}$ and $R^{17}$ taken in combination complete a five or six membered saturated ring;

n=0, 1 or 2;

$\Psi^-$ is a biologically compatible counterion;

Q has the formula Q 1 or Q2

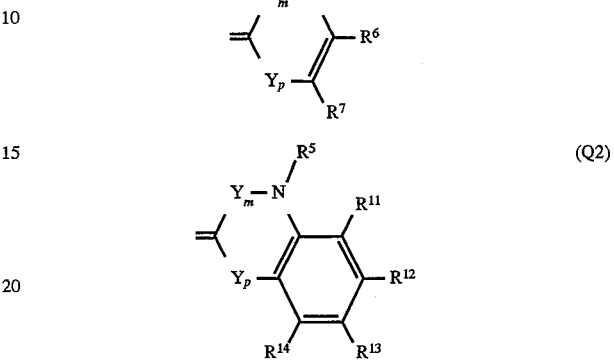

wherein

Y is $-CR^3=CR^4-$;

p and m=0 or 1, such that p+m=1;

$R^5$ is an alkyl, alkenyl, polyalkenyl, alkynyl or polyalkynyl group having 1–6 carbons; or $R^5$ is a substituted or unsubstituted aryl or heteroaryl; or a substituted or unsubstituted cycloalkyl having 3–10 carbons; or $R^5$ is a TAIL;

$R^3$, $R^4$, $R^6$ and $R^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or $-OR^8$, $-SR^8$, $-(NR^8R^9)$; or $-OSO_2R^{19}$; or a TAIL; where $R^8$ and $R^9$, which can be the same or different, are independently H; or alkyl groups having 1–6 carbons; or 1–2 alicyclic or aromatic rings; or $R^8$ and $R^9$ taken in combination are $-(CH_2)_4-$ or $-(CH_2)_5-$ to give a 5 or 6 membered ring; and where $R^{19}$ is alkyl having 1–6 carbons, or perfluoroalkyl having 1–6 carbons, or aryl;

or $R^6$ and $R^7$, taken in combination are $-(CH_2)_v-$ where v=3 or 4, or $R^6$ and $R^7$ form a fused aromatic ring according to formula Q2;

$R^{11}$, $R^{12}$, $R^{13}$, and $R^{14}$, which may be the same or different, are independently H; or an alkyl, alkenyl, polyalkenyl, alkynyl or polyalkynyl group having 1–6 carbons; or a halogen; or a TAIL; or $-OH$, $-OR^8$, $-SR^8$, or $-(NR^8R^9)$;

TAIL is a heteroatom-containing moiety having the formula LINK-SPACER-CAP;

wherein

LINK is a single covalent bond, $-O-$, $-S-$, or $-NR^{20}-$; where $R^{20}$ is H, a linear or branched alkyl having 1–8 carbons, or $R^{20}$ is $-SPACER'-CAP'$;

SPACER and SPACER', which may be the same or different, are covalent linkages, linear or branched, cyclic or heterocyclic, saturated or unsaturated, each having 1–16 nonhydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds;

CAP and CAP', which may be the same or different, are $-O-R^{21}$, $-S-R^{21}$, $-NR^{21}R^{22}$, or $-N^+R^{21}R^{22}R^{23}\Psi^-$;

wherein
$R^{21}$, $R^{22}$, and $R^{23}$ are independently H, or a linear or branched alkyl or cycloalkyl having 1–8 carbons, optionally further substituted by hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\Psi^-$ is a biologically compatible counterion;
CAP and CAP' are independently

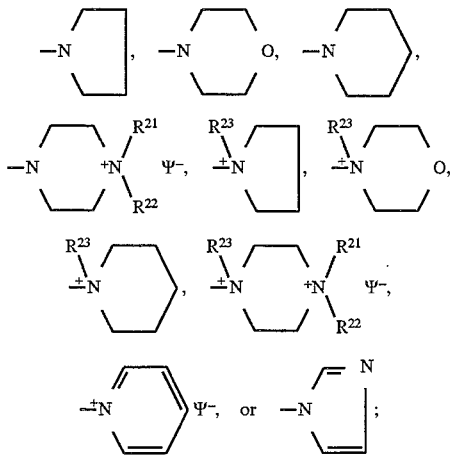

where $R^{21}$, $R^{22}$ and $\Psi^-$ are as defined previously; such that at least one of $R^3$, $R^4$, $R^5$, $R^6$, $R^7$, $R^{11}$, $R^{12}$, $R^{13}$, and $R^{14}$ is a TAIL, and when $R^5$ is a TAIL, LINK is a single bond; and where only $R^5$ is a TAIL, $R^3$ or $R^4$ is not hydrogen; and, where more than one of $R^2$, $R^3$, $R^4$, $R^5$, $R^6$, $R^7$, $R^{11}$, $R^{12}$, $R^{13}$, and $R^{14}$ is a TAIL, each TAIL is optionally the same or different.

24. A fluorescent complex, as claimed in claim 23, wherein each $R^1$ is;
$R^2$ is ethyl or methyl;
m=1;
$R^4$ is not hydrogen;
$R^5$ is alkyl having 1–6 carbons; or a cyclic substituent that is a substituted or unsubstituted aryl or heteroaryl; or a substituted or unsubstituted cycloalkyl having 3–10 carbons; or $R^5$ is a TAIL; and
SPACER and SPACER', which may be the same or different, are covalent linkages, linear or branched, cyclic or heterocyclic, saturated or unsaturated, each having 1–16 nonhydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds.

25. A fluorescent complex, as claimed in claim 24, wherein
X is O or S;
n=0 or 1; and
$R^5$ is alkyl having 1–6 carbons, or a cyclic substituent.

26. A fluorescent complex, as claimed in claim 24 wherein at least one of $R^3$, $R^4$, $R^5$, $R^6$, $R^7$, $R^{11}$, $R^{12}$, $R^{13}$, and $R^{14}$ is a substituted or unsubstituted naphthyl, phenyl, thienyl, or cycloalkyl having 3–8 carbons.

27. A fluorescent complex, as claimed in claim 24, wherein neither CAP nor CAP' is —O—$R^{21}$ or —S—$R^{21}$.

28. A fluorescent complex, as claimed in claim 23, wherein the nucleic acid polymer is a chromosome.

29. A fluorescent complex, as claimed in claim 23, wherein the nucleic acid polymer is a natural or synthetic oligonucleotide.

30. A fluorescent complex, as claimed in claim 23, wherein said complex is enclosed in a biological structure.

31. A fluorescent complex, as claimed in claim 23, wherein said complex is present in an aqueous or aqueous miscible solution.

32. A fluorescent complex, as claimed in claim 23, wherein said complex is present in an electrophoretic matrix.

33. A fluorescent complex, as claimed in claim 23, wherein said complex is present in a flowing medium.

34. A fluorescent complex, as claimed in claim 23, wherein the nucleic acid polymer comprises modified nucleic acid bases or links.

35. A method of staining nucleic acids, comprising
a) combining a sample that contains or is thought to contain a nucleic acid, with a mixture containing a dye compound of the formula (formula I):

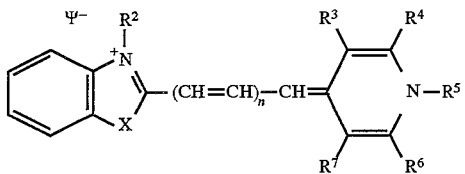

or having the formula

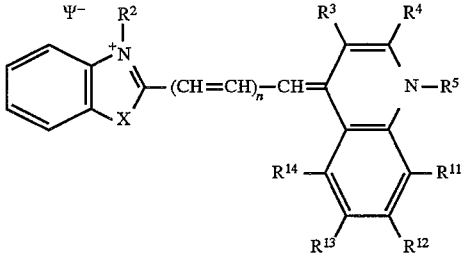

wherein
$R^2$ is ethyl or methyl;
X is O or S;
n=0, 1 or 2;
$\Psi^-$ is a biologically compatible counterion;
$R^5$ is alkyl having 1–6 carbons; or a cyclic substituent that is a substituted or unsubstituted aryl or heteroaryl; or a substituted or unsubstituted cycloalkyl having 3–10 carbons; or $R^5$ is a TAIL;
$R^4$ is an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —($NR^8R^9$); or —$OSO_2R^{19}$; or a TAIL; where $R^8$ and $R^9$, which can be the same or different, are independently H; or alkyl groups having 1–6 carbons; or 1–2 alicyclic or aromatic rings; or $R^8$ and $R^9$ taken in combination are —$(CH_2)_4$— or —$(CH_2)_5$— to give a 5 or 6 membered ring; and where $R^{19}$ is alkyl having 1–6 carbons, or perfluoroalkyl having 1–6 carbons, or aryl; having 1–6 carbons, or aryl;
$R^3$, $R^6$ and $R^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —OR$^8$, —SR$^8$, —(NR$^8$R$^9$); or —OSO$_2$R$^{19}$; or a TAIL;

R$^{11}$, R$^{12}$, R$^{13}$, and R$^{14}$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–8 carbons; or a TAIL; or —OR$^8$, —SR$^8$, or —(NR$^8$R$^9$);

TAIL is a heteroatom-containing moiety having the formula LINK-SPACER-CAP;
wherein
LINK is a single covalent bond, —O—, —S—, or —NR$^{20}$—; where R$^{20}$ is H, a linear or branched alkyl having 1–8 carbons, or R$^{20}$ is —SPACER'—CAP';

SPACER and SPACER', which may be the same or different, are covalent linkages, linear or branched, cyclic or heterocyclic, saturated or unsaturated, each having 1–16 nonhydrogen atoms selected from the group consisting of C, N, O and S, such that the linkage begins and ends with a carbon atom, and contains any combination of ether, thioether, amine, ester, amide, or aliphatic, olefinic or aromatic carbon-carbon bonds, or aromatic carbon-nitrogen or nitrogen-nitrogen bonds; wherein all heteroatoms in the linear backbone of SPACER are separated by at least two carbon atoms;

CAP and CAP', which may be the same or different, are —O—R$^{21}$, —S—R$^{21}$, —NR$^{21}$R$^{22}$, or —N$^+$R$^{21}$R$^{22}$R$^{23}$Ψ$^-$;
wherein
R$^{21}$, R$^{22}$, and R$^{23}$ are independently H, or a linear or branched alkyl or cycloalkyl having 1–8 carbons, optionally further substituted by halogen, hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of R$^{21}$, R$^{22}$ and R$^{23}$, taken in combination with SPACER or SPACER' or R$^{20}$ forms a 5- or 6-membered aromatic, heteroaromatic, alicyclic or heteroalicyclic ring, the heteroatoms selected from O, N or S; where Ψ$^-$ is a biologically compatible counterion;
or
CAP and CAP' are independently

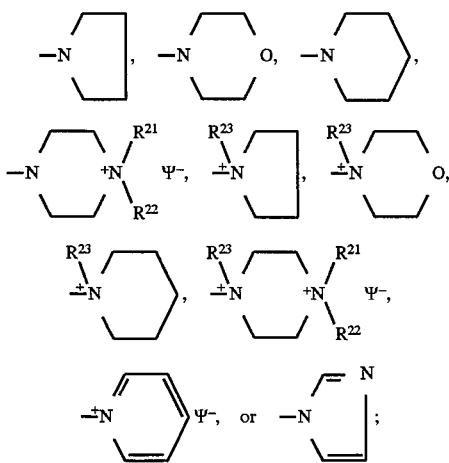

where R$^{21}$, R$^{22}$ and Ψ$^-$ are as defined previously;
such that at least one of R$^3$, R$^4$, R$^6$, R$^7$, R$^{11}$, R$^{12}$, R$^{13}$, and R$^{14}$ is a TAIL; and, where more than one substituent is a TAIL, each TAIL is optionally the same or different;

and
b) incubating the sample and mixture for a time sufficient for the dye compound to combine with the nucleic acid in the sample to form one or more dye-nucleic acid complexes that give a detectable fluorescent signal.

36. A method of staining nucleic acids, according to claim 35, wherein said sample or said mixture comprises an electrophoretic gel.

37. A method of staining nucleic acids, according to claim 35, wherein the dye-nucleic acid complexes are separated by electrophoresis.

38. A method of staining nucleic acids, according to claim 35, wherein said sample comprises a density or sedimentation gradient.

39. A method of staining nucleic acids, according to claim 35, wherein the sample comprises a biological fluid.

40. A method of staining nucleic acids, according to claim 35, wherein the one or more dye-nucleic acid complexes form in a eukaryote cell, a prokaryote cell, a virus, or a viroid.

41. A method of staining nucleic acids, according to claim 40, wherein the complexes form in a eukaryote cell or prokaryote cell that is in a cell, tissue, or biological fluid.

42. A method of staining nucleic acids, according to claim 35, where the sample contains cell-free nucleic acids.

43. A method of detecting a biological structure, comprising
a) combining a sample that contains or is thought to contain a specific biological structure, with a dye of the formula

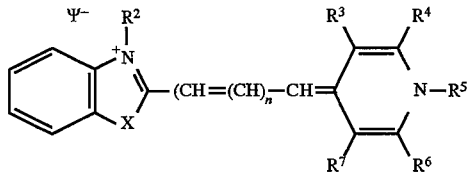

or having the formula

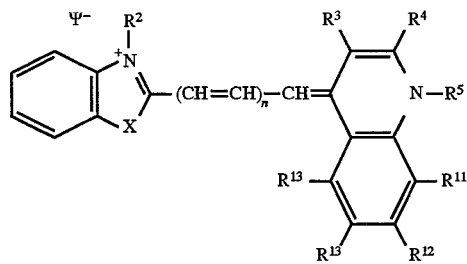

wherein
R$^2$ is ethyl or methyl;
X is O or S;
n=0, 1 or 2;
Ψ$^-$ is a biologically compatible counterion;
R$^5$ is alkyl having 1–6 carbons; or a cyclic substituent that is a substituted or unsubstituted aryl or heteroaryl; or a substituted or unsubstituted cycloalkyl having 3–10 carbons; or R$^5$ is a TAIL;
R$^4$ is an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —OR$^8$, —SR$^8$, (NR$^8$R$^9$); or —OSO$_2$R$^{19}$; or a TAIL; where R$^8$ and R$^9$, which can be the same or different, are independently H; or alkyl groups having 1–6 carbons; or 1–2 alicyclic or aromatic rings; or R$^8$ and R$^9$ taken in combination are —(CH$_2$)$_4$— or —(CH$_2$)$_5$— to give a 5 or 6 membered ring; and where R$^{19}$ is alkyl having 1–6 carbons, or perfluoroalkyl having 1–6 carbons, or aryl; having 1–6 carbons, or aryl;

R$^3$, R$^6$ and R$^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —OR$^8$, —SR$^8$, —(NR$^8$R$^9$); or —OSO$_2$R$^{19}$; or a TAIL;

R$^{11}$, R$^{12}$, R$^{13}$, and R$^{14}$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–8 carbons; or a TAIL; or —OR$^8$, —SR$^8$, or —(NR$^8$R$^9$);

TAIL is a heteroatom-containing moiety having the formula LINK-SPACER-CAP;

wherein

LINK is a single covalent bond, —O—, —S—, or —NR$^{20}$—; where R$^{20}$ is H, a linear or branched alkyl having 1–8 carbons, or R$^{20}$ is —SPACER'—CAP';

SPACER and SPACER', which may be the same or different, are covalent linkages, linear or branched, cyclic or heterocyclic, saturated or unsaturated, each having 1–16 nonhydrogen atoms selected from the group consisting of C, N, O and S, such that the linkage begins and ends with a carbon atom, and contains any combination of ether, thioether, amine, ester, amide, or aliphatic, olefinic or aromatic carbon-carbon bonds, or aromatic carbon-nitrogen or nitrogen-nitrogen bonds; wherein all heteroatoms in the linear backbone of SPACER are separated by at least two carbon atoms;

CAP and CAP', which may be the same or different, are —O—R$^{21}$, —S—R$^{21}$, —NR$^{21}$R$^{22}$, or —N$^+$R$^{21}$R$^{22}$R$^{23}$Ψ$^-$, wherein R$^{21}$, R$^{22}$, and R$^{23}$ are independently H, or a linear or branched alkyl or cycloalkyl having 1–8 carbons, optionally further substituted by halogen, hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of R$^{21}$, R$^{22}$ and R$^{23}$, taken in combination with SPACER or SPACER' or R$^{20}$ forms a 5- or 6-membered aromatic, heteroaromatic, alicyclic or heteroalicyclic ring, the heteroatoms selected from O, N or S; where Ψ$^-$ is a biologically compatible counterion;

or

CAP and CAP' are independently

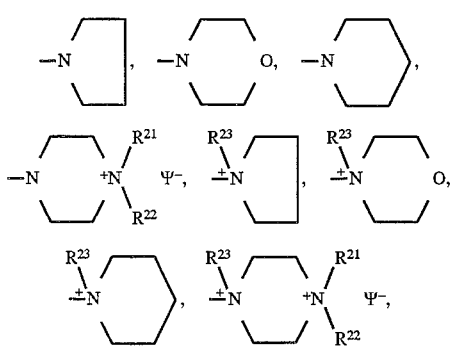

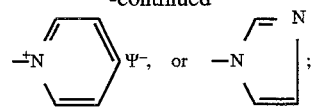

where R$^{21}$, R$^{22}$ and Ψ$^-$ are as defined previously;
such that at least one of R$^3$, R$^4$, R$^6$, R$^7$, R$^{11}$, R$^{12}$, R$^{13}$, and R$^{14}$ is a TAIL; and, where more than one substituent is a TAIL, each TAIL is optionally the same or different;

wherein said biological structure contains nucleic acids;

b) incubating the combined sample and dye compound for a time sufficient for the dye compound to combine with the nucleic acids in the biological structure to form a pattern of dye-nucleic acid complexes having a detectable fluorescent signal that corresponds to the biological structure; and c) detecting the fluorescent signal that corresponds to the biological structure.

44. A method of detecting a biological structure, according to claim 43, wherein said biological structure is a prokayotic cell, eukaryotic cell, virus, or viroid.

45. A method of detecting a biological structure, according to claim 43, wherein the biological structure is a subcellular organelle that is intracellular or extracellular.

46. A method of detecting a biological structure, according to claim 43, wherein the biological structure is a parasitic organism.

47. A method of detecting a biological structure, according to claim 43, wherein the biological structure is a blebbing cell or nucleus.

48. A method of detecting a biological structure, according to claim 43 wherein said fluorescent signal is detected with and instrument.

49. A method of detecting a biological structure, according to claim 43, wherein said sample is a biological fluid, a water sample, or obtained from foodstuffs, or an aqueous wash from a solid surface.

50. A method of characterizing a sample, comprising:
a) combining a sample containing or thought to contain nucleic acid polymers with a dye compound of the formula

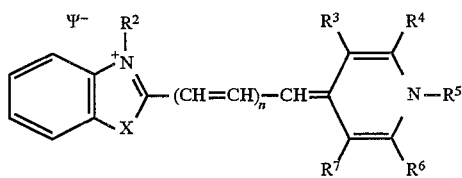

or having the formula

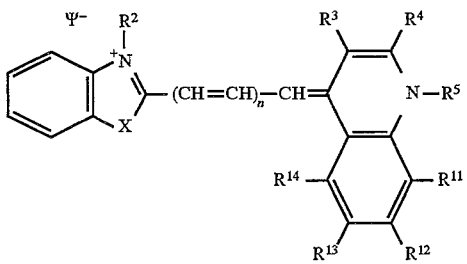

wherein
R$^2$ is ethyl or methyl;
X is O or S;
n=0, 1 or 2;
Ψ$^-$ is a biologically compatible counterion;
R$^5$ is alkyl having 1–6 carbons; or a cyclic substituent that is a substituted or unsubstituted aryl or heteroaryl; or a substituted or unsubstituted cycloalkyl having 3–10 carbons; or $R^5$ is a TAIL;

$R^4$ is an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —($NR^8R^9$); or —$OSO_2R^{19}$; or a TAIL; where $R^8$ and $R^9$, which can be the same or different, are independently H; or alkyl groups having 1–6 carbons; or 1–2 alicyclic or aromatic rings; or $R^8$ and $R^9$ taken in combination are —$(CH_2)_4$— or —$(CH_2)_5$— to give a 5 or 6 membered ring; and where $R^{19}$ is alkyl having 1–6 carbons, or perfluoroalkyl having 1–6 carbons, or aryl; having 1–6 carbons, or aryl;

$R^3$, $R^6$ and $R^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —($NR^8R^9$); or —$OSO_2R^{19}$; or a TAIL;

$R^{11}$, $R^{12}$, $R^{13}$, and $R^{14}$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–8 carbons; or a TAIL; or —$OR^8$, —$SR^8$, or —($NR^8R^9$);

TAIL is a heteroatom-containing moiety having the formula LINK-SPACER-CAP;

wherein

LINK is a single covalent bond, —O—, —S—, or —$NR^{20}$—; where $R^{20}$ is H, a linear or branched alkyl having 1–8 carbons, or $R^{20}$ is —SPACER'—CAP';

SPACER and SPACER', which may be the same or different, are covalent linkages, linear or branched, cyclic or heterocyclic, saturated or unsaturated, each having 1–16 nonhydrogen atoms selected from the group consisting of C, N, O and S, such that the linkage begins and ends with a carbon atom, and contains any combination of ether, thioether, amine, ester, amide, or aliphatic, olefinic or aromatic carbon-carbon bonds, or aromatic carbon-nitrogen or nitrogen-nitrogen bonds; wherein all heteroatoms in the linear backbone of SPACER are separated by at least two carbon atoms;

CAP and CAP', which may be the same or different, are —O—$R^{21}$, —S—$R^{21}$, —$NR^{21}R^{22}$, or —$N^+R^{21}R^{22}R^{23}\Psi^-$;

wherein $R^{21}$, $R^{22}$, and $R^{23}$ are independently H, or a linear or branched alkyl or cycloalkyl having 1–8 carbons, optionally further substituted by halogen, hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\Psi^-$ is a biologically compatible counterion;

or

CAP and CAP' are independently

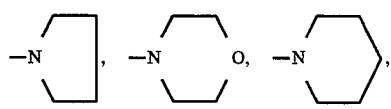

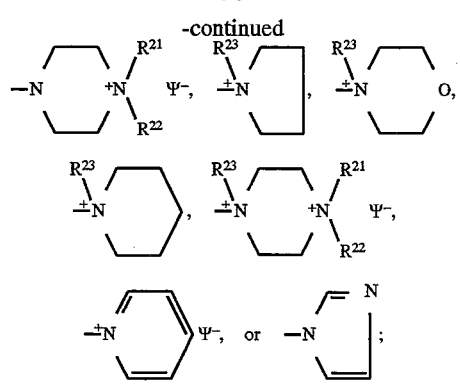

where $R^{21}$, $R^{22}$ and $\Psi^-$ are as defined previously; such that at least one of $R^3$, $R^4$, $R^6$, $R^7$, $R^{11}$, $R^{12}$, $R^{13}$, and $R^{14}$ is a TAIL; and, where more than one substituent is a TAIL, each TAIL is optionally the same or different;

b) incubating the sample for a time sufficient for the dye compound to combine with nucleic acid polymers in the sample to form a staining profile of dye-nucleic acid complexes having detectable fluorescent signals, said staining pattern having a shape, location, spectral property, or intensity that is indicative of a characteristic of the sample; and c) characterizing the sample based on said staining profile.

51. A method of characterizing a sample, according to claim 50, wherein the sample is characterized as a blebbing cell or blebbing nucleus based on the staining profile.

52. A method of characterizing a sample, according to claim 50, wherein the sample is characterized as containing a type of cell based on the staining profile.

53. A method of characterizing a sample, according to claim 52, wherein the sample is characterized as containing a type of blood cell based on the staining pattern.

54. A method of characterizing a sample as containing single stranded (ss) or double stranded (ds) nucleic acid polymers, according to claim 50, wherein the sample contains natural or synthetic nucleic acid polymers that are combined with the dye compound in a ratio of at least one or more molecules of the dye compound per base of the ss or base pair of the ds nucleic acid polymer to form a staining profile having a spectral property of fluorescence intensity at an emission wavelength that is indicative of ss or ds nucleic acid polymers.

55. A method of characterizing a sample, according to claim 54, wherein the ds nucleic acid polymer is DNA that is differentiated from ass nucleic acid polymer that is DNA.

56. A method of characterizing a sample, according to claim 54, wherein the sample contains a solution of purified nucleic acids.

57. A method of characterizing a sample, according to claim 54, wherein the nucleic acid polymers are in cell extracts.

58. A method of characterizing a sample, according to claim 50, wherein the sample is a solution comprising nucleic acid polymers separated by means of relative mobility; where the solution is characterized with respect to purity of the solution, size of polymers in the solution, composition of polymers in the solution, or integrity of polymers in the solution based on the staining profile.

59. A method of characterizing a sample, according to claim 50, further comprising adding one or more additional reagents to the sample, where each additional reagent is capable of a response that is detectably different from the fluorescent signal of the dye-nucleic acid complex.

60. A method of characterizing a sample, according to claim 59, wherein the additional detection reagent is an antibody.

61. A method of characterizing a sample, according to claim 59, wherein the additional detection reagent is a stain selective for an organelle.

62. A method of characterizing a sample, according to claim 59, wherein the sample is a chromosome and one additional reagent that is added to the sample quenches or partially quenches the fluorescent signal from one or more of the dye-nucleic acid complexes, such that the chromosome is characterized as having a certain banding based on the staining pattern.

63. A method of determining cell membrane integrity comprising:
a) incubating a sample containing one or more cells with a first dye compound of the formula

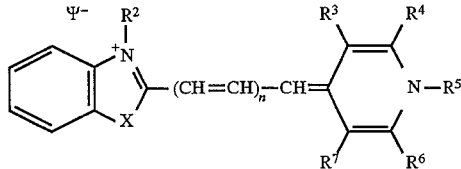

or having the formula

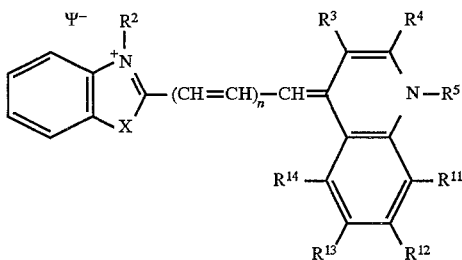

wherein
$R^2$ is ethyl or methyl;
X is O or S;
n=0, 1 or 2;
$\Psi^-$ is a biologically compatible counterion;
$R^5$ is alkyl having 1–6 carbons; or a cyclic substituent that is a substituted or unsubstituted aryl or heteroaryl; or a substituted or unsubstituted cycloalkyl having 3–10 carbons; or $R^5$ is a TAIL;
$R^4$ is an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —($NR^8R^9$); or —$OSO_2R^{19}$; or a TAIL; where $R^8$ and $R^9$, which can be the same or different, are independently H; or alkyl groups having 1–6 carbons; or 1–2 alicyclic or aromatic rings; or $R^8$ and $R^9$ taken in combination are —$(CH_2)_4$— or —$(CH_2)_5$— to give a 5 or 6 membered ring; and where $R^{19}$ is alkyl having 1–6 carbons, or perfluoroalkyl having 1–6 carbons, or aryl; having 1–6 carbons, or aryl; $R^3$, $R^6$ and $R^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —($NR^8R^9$); or —$OSO_2R^{19}$; or a TAIL;
$R^{11}$, $R^{12}$, $R^{13}$, and $R^{14}$, which may be the same or different, are independently H; or an alkyl, alkenyl, polyalkenyl alkynyl or polyalkynyl group having 1–6 carbons; or a halogen; or a substituted or unsubstituted aryl or heteroaryl; or a substituted or unsubstituted cycloalkyl having 3–8 carbons; or a TAIL; or —$OR^8$, —$SR^8$, or —($NR^8R^9$);

TAIL is a heteroatom-containing moiety having the formula LINK-SPACER-CAP;
wherein
LINK is single covalent bond, —O—, —S—, or —$NR^{20}$—; where $R^{20}$ is H, a linear or branched alkyl having 1–8 carbons, or $R^{20}$ is —SPACER'—CAP';
SPACER and SPACER', which may be the same or different, are covalent linkages, linear or branched, cyclic or heterocyclic, saturated or unsaturated, each having 1–16 nonhydrogen atoms selected from the group consisting of C, N, O and S, such that the linkage begins and ends with a carbon atom, and contains any combination of ether, thioether, amine, ester, amide, or aliphatic, olefinic or aromatic carbon-carbon bonds, or aromatic carbon-nitrogen or nitrogen-nitrogen bonds; wherein all heteroatoms in the linear backbone of SPACER are separated by at least two carbon atoms;
CAP and CAP', which may be the same or different, are —$NR^{21}R^{22}$, or —$N^+R^{21}R^{22}R^{23}\Psi^-$;
wherein
$R^{21}$, $R^{22}$, and $R^{23}$ are independently H, or a linear or branched alkyl or cycloalkyl having 1–8 carbons, optionally further substituted by halogen, hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\Psi^-$ is a biologically compatible counterion;
or
CAP and CAP' are independently

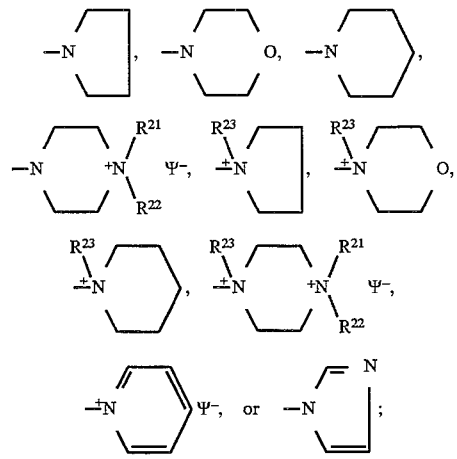

where $R^{21}$, $R^{22}$ and $\Psi^-$ are as defined previously; such that at least one of $R^3$, $R^4$, $R^6$, $R^7$, $R^{11}$, $R^{12}$, $R^{13}$, and $R^{14}$ is a TAIL; and, where more than one substituent is a TAIL, each TAIL is optionally the same or different;
for a time sufficient for the dye compound to combine with intracellular nucleic acids to form a first intracellular dye-nucleic acid complex having a detectable fluorescent signal; and
c) determining cell membrane integrity of cells in the sample based on presence of the detectable fluorescent signal, where the presence of the detectable fluorescent signal indicates that the cell membrane integrity is compromised and the absence of the detectable fluorescent signal indicates that the cell membrane integrity is intact.

64. A method of determining cell membrane integrity, according to claim 63, wherein the dye compound has an overall positive charge of 2+ or greater.

65. A method of determining cell membrane integrity, according to claim 63, wherein the dye compound has an overall positive charge of 3+ or greater.

66. A method of determining cell membrane integrity, according to claim 63, wherein the sample contains eukaryotic cells.

67. A method of determining cell membrane integrity, according to claim 63, wherein the sample contains prokaryotic cells.

68. A method of quantitating nucleic acids in a sample, comprising a) combining an aliquot of a sample, optionally the entire sample, that contains or is thought to contain a nucleic acid, with mixture containing a dye compound of the formula

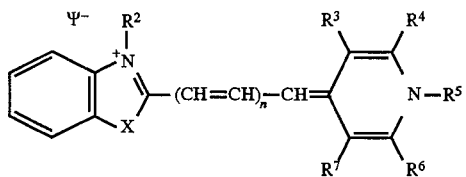

or having the formula

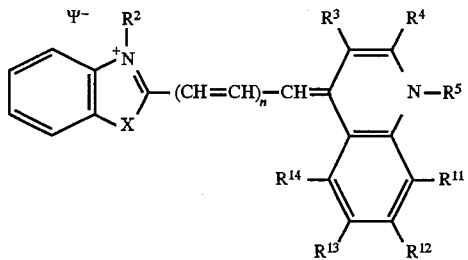

wherein
$R^2$ is ethyl or methyl;
X is O or S;
n=0, 1 or 2;
$\Psi^-$ is a biologically compatible counterion;
$R^5$ is alkyl having 1–6 carbons; or a cyclic substituent that is a substituted or unsubstituted aryl or heteroaryl; or a substituted or unsubstituted cycloalkyl having 3–10 carbons; or $R^5$ is a TAIL;
$R^4$ is an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —($NR^8R^9$); or —$OSO_2R^{19}$; or a TAIL; where $R^8$ and $R^9$, which can be the same or different, are independently H; or alkyl groups having 1–6 carbons; or 1–2 alicyclic or aromatic rings; or $R^8$ and $R^9$ taken in combination are —$(CH_2)_4$— or —$(CH_2)_5$— to give a 5 or 6 membered ring; and where $R^{19}$ is alkyl having 1–6 carbons, or perfluoroalkyl having 1–6 carbons, or aryl; having 1–6 carbons, or aryl;
$R^3$, $R^6$ and $R^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —($NR^8R^9$); or —$OSO_2R^{19}$; or a TAIL;
$R^{11}$, $R^{12}$, $R^{13}$, and $R^{14}$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–8 carbons; or a TAIL; or —$OR^8$, —$SR^8$, or —($NR^8R^9$);

TAIL is a heteroatom-containing moiety having the formula LINK-SPACER-CAP;
wherein
LINK is a single covalent bond, —O—, —S—, or —$NR^{20}$—; where $R^{20}$ is H, a linear or branched alkyl having 1–8 carbons, or $R^{20}$ is —SPACER'—CAP';
SPACER and SPACER', which may be the same or different, are covalent linkages, linear or branched, cyclic or heterocyclic, saturated or unsaturated, each having 1–16 nonhydrogen atoms selected from the group consisting of C, N, O and S, such that the linkage begins and ends with a carbon atom, and contains any combination of ether, thioether, amine, ester, amide, or aliphatic, olefinic or aromatic carbon-carbon bonds, or aromatic carbon-nitrogen or nitrogen-nitrogen bonds; wherein all heteroatoms in the linear backbone of SPACER are separated by at least two carbon atoms;
CAP and CAP', which may be the same or different, are —O—$R^{21}$, —S—$R^{21}$, —$NR^{21}R^{22}$, or —$N^+R^{21}R^{22}R^{23}\Psi^-$;
wherein
$R^{21}$, $R^{22}$, and $R^{23}$ are independently H, or a linear or branched alkyl or cycloalkyl having 1–8 carbons, optionally further substituted by halogen, hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\Psi^-$ is a biologically compatible counterion;
or
CAP and CAP' are independently

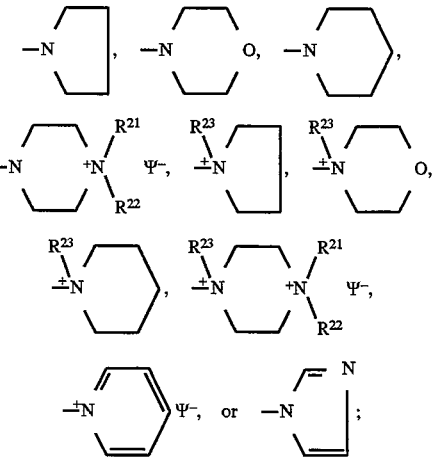

where $R^{21}$, $R^{22}$ and $\Psi^-$ are as defined previously;
such that at least one of $R^3$, $R^4$, $R^6$, $R^7$, $R^{11}$, $R^{12}$, $R^{13}$, and $R^{14}$ is a TAIL; and, where more than one substituent is a TAIL, each TAIL is optionally the same or different;

b) incubating the aliquot and mixture for a time sufficient for the dye compound to combine with the nucleic acid in the sample to form a dye-nucleic acid complex that gives a detectable fluorescent signal; and c) quantifying the nucleic acid present in said sample based on comparison of the detectable fluorescent signal with a fluorescent standard characteristic of a given amount of nucleic acid.

69. A method of quantitating nucleic acids in a sample, according to claim 68, wherein said sample or said mixture is an electrophoretic gel.

70. A method of quantitating nucleic acids in a sample, according to claim 68, wherein said nucleic acids are natural or synthetic oligonucleotides that are ssDNA, dsDNA, RNA, or RNA/DNA hybrids.

71. a method of quantitating nucleic acids in a sample, according to claim 68, wherein said nucleic acids are polymerase chain reaction amplification products.

72. A method of quantitating nucleic acids in a sample of cells that has been grown in a tissue or in a culture medium, according to claim 68, wherein said aliquot is an aliquot prepared by the lysis of all or a portion of said cells.

73. A method of quantitating nucleic acids in a sample, according to claim 72, further comprising
d) taking one or more additional aliquots from the sample over time, where each aliquot is prepared by lysis of a portion of said cells;
e) repeating steps a) through c) for each aliquot; and
f) comparing the amount of nucleic acid in the sample over time to determine cell proliferation in the sample.

74. A method of quantitating ds nucleic acids in a sample, according to claim 68, wherein the aliquot of a sample that contains a specified amount of total nucleic acid is combined with more than one molar equivalent of the dye, where the dye is selective for ds nucleic acids, to form a dye-nucleic acid complex that gives a detectable fluorescent signal having fluorescence intensity at an emission wavelength that is indicative of ds nucleic acid polymers; quantifying the ds nucleic acid present in said sample based on comparison of the detectable fluorescent signal with a fluorescent standard characteristic of a given amount of ds nucleic acid.

75. A method of analyzing nucleic acid-analyte interactions, comprising:
a) forming a fluorescent complex comprising a nucleic acid polymer and one or more dye molecules of the formula:

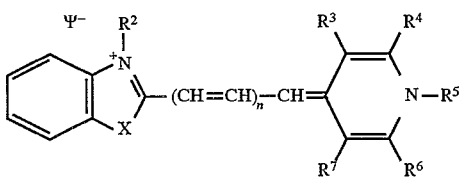

or having the formula

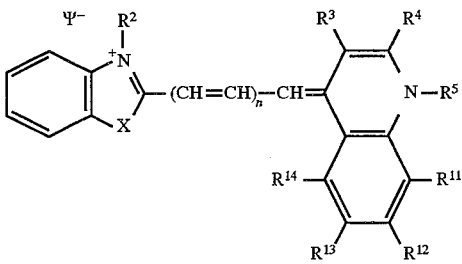

wherein
$R^2$ is ethyl or methyl;
X is O or S;
n=0, 1 or 2;
$\Psi^-$ is a biologically compatible counterion;
$R^5$ is alkyl having 1–6 carbons; or a cyclic substituent that is a substituted or unsubstituted aryl or heteroaryl; or a substituted or unsubstituted cycloalkyl having 3–10 carbons; or $R^5$ is a TAIL;

$R^4$ is an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —$(NR^8R^9)$; or —$OSO_2R^{19}$; or a TAIL; where $R^8$ and $R^9$, which can be the same or different, are independently H; or alkyl groups having 1–6 carbons; or 1–2 alicyclic or aromatic rings; or $R^8$ and $R^9$ taken in combination are —$(CH_2)_4$— or —$(CH_2)_5$— to give a 5 or 6 membered ring, and where $R^{19}$ is alkyl having 1–6 carbons, or perfluoroalkyl having 1–6 carbons, or aryl; having 1–6 carbons, or aryl;
$R^3$, $R^6$ and $R^7$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —$OR^8$, —$SR^8$, —$(NR^8R^9)$; or —$OSO_2R^{19}$; or a TAIL;
$R^{11}$, $R^{12}$, $R^{13}$, and $R^{14}$, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–8 carbons; or a TAIL; or —$OR^8$, —$SR^8$, or —$(NR^8R^9)$;

TAIL is a heteroatom-containing moiety having the formula LINK-SPACER-CAP;
wherein
LINK is a single covalent bond, —O—, —S—, or —$NR^{20}$—; where $R^{20}$ is H, a linear or branched alkyl having 1–8 carbons; or $R^{20}$ is —SPACER'—CAP';
SPACER and SPACER', which may be the same or different, are covalent linkages, linear or branched, cyclic or heterocyclic, saturated or unsaturated, each having 1–16 nonhydrogen atoms selected from the group consisting of C, N, O and S, such that the linkage begins and ends with a carbon atom, and contains any combination of ether, thioether, amine, ester, amide, or aliphatic, olefinic or aromatic carbon-carbon bonds, or aromatic carbon-nitrogen or nitrogen-nitrogen bonds; wherein all heteroatoms in the linear backbone of SPACER are separated by at least two carbon atoms;
CAP and CAP', which may be the same or different, are —O—$R^{21}$, —S—$R^{21}$, —$NR^{21}R^{22}$, or —$N^+R^{21}R^{22}R^{23}\Psi^-$;
wherein
$R^{21}$, $R^{22}$, and $R^{23}$ are independently H, or a linear or branched alkyl or cycloalkyl having 1–8 carbons, optionally further substituted by halogen, hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\Psi^-$ is a biologically compatible counterion;
or
CAP and CAP' are independently

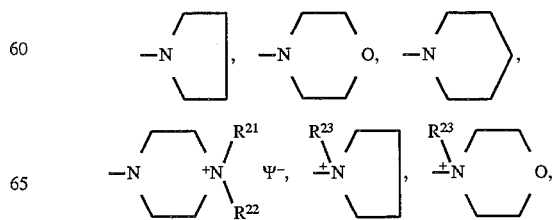

-continued

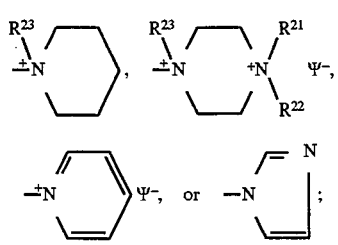

where R²¹, R²² and Ψ⁻ are as defined previously;
such that at least one of R³, R⁴, R⁶, R⁷, R¹¹, R¹², R¹³, and R¹⁴ is a TAIL; and, where more than one substituent is a TAIL, each TAIL is optionally the same or different;
wherein the fluorescent complex has a set of characteristic spectral properties;
b) combining the fluorescent complex with a sample that contains or is thought to contain an analyte that interacts with the nucleic acid polymer;
c) detecting a change in the spectral properties of the fluorescent complex; and
d) determining the presence or activity of the analyte in said sample based on comparison of the change in spectral properties of the complex with a fluorescent standard characteristic of analyte activity.

76. A method of analyzing nucleic acid-analyte interactions, according to claim 75, wherein the sample is a cell that is combined with the fluorescent complex by artificial means.

77. A method of analyzing nucleic acid-analyte interactions, according to claim 75, wherein the sample contains cell-free nucleic acid polymers.

78. A method analyzing nucleic acid-analyte interactions, according to claim 75, wherein the analyte is a protein.

79. A method of analyzing nucleic acid-analyte interactions, according to claim 75, wherein the analyte is a drug.

80. A compound having the formula

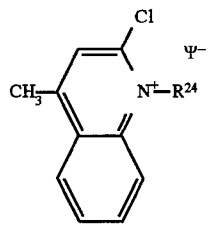

wherein R²⁴ is a linear or branched alkyl having 1–6 carbons; and Ψ⁻ is a biologically compatible counterion.

81. A compound of the formula

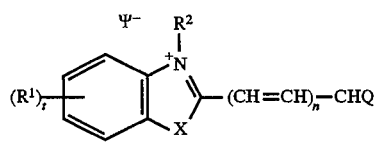

wherein
each R¹ is independently H; or an alkyl group having from 1–6 carbons; an alkoxy group having from 1–6 carbons; or a trifluoromethyl; or a halogen; and t=1–4;
R² is an alkyl group having 1–6 carbons;
X is O, S, Se or NR¹⁵, where R¹⁵ is an alkyl group having 1–6 carbons; or X is CR¹⁶R¹⁷ where R¹⁶ and R¹⁷, which may be the same or different, are independently alkyl groups having 1–6 carbons, or R¹⁶ and R¹⁷ taken in combination complete a five or six membered saturated ring;
n=0, 1 or 2;
Ψ⁻ is a biologically compatible counterion;
Q has the formula Q 1 or Q2

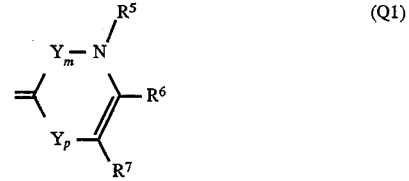

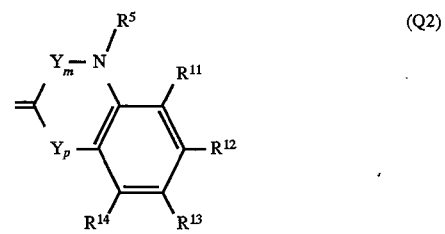

wherein
Y is —CR³=CR⁴—;
p and m=0 or 1, such that p+m=1;
R⁵ is an alkyl, alkenyl, polyalkenyl, alkynyl or polyalkynyl group having 1–6 carbons; or R⁵ is a TAIL;
R⁴ is an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —OR⁸, —SR⁸, —(NR⁸R⁹); or —OSO₂R¹⁹; or a TAIL; where R⁸ is an alkyl group having 1–6 carbons, or 1–2 alicyclic or aromatic rings; and R⁹ is H, an alkyl group having 1–6 carbons, or 1–2 alicyclic or aromatic rings; or R⁸ and R⁹ taken in combination are —(CH₂)₄— or —(CH₂)₅— to give a 5 or 6 membered ring; and where R¹⁹ is alkyl having 1–6 carbons, or perfluoroalkyl having 1–6 carbons, or aryl;
R³, R⁶ and R⁷, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–10 carbons; or —OR⁸, —SR⁸, —(NR⁸R⁹); or —OSO₂R¹⁹; or a TAIL;
or R⁶ and R⁷, taken in combination are —(CH₂)ᵥ— where v=3 or 4, or R⁶ and R⁷ form a fused aromatic ring according to formula Q2;
R¹¹, R¹², R¹³, and R¹⁴, which may be the same or different, are independently H; or an alkyl, alkenyl, polyalkenyl, alkynyl or polyalkynyl group having 1–6 carbons; or a halogen; or a substituted or unsubstituted aryl or heteroaryl; or a substituted or unsubstituted cycloalkyl having 3–8 carbons; or a TAIL; or —OR⁸, —SR⁸, or —(NR⁸R⁹);
TAIL is a heteroatom-containing moiety having the formula LINK-SPACER-CAP;
wherein
LINK is a single covalent bond, —O—, —S—, or —NR²⁰—; where R²⁰ is H, a linear or branched alkyl having 1–8 carbons, or R²⁰ is —SPACER'—CAP';
SPACER and SPACER', which may be the same or different are linear or branched, cyclic or heterocyclic, saturated or unsaturated covalent linkages, each having 1–16 nonhydrogen atoms selected from the group consisting of C, N, P, O and S, such that the linkage contains any combination of ether, thioether, amine, ester, amide bonds; or single, double, triple or aromatic carbon-carbon bonds; or phosphorus-oxygen, phosphorus-sulfur bonds, nitrogen-nitrogen or nitrogen-oxygen bonds; or aromatic or heteroaromatic bonds;

CAP and CAP', which may be the same or different, are —O—$R^{21}$, —S—$R^{21}$, —$NR^{21}R^{22}$, or —$N^+R^{21}R^{22}R^{23}\Psi^-$; wherein $R^{21}$, $R^{22}$, and $R^{23}$ are independently H, or a linear or branched alkyl or cycloalkyl having 1–8 carbons, optionally further substituted by hydroxy, alkoxy having 1–8 carbons, carboxyalkyl having 1–8 carbons, or phenyl, where phenyl is optionally further substituted by halogen, hydroxy, alkoxy having 1–8 carbons, aminoalkyl having 1–8 carbons, or carboxyalkyl having 1–8 carbons; or, one or more of $R^{21}$, $R^{22}$ and $R^{23}$, taken in combination with SPACER or SPACER' or $R^{20}$ forms a 5- or 6-membered aromatic, heteroaromatic, alicyclic or heteroalicyclic ring, the heteroatoms selected from O, N or S; where $\Psi^-$ is a biologically compatible counterion;

or

CAP and CAP' are independently

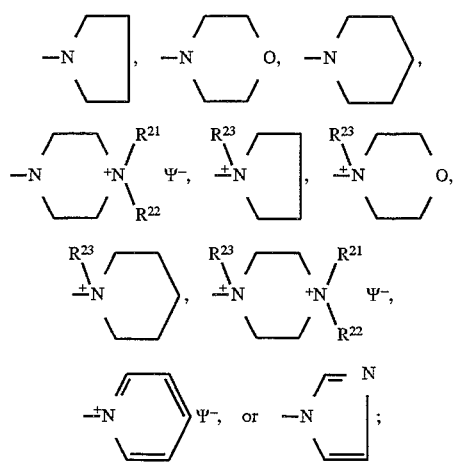

where $R^{21}$, $R^{22}$ and $\Psi^-$ are as defined previously;

such that when $R^5$ is a TAIL, LINK is a single bond; and, where more than one of $R^2, R^3, R^4, R^5, R^6, R^7, R^{11}, R^{12}, R^{13}$, and $R^{14}$ is a TAIL, each TAIL is optionally the same or different.

82. A compound, as claimed in claim 81, of the formula

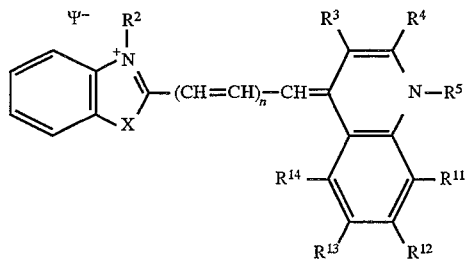

wherein $R^2$ is an alkyl group having 1–2 carbons;

X is O or S;

n=0 or 1;

$R^3$ is H;

$R^5$ is an alkyl having 1–6 carbons; and where TAIL is a heteroatom-containing moiety having the formula LINK-SPACER-CAP;

LINK is a single covalent bond, —O—, —S—, or —$NR^{20}$—; where $R^{20}$ is H, a linear or branched alkyl having 1–8 carbons, or $R^{20}$ is —SPACER'—CAP';

SPACER and SPACER' independently have the formula —$(CH_2)_k$—, where k=1–8;

CAP and CAP', which may be the same or different, are —$NR^{21}R^{22}$ or —$N^+R^{21}R^{22}R^{23}\Psi^-$; where $R^{21}$, $R^{22}$, and $R^{23}$ are independently methyl or ethyl.

83. A compound, as claimed in claim 82, wherein $R^4$ is a TAIL.

84. A compound, as claimed in claim 82, wherein $R^4$ is a halogen, —$OR^8$, —$SR^8$, —$(NR^8R^9)$ or —$OSO_2R^{19}$.

85. A compound, as claimed in claim 82, wherein $R^4$ is an alkyl having 1–6 carbons.

86. A compound, as claimed in claim 81, wherein none of $R^3, R^4, R^6, R^7, R^{11}, R^{12}, R^{13}$ and $R^{14}$ is a substituted or unsubstituted aryl or heteroaryl or a substituted or unsubstituted cycloalkyl having 3–10 carbons.

87. A compound, as claimed in claim 86, wherein p is 0 and m is 1.

88. A compound, as claimed in claim 86, wherein each $R^1$ is H, $R^2$ is methyl or ethyl, and X is O or S.

89. A compound, as claimed in claim 86, wherein p=0, m=1; and n=0 or 1.

90. A compound, as claimed in claim 86, wherein $R^4$ is a halogen, —$OR^8$, —$SR^8$, —$(NR^8R^9)$, or —$OSO_2R^{19}$.

91. A compound, as claimed in claim 86, wherein $R^4$ is an alkyl having 1–6 carbons.

92. A compound, as claimed in claim 86, wherein $R^4$ is a TAIL.

93. A compound, as claimed in claim 86, wherein $R^{20}$ is H or a linear or branched alkyl having 1–8 carbons.

94. A compound, as claimed in claim 86, wherein SPACER and SPACER' independently have the formula —$(CH_2)_k$—, where k=1–8.

95. A compound, as claimed in claim 86, wherein $R^{21}$, $R^{22}$, and $R^{23}$ are independently methyl or ethyl.

96. A compound, as claimed in claim 86, wherein $R^5$ is a TAIL.

97. A compound, as claimed in claim 86, wherein $R^5$ is an alkyl having 1–6 carbons.

* * * * *

UNITED STATES PATENT AND TRADEMARK OFFICE
CERTIFICATE OF CORRECTION

PATENT NO. : 5,658,751
DATED : Aug. 19, 1997
INVENTOR(S) : Yue et al.

It is certified that error appears in the above-indentified patent and that said Letters Patent is hereby corrected as shown below:

At Col. 2, line 56, "1000mg/mL" should be – –1000 ng/mL– –.

At Col. 3, line 39, "(–NR$^2$ –)" should be – – (–NR$^{20}$–) – –.

At Col. 13, lines 4-12, the structure should be

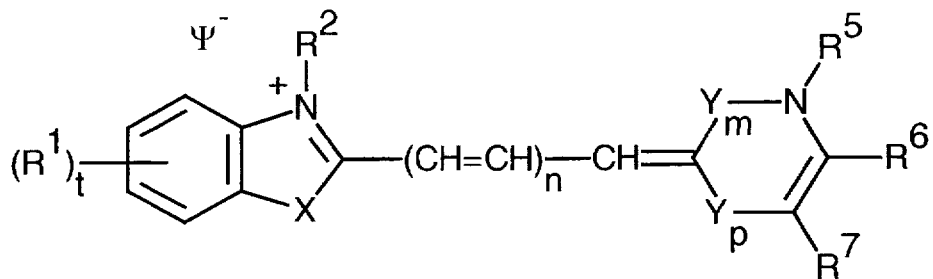

At Col. 27, line 18, "ease" should be – –case– –.

At Col. 31, line 48, "thiol. alkoxide" should be – –thiol, alkoxide– –.

At Col. 35, line 53, "result era successful" should be – –result of a successful– –.

At Col. 36, line 67, "gain, produce" should be – –grain, produce– –.

At Col. 39, line 63, "The l of" should be – –The level of– –.

UNITED STATES PATENT AND TRADEMARK OFFICE
CERTIFICATE OF CORRECTION

PATENT NO. : 5,658,751                            Page 2 of 5
DATED      : Aug. 19, 1997
INVENTOR(S) : Yue et al.

It is certified that error appears in the above-indentified patent and that said Letters Patent is hereby corrected as shown below:

At Col. 44, line 49, immediately below Table 9, should appear - -SYTO 14 and Hoechst 33342 are available commercially from Molecular Probes, Inc. The designation "mitochondria" indicates staining of the entire mitochondrion; the designation "mitochondrial nucleoids" indicates punctate staining within the mitochondrion, thought to be labeling of the mitochondrial DNA. The designation "n.d." indicates dye/cell type combinations that were not tested.- -.

At Col. 53, lines 53-64, the structure should be

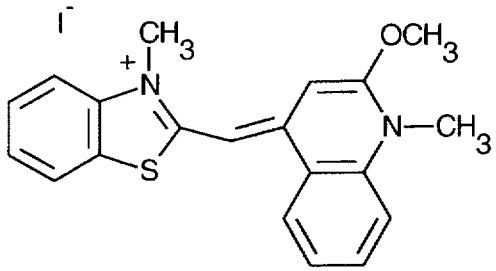

UNITED STATES PATENT AND TRADEMARK OFFICE
CERTIFICATE OF CORRECTION

PATENT NO. : 5,658,751
DATED : Aug. 19, 1997
INVENTOR(S) : Yue et al.

It is certified that error appears in the above-indentified patent and that said Letters Patent is hereby corrected as shown below:

At Col. 54, lines 37-53, the structure should be

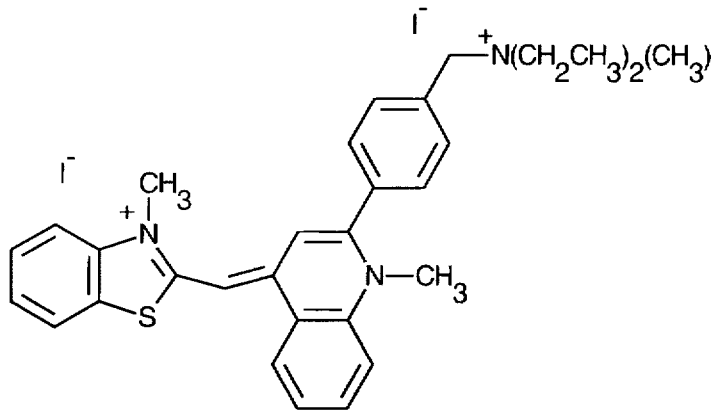

At Col. 60, line 13, "random ping" should be --random priming--.

At Col. 61, line 31, "gel that is east" should be --gel that is cast--.

At Col. 65, line 2, "(1963)" should be --(1993)--.

At Col. 66, line 19, "The fast sample" should be --The first sample--.

At Col. 69, line 47, "488 urn" should be --488 nm--.

UNITED STATES PATENT AND TRADEMARK OFFICE
CERTIFICATE OF CORRECTION

PATENT NO. : 5,658,751
DATED : Aug. 19, 1997
INVENTOR(S) : Yue et al.

It is certified that error appears in the above-indentified patent and that said Letters Patent is hereby corrected as shown below:

At Col. 71, lines 23-29, the structure should be

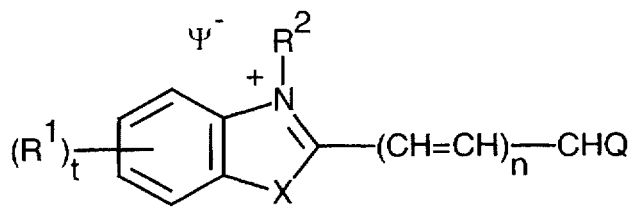

At Col. 75, line 4, "oleic" should be – –olefinic– –.

At Col. 76, line 24, "(NRR$^9$);" should be – – (NR$^8$R$^9$)– –.

At Col. 76, line 61, "or –N$^+$R$^{21}$R$^{23}$Y–;" should be – –or –N$^+$R$^{21}$R$^{22}$R$^{23}$Ψ–; – –.

At Col. 79, line 13, "counterion;" should be – –counterion; or– –.

UNITED STATES PATENT AND TRADEMARK OFFICE
CERTIFICATE OF CORRECTION

PATENT NO. : 5,658,751
DATED : Aug. 19, 1997
INVENTOR(S) : Yue et al.

It is certified that error appears in the above-indentified patent and that said Letters Patent is hereby corrected as shown below:

At Col. 82, lines 40-49, the structure should be

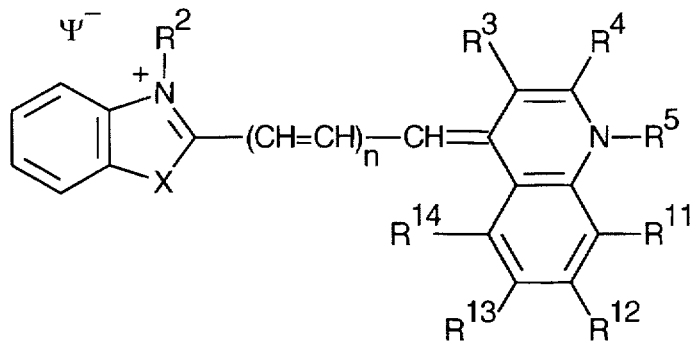

At Col. 84, line 32, "with and instrument." should be – –with an instrument– –.

Signed and Sealed this

First Day of February, 2000

Attest:

Q. TODD DICKINSON

Attesting Officer

Acting Commissioner of Patents and Trademarks